US011490852B1

(12) United States Patent
Kurani et al.

(10) Patent No.: US 11,490,852 B1
(45) Date of Patent: Nov. 8, 2022

(54) WEARABLE DEVICE FOR DETECTING MICROORGANISMS, STERILIZING PATHOGENS, AND ENVIRONMENTAL MONITORING

(71) Applicants: Hemal B Kurani, Sunnyvale, CA (US); Hetal B Kurani, Sunnyvale, CA (US)

(72) Inventors: Hemal B Kurani, Sunnyvale, CA (US); Hetal B Kurani, Sunnyvale, CA (US)

( * ) Notice: Subject to any disclaimer, the term of this patent is extended or adjusted under 35 U.S.C. 154(b) by 0 days.

(21) Appl. No.: 17/397,798

(22) Filed: Aug. 9, 2021

(51) Int. Cl.
*A61B 5/00* (2006.01)
*A61L 2/00* (2006.01)

(52) U.S. Cl.
CPC ............ *A61B 5/411* (2013.01); *A61B 5/0002* (2013.01); *A61B 5/0077* (2013.01); *A61B 5/681* (2013.01); *A61B 5/742* (2013.01); *A61B 5/746* (2013.01); *A61B 5/7475* (2013.01); *A61L 2/0011* (2013.01); *A61B 2560/0214* (2013.01); *A61B 2560/0242* (2013.01); *A61B 2562/029* (2013.01); *A61B 2562/0219* (2013.01); *A61B 2562/0247* (2013.01); *A61B 2562/0271* (2013.01)

(58) Field of Classification Search
CPC ............ A61B 5/68–6831; A61B 5/411; A61B 5/0002; A61B 5/0077; A61B 5/681; A61B 5/742; A61B 5/746; A61B 5/7475; A61B 2560/0214; A61B 2560/0242; A61B 2562/0219; A61B 2562/0247; A61B 2562/0271; A61B 2562/029; A61L 2/0011
See application file for complete search history.

(56) References Cited

U.S. PATENT DOCUMENTS

| 5,246,004 A | 9/1993 | Clarke et al. |
| 6,579,231 B1 | 6/2003 | Phipps |
| (Continued) | | |

FOREIGN PATENT DOCUMENTS

| EP | 2430461 B2 | 8/2021 |
| JP | 5707399 B2 | 4/2015 |
| (Continued) | | |

OTHER PUBLICATIONS

Baron S. Medical Microbiology, 4th edition. 1996, University of Texas Medical Branch at Galveston, Galveston, Texas.
(Continued)

*Primary Examiner* — Shirley X Jian

(57) ABSTRACT

A wearable device consists of a smart band and a display unit. The smart band comprises a microbial biosensor, a particulate matter sensor, an enviro sensor, a single board computer, a power supply unit, a band fastener, and a set of watch adapters. The microbial biosensor detects, measures, and monitors beneficial microorganisms and pathogens in a nasal cavity, an oral cavity, or on a surface. The microbial biosensor sterilizer kills pathogens. The particulate matter sensor detects, measures, and monitors a set of suspended particles in the surrounding air comprising beneficial microorganisms, pathogens, pollen grains, dust mite allergens, and an air quality index. The enviro sensor detects, monitors, and measures environmental conditions surrounding the user. A computing system comprises a wearable device, a microbiome mobile application, a user, a mobile device, a laboratory testing facility, a cloud server, and a physician.

9 Claims, 48 Drawing Sheets

(56) References Cited

U.S. PATENT DOCUMENTS

| | | | |
|---|---|---|---|
| 6,996,472 | B2 | 2/2006 | Wilkes et al. |
| 7,167,731 | B2 | 1/2007 | Nelson |
| 7,430,046 | B2 | 9/2008 | Jiang et al. |
| 7,542,137 | B2 | 6/2009 | Murugkar et al. |
| 8,086,301 | B2 | 12/2011 | Cho et al. |
| 8,945,017 | B2 | 2/2015 | Venkatraman et al. |
| 9,291,549 | B2 | 3/2016 | Schwoebel et al. |
| 9,536,449 | B2 | 1/2017 | Connor |
| 9,870,716 | B1 | 1/2018 | Rao et al. |
| 9,974,451 | B2 | 5/2018 | Newberry |
| 10,299,708 | B1 | 6/2019 | Poeze et al. |
| 10,561,321 | B2 | 2/2020 | Valys et al. |
| 10,624,550 | B2 | 4/2020 | Soli et al. |
| 10,687,717 | B1 | 6/2020 | Peterson et al. |
| 10,694,960 | B2 | 6/2020 | Saponas et al. |
| 10,724,068 | B2 | 7/2020 | Samadpour |
| 2007/0032981 | A1* | 2/2007 | Merkel .............. A63B 24/0062 235/105 |
| 2008/0146890 | A1* | 6/2008 | LeBoeuf .............. A61B 5/031 600/300 |
| 2010/0056873 | A1* | 3/2010 | Allen ................ A61B 5/6804 600/300 |
| 2010/0217099 | A1* | 8/2010 | LeBoeuf .............. A61B 5/002 600/301 |
| 2014/0335469 | A1* | 11/2014 | Boyden .................. A61C 7/20 433/215 |
| 2015/0313542 | A1* | 11/2015 | Goldberg ............. G04B 47/063 368/282 |
| 2016/0022024 | A1* | 1/2016 | Vetter ................ A61B 5/682 324/707 |
| 2016/0062623 | A1* | 3/2016 | Howard ................ G06F 3/0412 715/788 |
| 2016/0177366 | A1* | 6/2016 | Auner .................. G01J 3/4406 435/5 |
| 2017/0112434 | A1* | 4/2017 | Lane .................... A61B 5/6846 |
| 2017/0156597 | A1* | 6/2017 | Whitehead .............. A61B 5/01 |
| 2019/0117099 | A1* | 4/2019 | Bardy .................. A61B 5/6833 |
| 2020/0152312 | A1* | 5/2020 | Connor .................... A61B 5/11 |
| 2020/0245822 | A1* | 8/2020 | Chacon, Jr. ............ G04G 17/08 |
| 2020/0309703 | A1* | 10/2020 | Luk .................... G01N 21/6486 |
| 2020/0345300 | A1* | 11/2020 | Potyrailo ............. A61B 5/6814 |
| 2021/0356771 | A1* | 11/2021 | Poteet ...................... A61L 2/26 |
| 2022/0084650 | A1* | 3/2022 | Rakshit .................. G16H 20/30 |

FOREIGN PATENT DOCUMENTS

| | | | |
|---|---|---|---|
| KR | 20220003433 A | * | 1/2022 |
| WO | WO-2017136383 A1 | * | 8/2017 |
| WO | WO-2021231287 A1 | * | 11/2021 ............... A61L 9/00 |

OTHER PUBLICATIONS

Stetzenbach LD. Airborne infectious microorganisms. Encyclopedia of Microbiology. 2009, pp. 175-182. Elsevier.

Zhang L, et al. Micro-/nanofiber optics: merging photonics and material science on nanoscale for advanced sensing technology, iScience. 2020, vol. 23, p. 100810. Elsevier.

Tong L. Micro/nanofibre optical sensors: challenges and prospects. Sensors. 2018, vol. 18, p. 903. MDPI, Basel, Switzerland.

Bayo-Monton J-L, et al. Wearable sensors integrated with Internet of Things for advancing ehealthcare. Sensors. 2018, vol. 18, p. 1851. MDPI, Basel, Switzerland.

Kamisalic A, et al. Sensors and functionalities of non-invasive wrist-wearable devices: a review. Sensors. 2018, vol. 18, p. 1714. MDPI, Basel, Switzerland.

Issadore D, Chung HJ, Chung J, et al. µHall chip for sensitive detection of bacteria. Adv Healthc Mater. 2013, vol. 2, pp. 1224-1228. John Wiley & Sons.

Burrell CJ, Howard CR, Murphy FA. Virion structure and composition. In: Fenner and White's Medical Viology, 5th edition. 2017, pp. 27-37. Elsevier.

McNeil LK, et al. The National Microbial Pathogen Database Resource (NMPDR). Nucleic Acids Res. 2007, vol. 35, pp. D347-D353. Oxford University Press, UK.

Zhulin IB. Databases for microbiologists. J Bacteriol. 2015, vol. 197, pp. 2458-2467, American Society for Microbiology, Washington, DC.

Yoo SM, Lee SY. Optical biosensors for the detection of pathogenic organisms. Trends in Biotechnology. 2016, vol. 34, pp. 7-25. Elsevier.

Singh R, et al. Biosensors for pathogen detection: a smart approach towards clinical diagnosis. In: Sensors and Actuators B: Chemical. 2014, vol. 197, pp. 385-404. Elsevier.

Senturk E, Aktop S, Sanlibaba P, et al. Biosensors: a novel approach to detect food-borne pathogens. Appli Microbiol Open Access. 2018, vol. 4, p. 151. Uploaded by author.

Aas JA, et al. Defining the normal bacterial flora of the oral cavity. J Clin Microbiol. 2005, vol. 43, pp. 5721-5732. American Society for Microbiology, Washington, DC.

Slezak T, Hart B, Jaing C. Design of genomic signatures for pathogen identification and characterization. Microbial Forensics. 2020, pp. 299-312. Elsevier.

Ukhanova O, Bogomolova E. Airborne allergens. In: Allergic Diseases—New Insights. 2015, IntechOpen, London, England.

Ghosh B, et al. Review of bioaerosols in indoor environment with special reference to sampling, analysis and control mechanisms. Eviron Int. 2015, vol. 85, pp. 254-272.

Amerman EC. Exploring anatomy & physiology in the laboratory, core concepts, 2nd edition. 2018. Morton Publishing Company, Englewood, Colorado.

Topol E. Deep medicine: how artificial intelligence can make healthcare human again. 2019. Basic Books, New York, New York.

Tate JR, Myers GL. Harmonization of clinical laboratory test results. EJIFCC. 2016, vol. 27, pp. 5-14. IFCC, Milan, Italy.

* cited by examiner

General purpose input output pinout numbering diagram 410
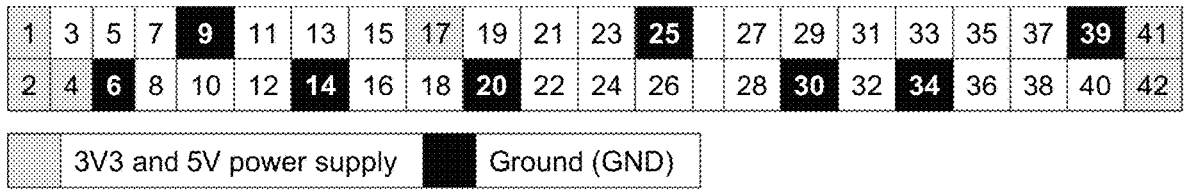
General purpose input output pinout function 450
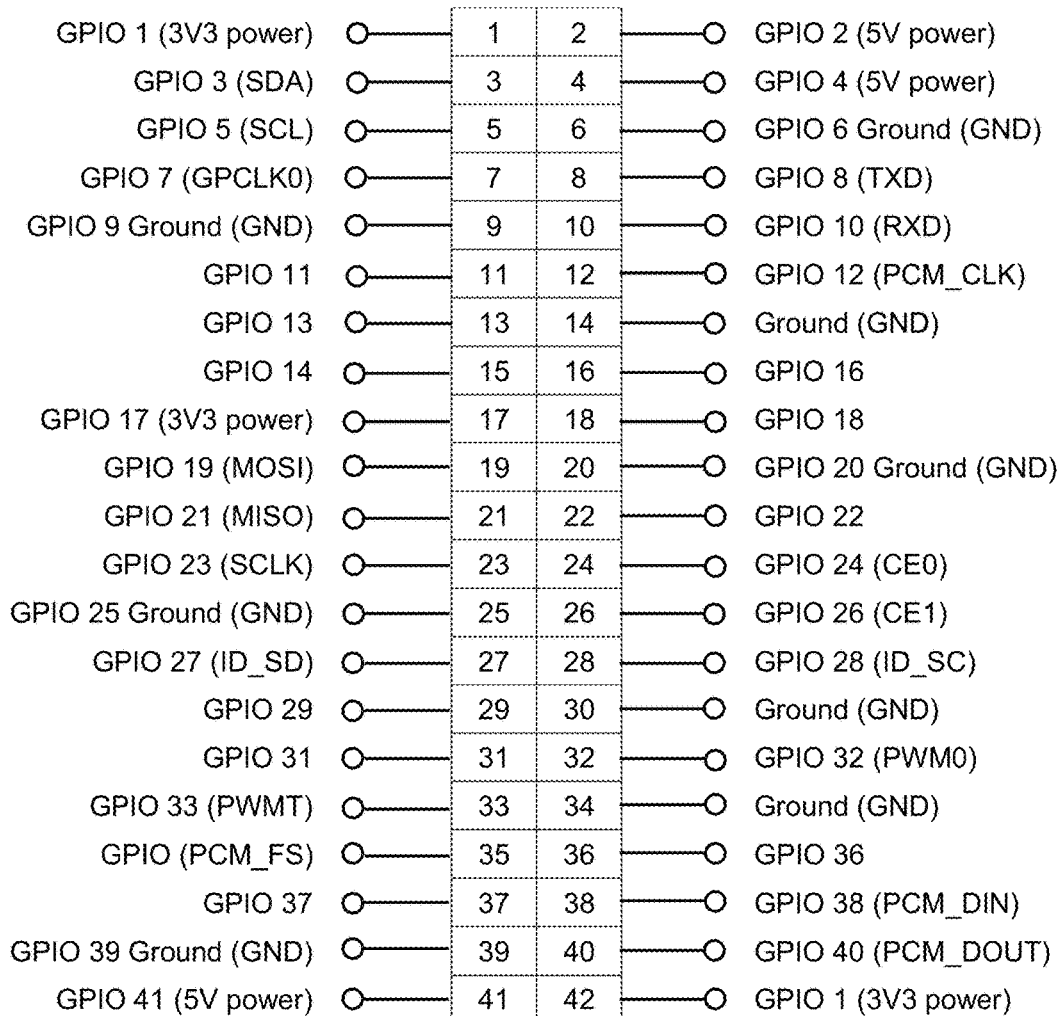
FIG. 4

General purpose input output pinout function description table 500

| Voltage 502 <br>  GND / Power | Three 5V pins and three 3V3 pins are present on the single board microcomputer, and there are eight ground pins (0V), which are not configurable. The remaining pins are all general purpose 3V3 pins, meaning outputs are set to 3V3 and inputs are 3V3 tolerant. <br> Almost all integrated circuits (ICs) sensors have at least two pins that connect to the power rails of the circuit in which they are installed. These are known as the power-supply pins. <br> A sensor component power supply pin Vcc = Collector supply voltage and VDD = Drain supply is connected to the single board microcomputer GPIO 5V or 3V pin per the specification. The other power-supply pin is referred to as ground (abbreviated "GND"). |
|---|---|
| Inputs 504 <br> 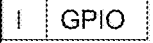 I GPIO | A GPIO pin designated as an input pin can be read as high (3V3) or low (0V). This is done with internal pull-up or pull-down resistors. Pins GPIO3 and GPIO5 have fixed pull-up resistors, but for other pins this can be configured in software. A GPIO pin is assigned as an input pin through SBM software settings. |
| Outputs 506 <br>  O GPIO | A GPIO pin designated as an output pin can be set to high (3V3) or low (0V). The GPIO pin is assigned as an output pin through SBM software settings. |
| Alternative functions | GPIO pins can be used with a variety of alternative functions, some are available on all pins, others on specific pins as follows: |
|  | Pulse-Width Modulation (PWM) 508 <br> Software PWM available on all pins. <br> Hardware PWM available on GPIO 32, GPIO 33, GPIO 12, and GPIO 35. |
| 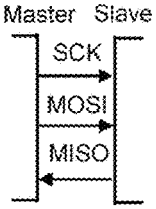 Master Slave SCK MOSI MISO | Serial Peripheral Interface (SPI) 510 <br> SPI0: MOSI (GPIO 19); MISO (GPIO 21); SCLK (GPIO 23); CE0 (GPIO 24), CE1 (GPIO 26) <br> SPI1: MOSI (GPIO 38); MISO (GPIO 35); SCLK (GPIO 40); CE0 (GPIO 12); CE1 (GPIO 11); CE2 (GPIO 36). <br> MOSI – Master Out Slave In, MISO – Master In Slave Out, SCLK – Serial CLocK Signal, CE – Chip Enable |
| 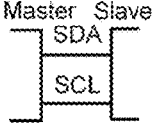 Master Slave SDA SCL | Inter-Integrated Circuit (I2C) 512 <br> SDA Data (Serial Data): (GPIO 3); SCL Clock (GPIO 5) <br> EEPROM Data: (GPIO 27); EEPROM Clock (GPIO 28) <br> EEPROM - Electrically Erasable Programmable Read-Only Memory |
| 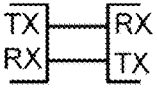 TX—RX RX—TX | Serial Interface 514 <br> TX (GPIO 8); RX (GPIO 10) <br> TX – Transmit and RX – Receive |

FIG. 5

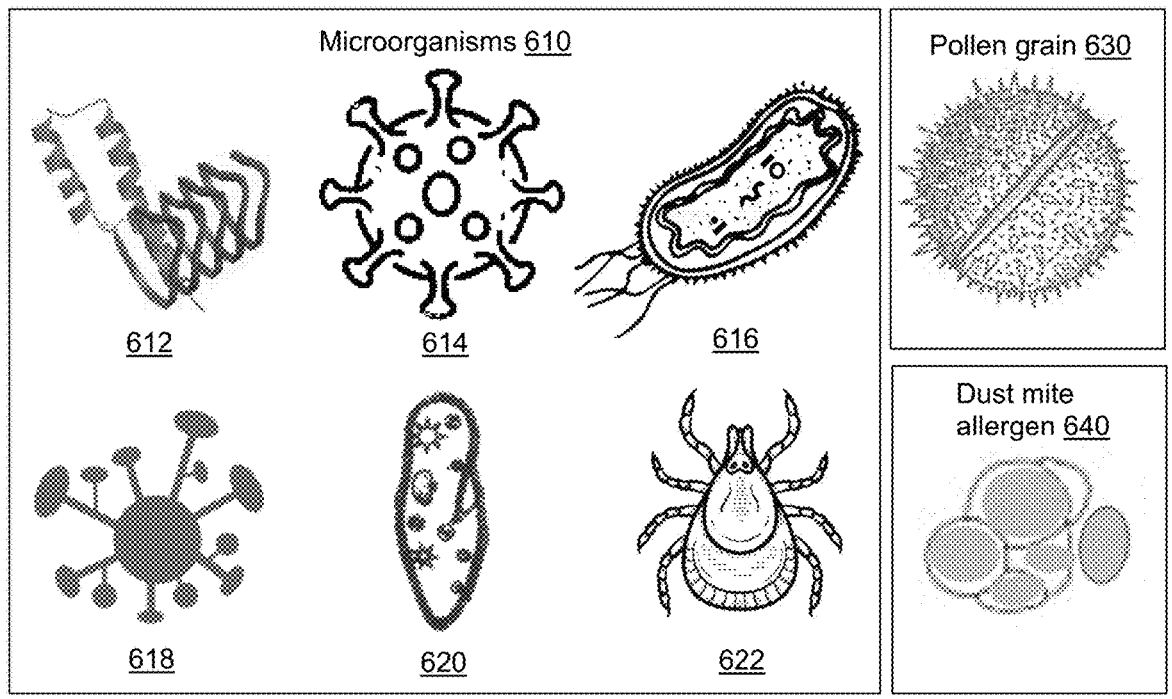
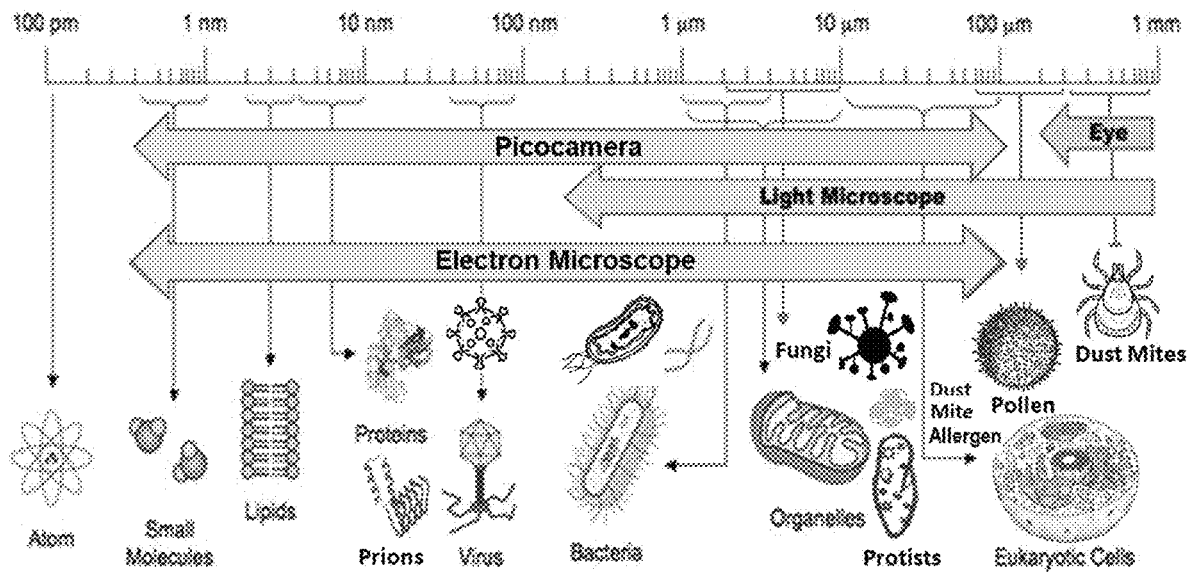
FIG. 6

Prion structure and components diagram 710

Normal prion protein 712

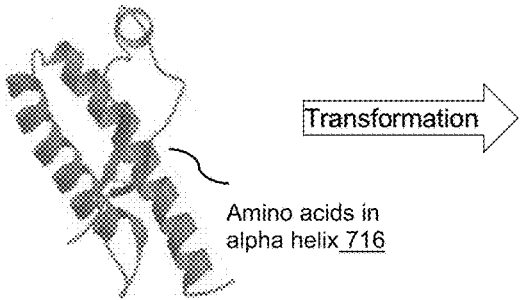

Misfolded prion protein 714

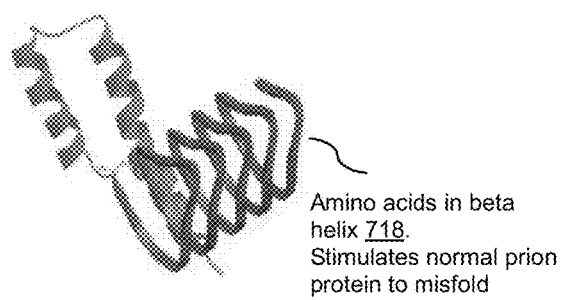

Transformation

Amino acids in alpha helix 716

Amino acids in beta helix 718. Stimulates normal prion protein to misfold

Prion structure components, function, and chemical composition list 730

| Component | Description of Primary Function(s) | Predominant chemical composition |
|---|---|---|
| Amino acids in alpha helix 716 | Normal cellular prion proteins (PrP$^C$) - tiny spherical shape | Amino acids Alpha Helices – 43% Beta Sheet – 3% |
| Amino acids in alpha helix 718 | Pathological Scrapie form of the prion proteins (PrP$^{Sc}$) - usually cube shape | Amino acids Alpha Helices – 30% Beta Sheet - – 43% |

Prion disease, status, and source list 750

| Prion Disease | Status | Source |
|---|---|---|
| Creutzfeldt-Jakob Disease (CJD) - Fatal neurodegenerative disorder due to abnormal isoform of a cellular glycoprotein known as the prion protein. | Noncontagious | Mutations |
| Variant Creutzfeldt-Jakob Disease (vCJD) - Prominent psychiatric/behavioral symptoms - The disease damages brain cells and the spinal cord. This is an infectious type of the disease that is related to "mad cow disease." Eating diseased meat may cause normal human prion protein to develop abnormally. | May be spread from person to person | Animals (Meat) |
| Gerstmann-Straussler-Scheinker Syndrome - Progressive loss of coordination | Noncontagious | Mutations |
| Fatal Familial Insomnia - Rare hereditary disorder causing difficulty in sleeping. There is also a sporadic form of the disease that is not inherited. | Noncontagious | Mutations |

Prion attributes and biosensor detector list 790

| Prion attributes | Amino acids and beta sheet shapes and concentration |
|---|---|
| Biosensor detector | Microbial biosensor, Particulate matter sensor |

FIG. 7

Virus structure and components diagram 810

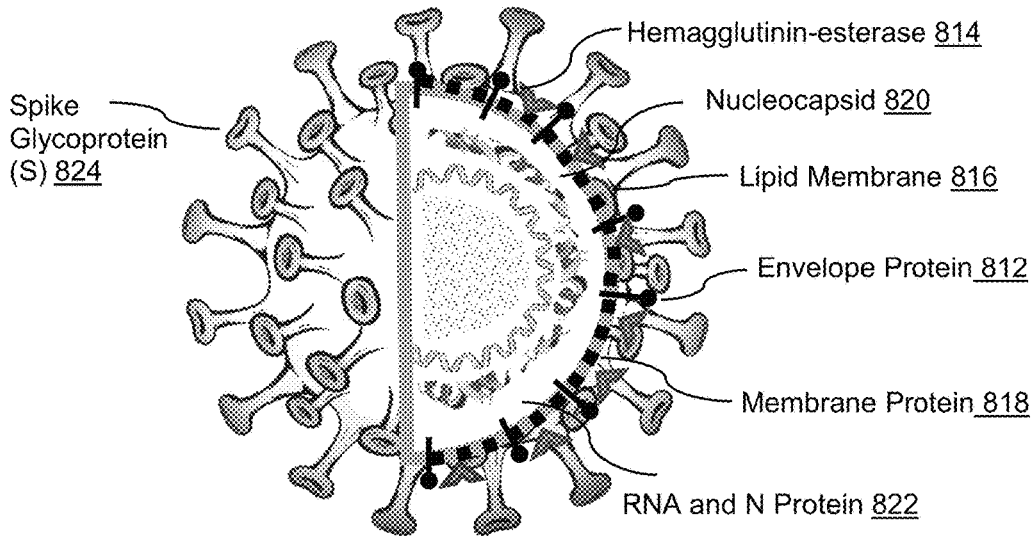

Virus structure components, function, and chemical composition list 830

| Component | Description of Primary Function(s) | Predominant chemical composition |
|---|---|---|
| Envelope Protein 812 | The viral envelope glycoproteins mediate the interaction of the virus with cell receptors and promote the fusion of the viral and cellular membranes during infection of susceptible cell | E-Protein |
| Hemagglutinin-esterase 814 | Glycoprotein that certain enveloped viruses possess and use as invading mechanism | H-Protein |
| Lipid Membrane 816 | Enveloped viruses acquire lipid membranes as their outer coat through interactions with cellular membranes during morphogenesis within, and egress from, infected cells | Phospholipids |
| Membrane Protein 818 | Purpose is to protect the genome-containing virus nucleocapsid from damage, and to facilitate entry of the nucleocapsid into a host cell. | M-Protein |
| Nucleocapsid 820 | Genome plus the protein coat of a virus. The genome is nucleic acid (RNA or DNA) of the virus. The protein coat is its capsid. | N-Protein |
| RNA 822 | The nucleic acid (RNA or DNA) of the virus genome | Mostly RNA |
| Spike Glycoprotein 824 | The S protein plays a role in penetrating host cells and initiating infection. S proteins gives rise to the spike-shaped protrusions found on their surface. | S-Protein |

Percent chemical composition of a virus list 850

| Primary Constituents | Percent of dry weight |
|---|---|
| Protein | 55.0 |
| Carbohydrate | 5 |
| Nucleic Acid / DNA or RNA | 20 |
| Lipid solvents | 15-25% |
| Ionic Environment and pH | Traces |
| Total % | 100% |

FIG. 8

Virus name, disease, status, source, shape, size, and nucleic acid list 1000

| Virus Name | Disease | Status | Source | Shape | Size (nm) | Nucleic Acid |
|---|---|---|---|---|---|---|
| Bacteriophage | Infects bacteria | Non | All | Complex | Head 80x100 L, tail 110 L | DNA or RNA |
| Rabies lyssavirus | Brain | Contagious | Rodents | Bullet | 180 L x 75W | RNA |
| Ebola and Marburg | Hemorrhagic fever | Contagious | Rodents | Filament-ous | 800 L x 80 W | RNA |
| Adenovirus | Colds | Contagious | Humans | Spherical | Polyhedral capsid 70-100 D | DNA |
| Dengue virus | Nausea, vomiting | Non | Mosquito | Spherical | 40–60 D | RNA |
| Hantavirus | Hantavirus | Non | Rodents | Spherical | 120–160 D | RNA |
| Hepatitis B | Liver infection, fever | Contagious | Humans | Spherical | 40–42 D | DNA |
| HIV Virus | AIDS | Contagious | Humans | Spherical | 100–120 D | RNA |
| Influenza A, B | Flu | Contagious | Humans | Spherical | 80–120 D | RNA |
| Norovirus | Vomiting, diarrhea | Contagious | Humans | Spherical | 0.040 D | RNA |
| Zika virus | Birth defects | Non | Mosquito | Spherical | 0,050 D | RNA |
| Rotavirus | Diarrhea, vomiting | Contagious | Humans | Spherical | 70–75 D | RNA |
| SARS-CoV-2 | COVID_19 | Contagious | Humans | Spherical | Polyhedral capsid 80–160 D | RNA |

Virus attributes and biosensor detector list 1090

| Virus attributes | Shape, Size, Structure, DNA/RNA, Chemical Composition |
|---|---|
| Biosensor detector | Microbial biosensor, Particulate matter sensor |

FIG. 10

Bacteria cell structure and components diagram 1110

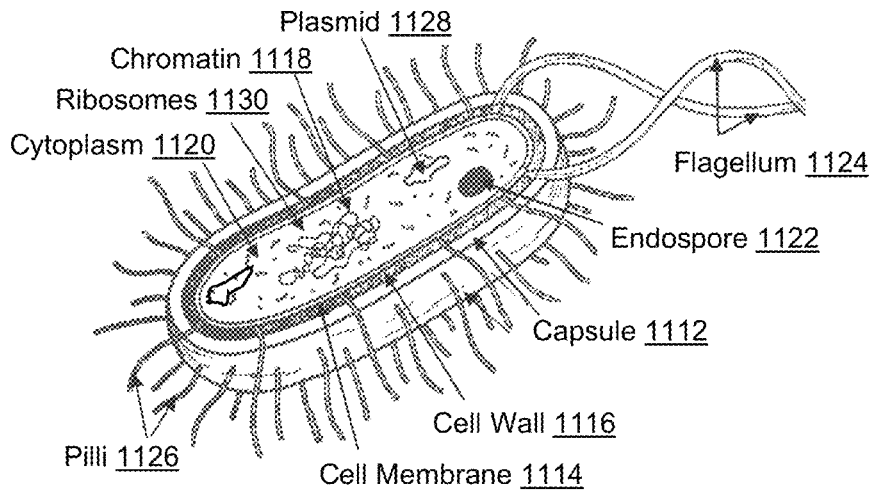

Bacteria cell structure components, function, and chemical composition list 1130

| Component | Description of Primary Function(s) | Predominant chemical composition |
|---|---|---|
| Capsule 1112 | Capsules protects a bacterial cell from ingestion and destruction | Polysaccharide |
| Cell membrane 1114 | Permeability barrier; transport of solutes; energy generation; location of numerous enzyme systems | Phospholipid and protein |
| Cell wall 1116 | Maintain bacterial cell integrity and shape as well as resisting internal turgor pressure | Peptidoglycan (murein) |
| Chromatin 1118 | Genetic material of cell. The DNA of most bacteria is contained in a single circular bacterial chromosome along with proteins & RNA molecules to form nucleoid. | DNA |
| Cytoplasm 1120 | Functions for cell growth, metabolism, and replication | Enzymes, nutrients |
| Endospore 1122 | Produce a dormant and highly resistant cell to preserve the cell's genetic material in times of extreme stress | Dipicolinic acid |
| Flagellum 1124 | Swimming movement | Protein |
| Pilli 1126 | Attachment to surfaces; protection against phagotrophic engulfment | Protein |
| Plasmid 1128 | Extrachromosomal genetic material | DNA |
| Ribosomes 1130 | Sites of translation (protein synthesis) | RNA and protein |

Percent chemical composition of a bacteria list 1150

| Primary Constituents | Percent of dry weight |
|---|---|
| Protein | 55.0 |
| Polysaccharide | 5.0 |
| Lipid | 9.1 |
| DNA | 3.1 |
| RNA | 20.5 |
| Others (sugars, amino acid) | 6.3 |
| Inorganic ions | 1.0 |
| Total % | 100% |
| Cell elements percentage – C (50), O(22), N (12), H (9), P (2), S(1), Na (1), and Traces of Ca, Mg, Cl, Fe elements | |

FIG. 11

Bacteria cell shapes diagram 1200

Spherical (Cocci) 1210

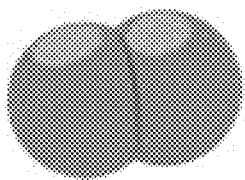
Streptococcus pneumoniae 1212

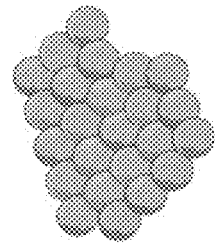
Staphylococcus aureus 1214

Spiral 1220

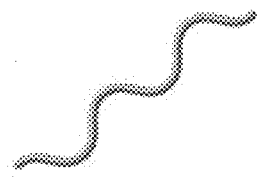
Treponema pallidum 1222

Rod (Bacillus) 1230

Legionella pneumophila 1232

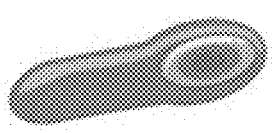
Clostridium botulinum 1234

Streptobacillus moniliformis 1236

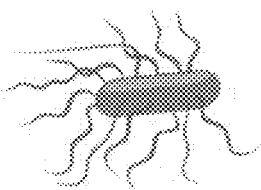
Salmonella typhi 1238

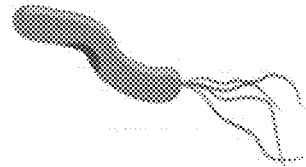
Helicobacter pylori 1240

Comma 1250

Vibrio cholerae 1252

Box 1260

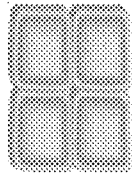
Halophilic 1262

Appendaged 1270

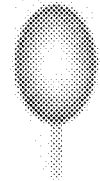
Hyphomicrobium 1272

Pleomorphic 1280

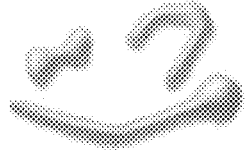
Corynebacterium diphtheria 1282

FIG. 12

Bacteria name, disease, status, source, shape, size, and nucleic acid list 1300

| Bacteria Name | Disease | Status | Source | Shape | Size (µm) | Nucleic Acid |
|---|---|---|---|---|---|---|
| Streptococcus pneumoniae | Pneumonia, otitis media | Contagious | Humans | Spherical (Cocci) | 0.5–1.25 D | DNA |
| Staphylococcus aureus | Opportunistic infections | Endogenous | Humans | Spherical (Cocci) | 0.5–1.5 D | DNA |
| Treponema pallidum | Syphilis | Contagious | Humans | Spiral | 6–20L x 0.2 D | DNA |
| Legionella pneumophila | Pneumonia, Pontiac fever | Non | Env | Rod (Bacillus) | 2–20L x 0.3–0.9 D | DNA |
| Clostridium botulinum | Botulism | Non | Humans | Rod (Bacillus) | 1.2–22 L x 0.5–2 D | DNA |
| Streptobacillus moniliformis | Rat bite fever | Contagious | Rodents | Rod (Bacillus) | 2–5 L x 0.1–0.5 D | DNA |
| Helicobacter pylori | Stomach ulcers or cancer | Contagious | Humans | Rod (Bacillus) | 2–4 L x 0.5–1 D | DNA |
| Salmonella typhi | Infect intestine, blood | Contagious | Humans | Rod (Bacillus) | 2–5 L x 0.5–1.5 D | DNA |
| Vibrio cholerae | Cholera - toxin in intestine | Contagious | Humans | Comma shaped | 2–3 L x 0.5–0.8 D | DNA |
| Halophilic | Biopolymers, biofertilizers | Contagious | Humans | Box | 2.500 | DNA |
| Hyphomicrobium | Drinking water | Contagious | Humans | Append aged | 1.0–3.0 L x 0.3–1.2 D | DNA |
| Corynebacterium diphtheria | Diphtheria | Contagious | Humans | Pleomorphic | 1.5–8.0 L x 0.3–0.6 D | DNA |
| Mycobacterium tuberculosis | Tuberculosis (TB) | Contagious | Humans | Rod (Bacillus) | 2–4 L x 0.2–0.5 D | DNA |
| Streptococcus salivarius | Bacterial meningitis | Contagious | Humans | Spherical (Cocci) | 0.5–2.0 D | DNA |

Bacteria attributes and biosensor detector list 1390

| Bacteria attributes | Shape, Size, Structure, DNA, Chemical Composition, Clusters |
|---|---|
| Biosensor detector | Microbial biosensor, Particulate matter sensor |

FIG. 13

Fungi cell structure and components diagram 1410

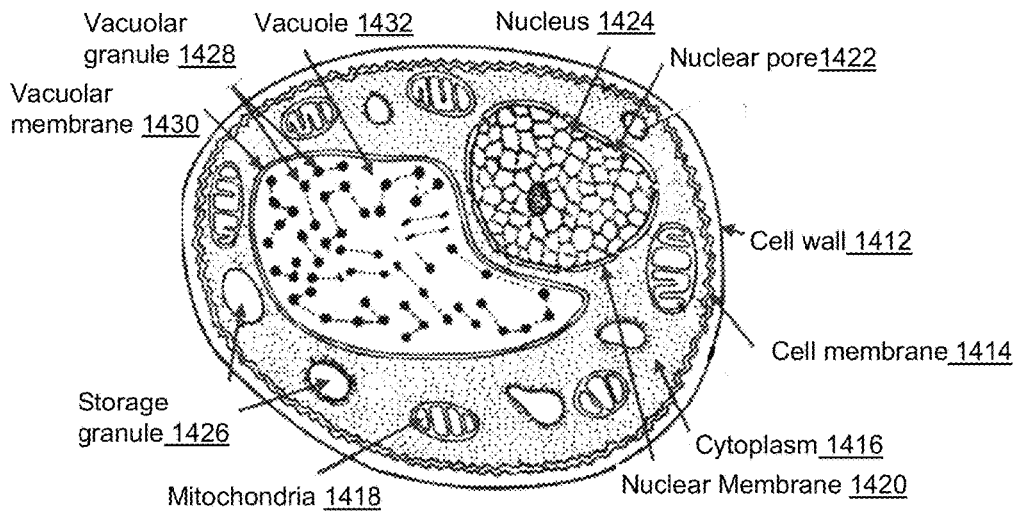

Fungi cell structure components, function, and chemical composition list 1440

| Component | Description of Primary Function(s) | Predominant chemical composition |
|---|---|---|
| Cell membrane 1412 | Allows gases and water to diffuse freely into and out of the cell. Controls the transport of other molecules | Sterols, sphingolipids glycerophospholipids |
| Cell wall 1414 | A layer around the cell membrane of fungi cells made largely of chitin | Chitin |
| Cytoplasm 1416 | Makes enzymes and other proteins | Water, ion, protein |
| Mitochondria 1418 | Contains enzymes for the reactions in aerobic respiration | Phospholipid & proteins |
| Nuclear membrane 1420 | Separates the contents of the nucleus from the rest of the cell. | Lipids |
| Nuclear pore 1422 | Allow the transport of molecules across the nuclear envelope | Nucleoporins |
| Nucleus 1424 | Contains DNA which carries the genetic code for making enzymes | DNA |
| Storage granule 1426 | Store cell energy reserve | Phosphorous & oxygen |
| Vacuolar granule 1428 | Primary storage site for certain small molecules | Polyphosphate |
| Vacuolar membrane 1430 | Separates the contents of the Vacuolar from the rest of the cell. | Lipids |
| Vacuole 1432 | Reservoir for the storage of small molecules (including polyphosphate, amino acids, several divalent cations (e.g., calcium), other ions, and other small molecules) as well as being the primary compartment for degradation | Closed sacs |

Percent chemical composition of a fungi list 1450

| Primary Constituents | Percent of dry weight |
|---|---|
| Fiber | 66–83% |
| Crude Protein | 5.5–13.4% |
| Sugar | 2—5.6% |
| Crude Fat | 0.9–.6% |
| Others | 8–10% |
| Total % | 100% |
| Cell elements – Carbon, hydrogen, and oxygen (as carbohydrates) collectively comprise ~ 45% grams dry weight of a typical yeast cell. | |

FIG. 14

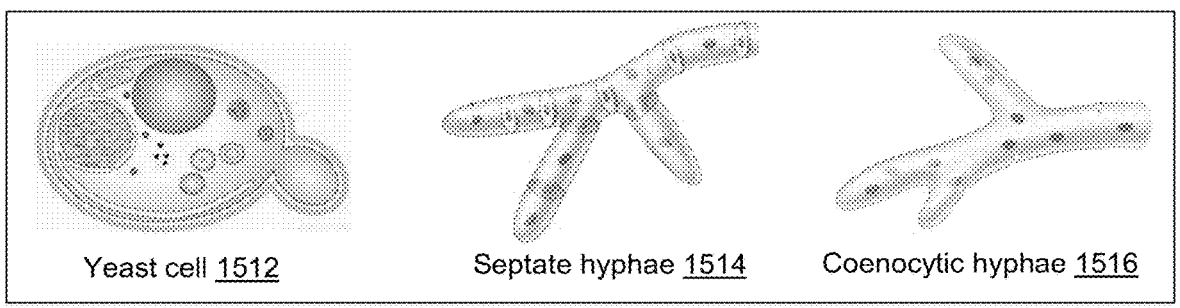
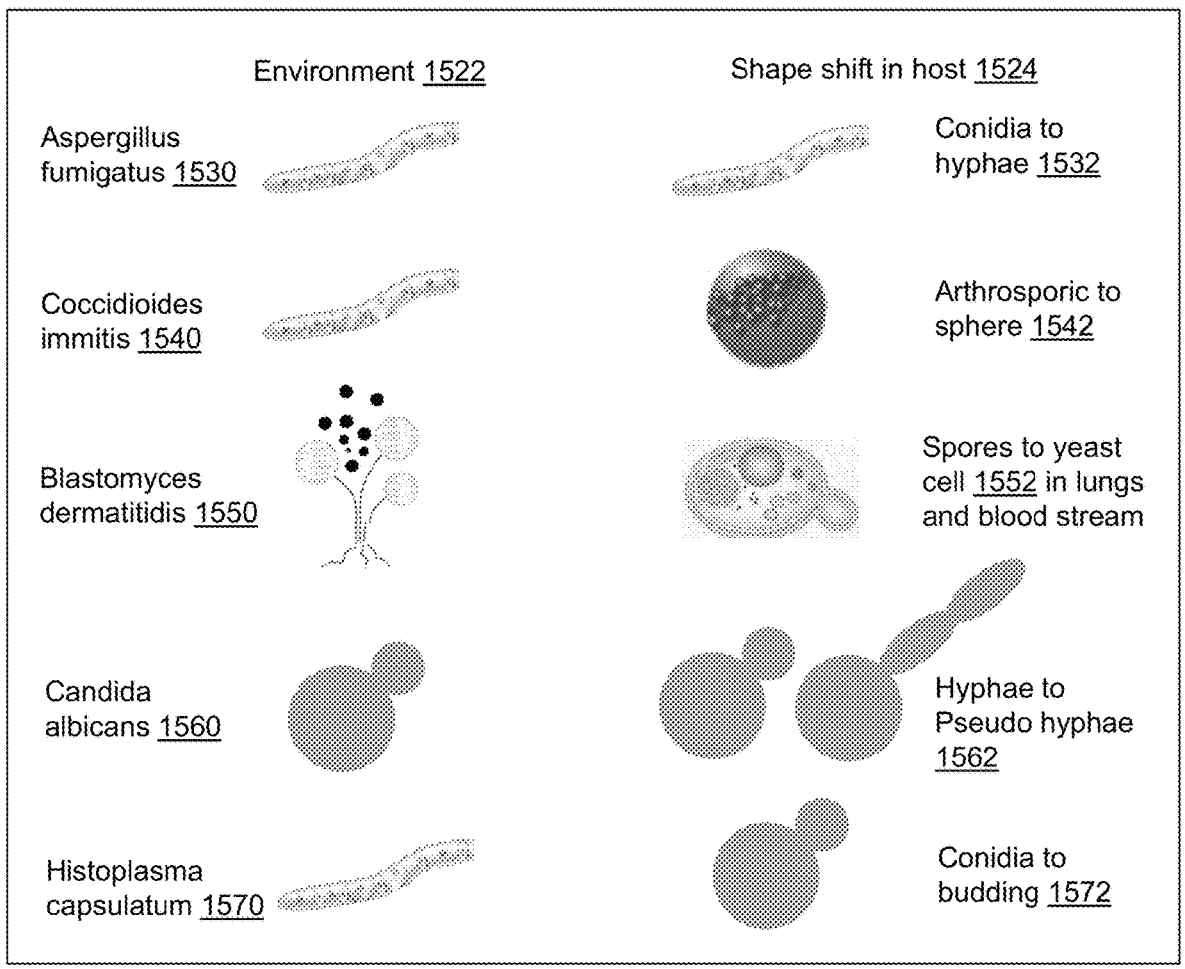
FIG. 15

Fungi name, disease, status, source, shape, size, and nucleic acid list 1600

| Fungi | Disease | Status | Source | Shape | Size (μm) | Nucleic Acid |
|---|---|---|---|---|---|---|
| Aspergillus flavus | Aspergillosis | Non | Env | Aspergillum Hyphae | 2.0–3.5 D | DNA |
| Aspergillus fumigatus | Aspergillosis | Non | Env | Aspergillum Hyphae | 2.0–3.5 D | DNA |
| Blastomyces dermatitidis | Blastomycosis | Non | Env | Spherical | 1.5–2.0 D | DNA |
| Coccidioides immitis | Coccidioido mycosis | Non | Env | Barrel shaped | 30–100 D | DNA |
| Candida albicans | Nonrespiratory | Non | Env | Spherical | 10–12 D | DNA |
| Cryptococcus albidus | Allergen | Non | Env | Spherical | Ovoid 2–5 x 3–7 | DNA |
| Cryptococcus laurentii | Allergen | Non | Env | Spherical | Ovoid 2–5 x 3–7 | DNA |
| Cryptococcus neoformans | Cryptococcosis | Non | Env | Spherical | Ovoid 2–5 x 3–7 | DNA |
| Histoplasma capsulatum | Histoplasmosis | Non | Env | Hyphae | 2–4 D | DNA |
| Stachybotris atra | Allergic alveolitis | Non | Env | Bottle shaped | 9–14 L | DNA |
| Stachybotris chartarum | Allergic alveolitis | Non | Env | Bottle shaped | 9–14 L | DNA |
| Trichophyton | Athlete's foot, mouth, throat, esophagus | Non | Env | Spherical | 8–50 L | DNA |
| Microsporum | Athlete's foot, mouth, throat, esophagus | Non | Env | Spherical | Obvate 7–20 x 30–160 | DNA |
| Epidermo phyton | Athlete's foot, mouth, throat, esophagus | Non | Env | Spherical | 20–40 L x 7–12 W | DNA |

Fungi attributes and biosensor detector list 1690

| Fungi attributes | Shape, Size, Structure, DNA, Chemical Composition in the environment and in the host |
|---|---|
| Biosensor detector | Microbial biosensor, Particulate matter sensor |

FIG. 16

Protist cell structure and components diagram 1710

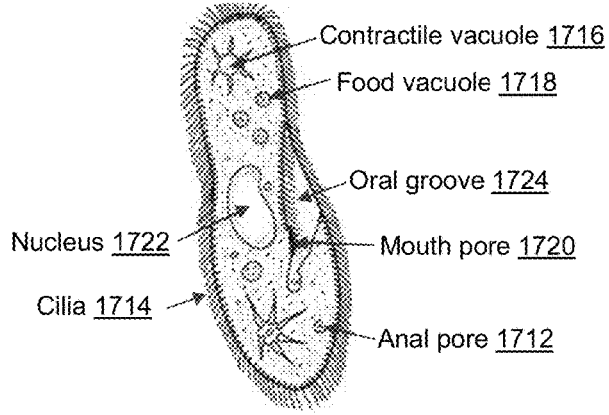

Protist cell structure components, function, and chemical composition list 1750

| Component | Description of Primary Function(s) | Predominant chemical composition |
|---|---|---|
| Anal pore 1712 | Ejection of waste is ejected after the nutrients from food have been absorbed | Piles of fibers, and microtubules |
| Cilia 1714 | Move water across the cell and contribute to both locomotion and food capture | Protein tubulin |
| Contractile vacuole 1716 | Controls the intracellular water balance by accumulating and expelling excess water out of the cell, allowing cells to survive under hypotonic stress. | Closed sacs |
| Food vacuole 1718 | Storing food which has been absorbed by the organism | Polyphosphate |
| Mouth pore 1720 | Draw and prey organisms inside the mouth opening using Celia | Oral groove protein |
| Nucleus 1722 | Protects DNA, which is the blueprint or code that runs every function of protist cell | DNA |
| Oral groove 1724 | It is used to capture and digest bacteria. | Protein |

Protists, disease, source, shape, size, and nucleic acid list 1780

| Protists | Disease | Status | Source | Shape | Size (μm) | Nucleic Acid |
|---|---|---|---|---|---|---|
| Paramecium | Ingest, kill the cells of the human pathogenic fungus Cryptococcus neoformans | Non | Water | Elongated | 50–300 L | DNA |
| Trypanosoma protozoa | Sleeping sickness | Non | Fly/Bug | Spindle | 16–42 L X 1–3 W | DNA |
| Plasmodium | Malaria spread by mosquito vector | Non | Mosquito | Crescent shaped | 1.5 L x 1 to 20 W | DNA |
| Giardia | Diarrhea and stomach cramps. Fecal /Oral Transfer | Contagious | Humans / Water | Pear Shaped | 12–15 L x 5–10 W | DNA |

Protist attributes and biosensor detector list 1790

| Protist attributes | Shape, Size, Structure, DNA, Chemical Composition |
|---|---|
| Biosensor detector | Microbial biosensor, Particulate matter sensor |

FIG. 17

Dust mite structure and components diagram 1810

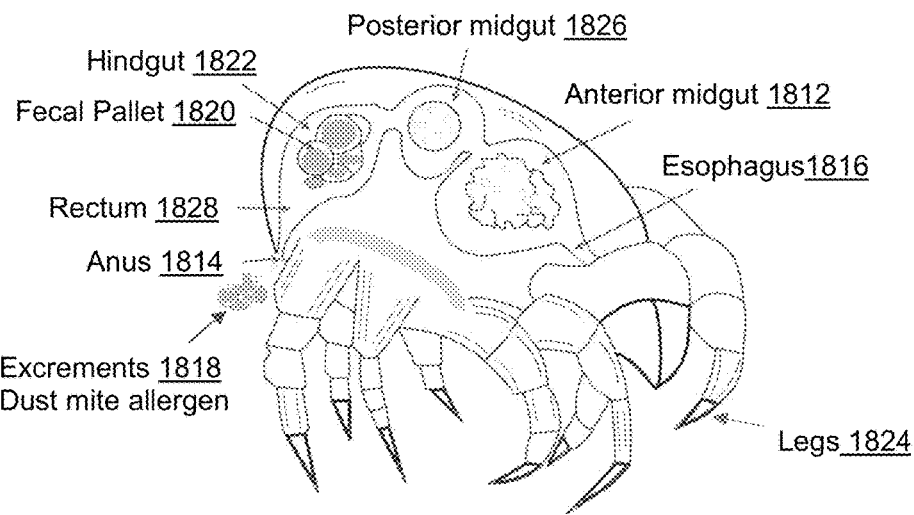

Dust mite structure components, function, and chemical composition list 1850

| Component | Description of Primary Function(s) |
| --- | --- |
| Anterior midgut 1812 | Products of digestion to pass through the gut |
| Anus 1814 | Discharge of excrements |
| Esophagus 1816 | Transport material from the mouth to anterior midgut |
| Excrements 1818 | Excrements are considered the main source of allergy. Consists of protein / digestive enzymes |
| Fecal Pallet 1820 | Reservoir containing excrements |
| Hindgut 1822 | The hindgut is the posterior part of the digestive system |
| Legs 1824 | There are eight legs for the movement |
| Posterior midgut 1826 | Part of the digestive track responsible for physiological regulation such as metabolism, |
| Rectum 1828 | Receive fecal pallet from the hindgut |

Dust mite attributes and biosensor detector list 1890

| Dust mite attributes | Shape, Size, Structure, DNA, Chemical Composition |
| --- | --- |
| Biosensor detector | Microbial biosensor, Particulate matter sensor |

FIG. 18

Virus, bacteria, and fungi attributes comparison list 1900

| Attributes | Virus | Bacteria | Fungi |
|---|---|---|---|
| Size | Small. Most viruses diameter is from 20 nm to 250–400 nm. Largest measure about 500 nm in diameter & are about 700–1,000 nm in length | Medium. Most common bacteria are about 1 to 2 μm in diameter and 5 to 10 μm long | Large. Most small fungi are 2-10 μm in diameter and several tenths of an inch in length. The average size of fungi hyphae is 5-50 μm in length |
| Organism Type | Non-Living - Intercellular organisms | Prokaryotic - Intercellular organisms | Eukaryotes - Either unicellular or multi-cellular |
| Shape | icosahedral or helical capsid. Usually rod & filament shape | Spherical or oval, rod, spiral | Mass of hyphae |
| Color | Smaller than light particles, using electron microscope it reveals grey color | Usually white, red, purple, yellow, and blue green | Usually red, purple, yellow, brown, orange, and green |
| Cell membrane | No cell membrane. Many viruses are surrounded by a continuous bilayer membrane studded with viral proteins | Cell membrane below the cell wall | Have a cell membrane |
| Genetic Material | DNA and RNA | DNA | DNA |
| Host | Needs a living host, like a plant or animal. | Can grow on non-living surfaces | Can live on its own |
| Mobility | Viruses do not have structures and thus cannot move on their own | There are several types of bacteria movements | Typically, fungi are non-mobile organisms |
| Reproduction | Virus enters the host cell, makes a copy of itself, and causes the cell to burst | Reproduce by splitting into two cells | Reproduction can take place in multiple ways |
| Living | Characteristics of both living and non-living | Yes | Yes |
| Energy Sources | Get materials and energy from host cells | Get energy from the same sources as humans | Use pre-existing carbon sources in their environment and energy from chemical reactions |
| Usefulness | Mostly are harmful | Some bacteria can be useful | Many fungi are beneficial |
| Transmission Mode | Airborne, touch, body fluid, contaminated objects, insects, animals | Air, water, food, touch, body fluid or living vector | Air and touch |
| Example Infection | Common cold, Influenza, COVID-19, food poisoning | Dental, post-surgery, food poisoning | Athlete's foot, vaginal yeast infection, ringworm |
| Treatment | Vaccines, antiviral drugs, and over the counter products to manage symptoms | Antibiotics and over the counter products to manage symptoms | Antifungal medication and over the counter products to manage symptoms |
| Prevention | Good hygiene, wear a mask, and vaccines | Good hygiene, keep wounds clean and covered | Good hygiene, keep the skin clean, and wear masks. |

FIG. 19

Platform dataset 2010

| No | Platform Dataset Resources |
|----|---------------------------|
| 1 | National Center for Biotechnology Information (NCBI) |
| 2 | European Molecular Biology Laboratory/ European Bioinformatics Institute (EMBL-EB) |
| 3 | MicrobeNet - Centers for Disease Control and Prevention (CDC) |
| 4 | Pathosystems Resource Integration Center (PATRIC) |
| 5 | Prion disease database – NCBI, CDC |
| 6 | Virus Pathogen Resources (ViPR) |
| 7 | Bacterial genomes – Wellcome Sanger Institute |
| 8 | Fungi Database (FungiDB) |
| 9 | Pathogenic Protist database, ,Dust mite database |
| 10 | Ensembl genome browser provides access to organized information from the analysis of biological data for virus, bacteria, and fungi |
| 11 | Pollen data from National Centers for Environmental Information and Global Pollen Project |
| 12 | Allergens and isoallergens/variants – CDC, WHO/IUIS-Allergen, Allergome, AllergenOnline, GenBank, GenPept, UniProtKB, PDB, PubMed, and others |

Microorganism taxonomy 2050

| Virus Taxonomy | | Kingdom | *Orthornavirae* –Domain - *Duplodnaviria,Monodnaviria.* | | |
|---|---|---|---|---|---|
| Phylum | Class | Order | Family | Genus | Species |
| *Pisuviricota* | *Pisoniviricetes* | *Nidovirales* | *Coronaviridae* | *Betacoronavirus* | *SARS-coronavirus* |
| *Negarnaviricota* | *Insthoviricetes* | *Articulavirales* | *Orthomyxoviridae* | *Alphainfluenzavirus* | *Influenza A virus* |

| Bacteria Taxonomy | | Kingdom | *Bacteria /Eubacteria /Monera* - Domain - *Prokaryotic* | | |
|---|---|---|---|---|---|
| Phylum | Class | Order | Family | Genus | Species |
| *Firmicutes* | *Bacilli* | *Bacillales* | *Staphylococcaceae* | *Staphylococcus* | *Staphylococcus aureus* |
| *Proteobacteria* | *Gammaproteo bacteria* | *Legionellales* | *Legionellaceae* | *Legionella* | *Legionella pneumophila* |

| Fungi Taxonomy | | Kingdom | *Fungi* - Domain - *Eukaryotic* | | |
|---|---|---|---|---|---|
| Phylum | Class | Order | Family | Genus | Species |
| *Ascomycota* | *Eurotiomycetes* | *Eurotiales* | *Trichocomaceae* | *Aspergillus* | *Aspergillus flavus* |
| *Ascomycota* | *Eurotiomycetes* | *Onygenales* | *Ajellomycetaceae* | *Blastomyces* | *Blastomyces dermatitidis* |

| Protist Taxonomy | | Kingdom | *Protista* - Domain - *Eukaryotic* | | |
|---|---|---|---|---|---|
| Phylum | Class | Order | Family | Genus | Species |
| *Paramecium aurelia* | *Oligohymenophorea* | *Peniculida* | *Parameciidae* | *Paramecium* | *Paramecium biaurelia* |

| Dust mite Taxonomy | | Kingdom | *Animalia* - Domain - *Uniramia, Crustacea, Chelicerata* | | |
|---|---|---|---|---|---|
| Phylum | Class | Order | Family | Genus | Species |
| *Arthropoda* | *Arachnida* | *Sarcoptiformes* | *Pyroglyphidae* | *Dermatophagoides* | *Dermatophagoides farinae* |

FIG. 20

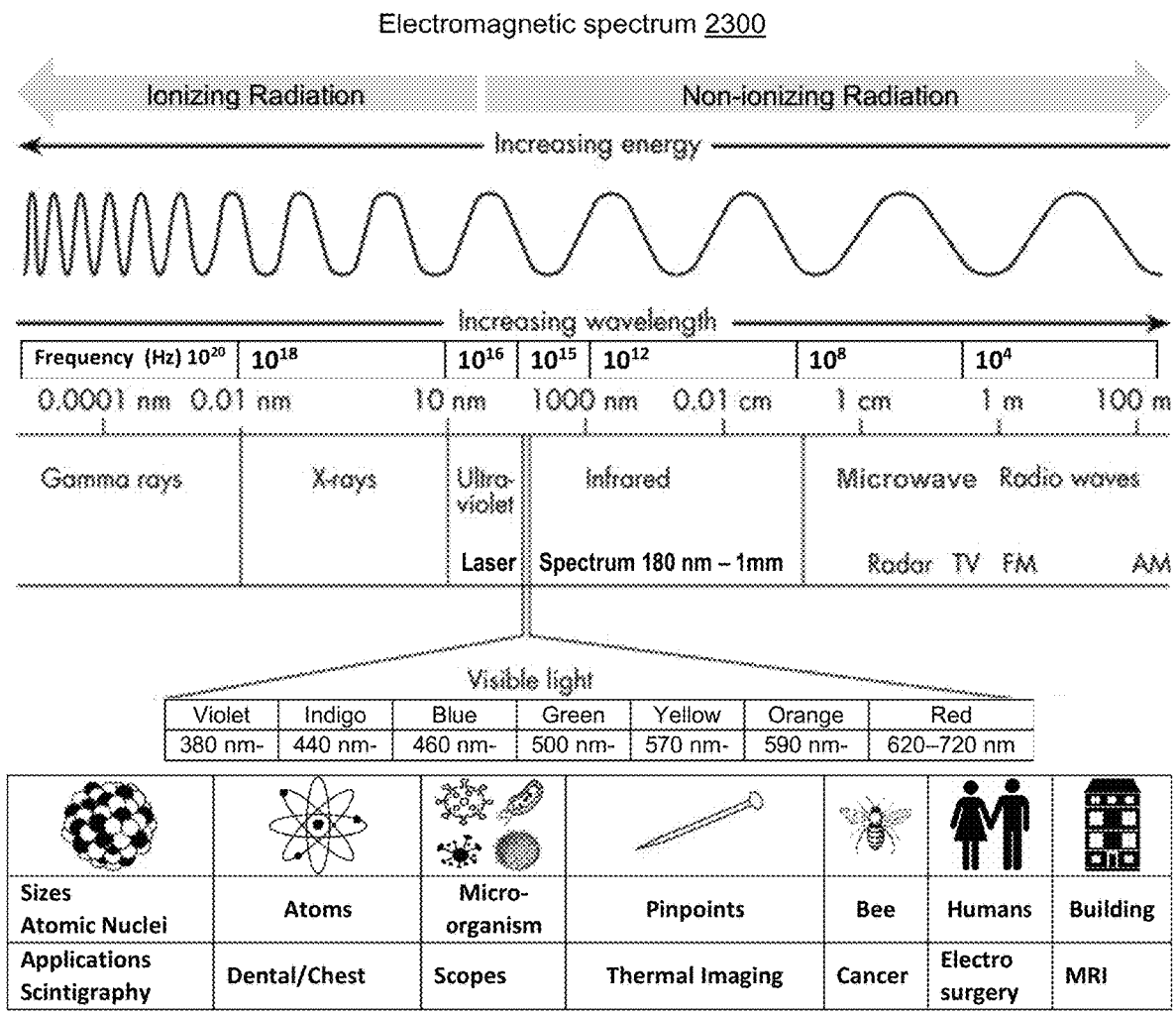
FIG. 23

Noninvasive biosensors for particle detection, and sterilization list 2410

| Microorganism Detected | Biosensor Detector | Type of Biosensor / Transducer | Measurement Condition | Particle Detection Method |
|---|---|---|---|---|
| Prions, viruses, bacteria, fungi, protists, dust mites | Microbial biosensor | Optical, Mass based, Ultrasound waves | Nasal cavity, Oral cavity, Surface | Optical – Infrared spectroscopy, Fluorescence Imaging, Particle Imaging Nucleic acid sequence identification Mass based – Electromagnetic waves Ultrasound waves – Acoustic waves |
| Prions, viruses, bacteria, fungi, protists, dust mites, pollen grains, dust mite allergens | Particulate matter sensor | Laser scattering and imaging | Environment air | Light scattering and imaging Particle Imaging Nucleic acid sequence identification |
| Prions, viruses, bacteria, fungi, protists, dust mites | Microbial biosensor sterilizer | Heat; Ultraviolet light; magnetic, Acoustic wave, amplitude; wavelength, and phase | Nasal cavity, Oral cavity, Surface | Heat, Ultrasound, Acoustic wave, Ultraviolet light to kill microorganism |

Picomaterials 2450

Picoparticle 2452    Picotube 2454    Picofiber 2456    Picorod 2458

 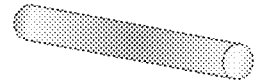  

Particle detection methods working principle list 2490

| No | Particle Detection Method | Microorganisms Attributes Unique Identifier |
|---|---|---|
| 1 | Infrared spectroscopy – Shining infrared light on the object and measuring infrared absorption, transmission, reflectance wavelength signal specific to microorganism cell chemicals | Cell structure components and chemical composition |
| 2 | Fluorescence imaging – Taking pictures of the radiation emitted by the microorganisms because of incident radiation of certain wavelength | Shape, size, color, cell structure components, chemical composition |
| 3 | Particle Imaging – High magnification and resolution images of microorganisms using picomaterials followed by pattern recognition and classification | Shape, size, color, cell structure components |
| 4 | Nucleic acid sequence identification – High resolution image of nucleic acid and identification of unique DNA and RNA sequence segments | Unique DNA and RNA sequence segments |
| 5 | Electromagnetic waves – Detects the changes in magnitude of a magnetic field of the microorganisms containing ferromagnetic materials using the Hall effect | Cell ferromagnetic materials composition |
| 6 | Light scattering and imaging – Analysis of reflection pattern of incident laser light from the outer surface of microorganism, pollen, and dust mite allergens | Cell structure components and chemical composition |
| 7 | Ultrasound waves and sound – Directing sound waves towards a surface and measuring the reflected echoes. Echoes are different depending on the density of the microorganism that the ultrasound waves hit. Acoustic reporter gene to scatter sound waves coupled with cell structure high resolution imaging technique. Listening to unique sound of one microorganism through picotube microphone. | Cell structure components and chemical composition, Gas filled nanostructure vesicles |

FIG. 24

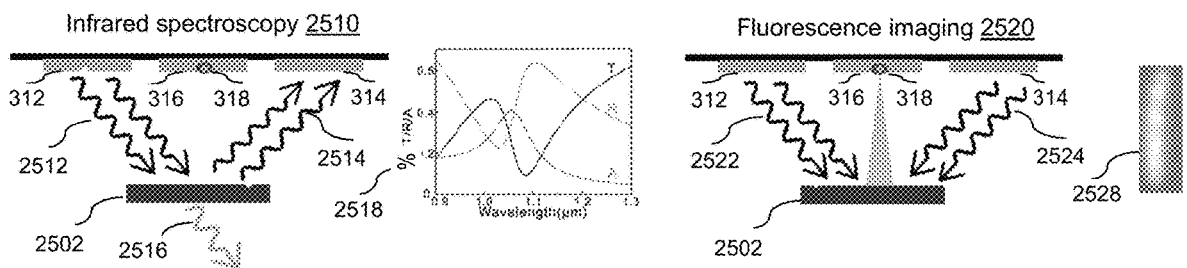
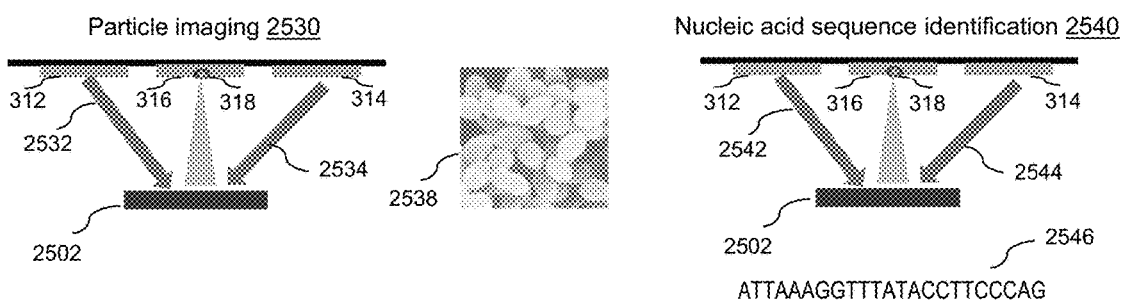
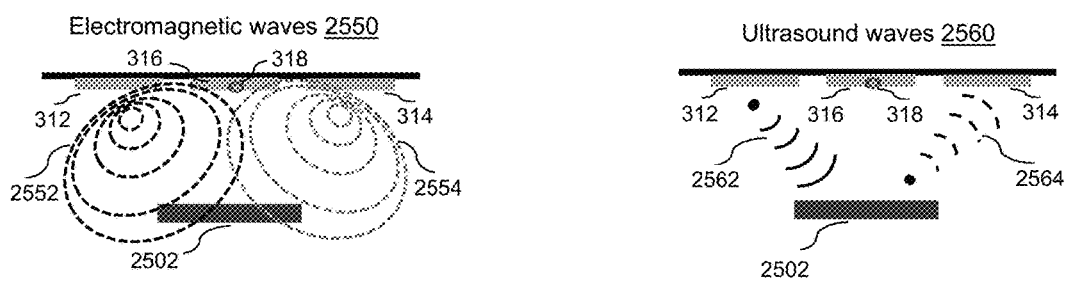
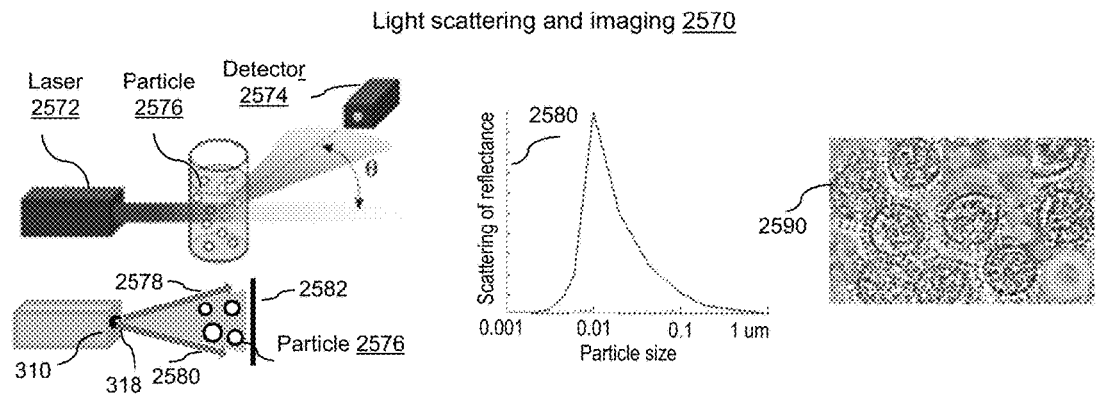
FIG. 25

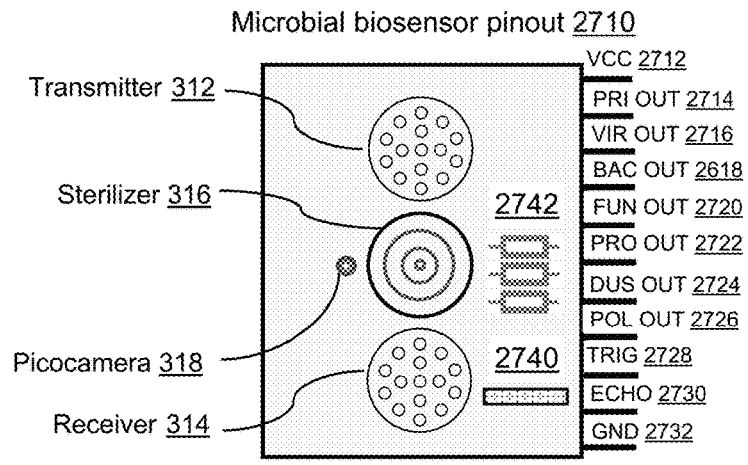

Microbial biosensor pinout 2710

Microbial biosensor wiring table 2750

| Microbial biosensor pinout | Microbial biosensor pin function | Steps to wire a Microbial biosensor pin to the SBC GPIO pin |
|---|---|---|
| VCC 2712 | VCC 2712 pin is used as positive power supply. | Connect microbial biosensor VCC 2712 pin to the assigned SBC GPIO pinout 370 5V power pin. |
| PRI OUT 2714 | PRI OUT 2714 pin is used as output pin for pion. | Connect microbial biosensor PIR OUT 2714 pin to the assigned SBC GPIO pinout 370 pin. |
| VIR OUT 2716 | VIR OUT 2716 pin is used as output pin for virus. | Connect microbial biosensor VIR OUT 2716 pin to the assigned SBC GPIO pinout 370 pin. |
| BAC OUT 2718 | BAC OUT 2718 pin is used as output pin for bacteria. | Connect microbial biosensor BAC 2718 pin to the assigned SBC GPIO pinout 370 pin. |
| FUN OUT 2720 | FUN OUT 2720 pin is used as output pin for fungi. | Connect microbial biosensor FUN OUT 2720 pin to the assigned SBC GPIO pinout 370 pin. |
| PRO OUT 2722 | PRO OUT 2722 pin is used as output pin for protists. | Connect microbial biosensor PRO OUT 2722 pin to the assigned SBC GPIO pinout 370 pin. |
| DUS OUT 2724 | DUS OUT 2724 pin is used as output pin for dust mites. | Connect microbial biosensor DUS OUT 2724 pin to the assigned SBC GPIO pinout 370 pin. |
| POL OUT 2726 | POL OUT 2726 pin is used as output pin for pollen grains and dust mite allergens | Connect microbial biosensor POL OUT 2726 pin to the assigned SBC GPIO pinout 370 pin. |
| TRIG 2728 | TRIG 2728 pin is used to trigger the signal pulses such as light or sound | Connect microbial biosensor TRIG 2728 pin to the assigned SBC GPIO pinout 370 TRIG pin. |
| ECHO 2730 | ECHO 2730 pin produces a pulse when the reflected signal is received. | Connect microbial biosensor ECHO 2730 pin to the assigned SBC GPIO pinout 370 TRIG pin. |
| GND 2732 | GND 2732 pin is used as negative power ground. | Connect microbial biosensor GND 2732 pin to the assigned SBC GPIO pinout 370 GND pin. |
| Camera CSI port 2740 | Camera CSI port 240 is used as an electrical bus. | Connect camera CSI port 2740 to the SBC Camera CSI port 368. |

FIG. 27

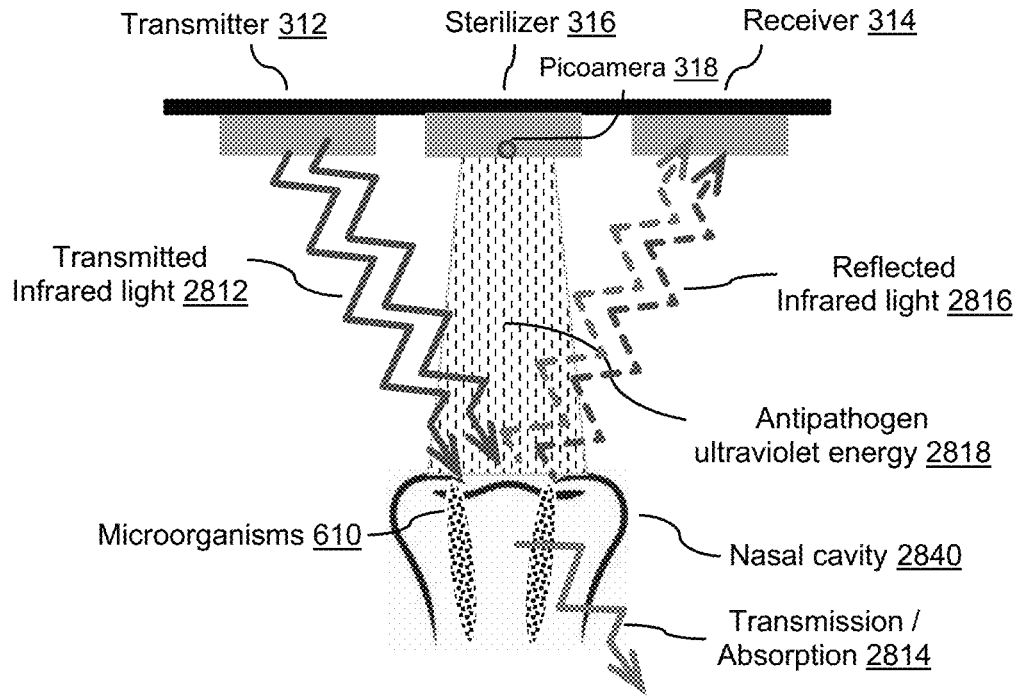
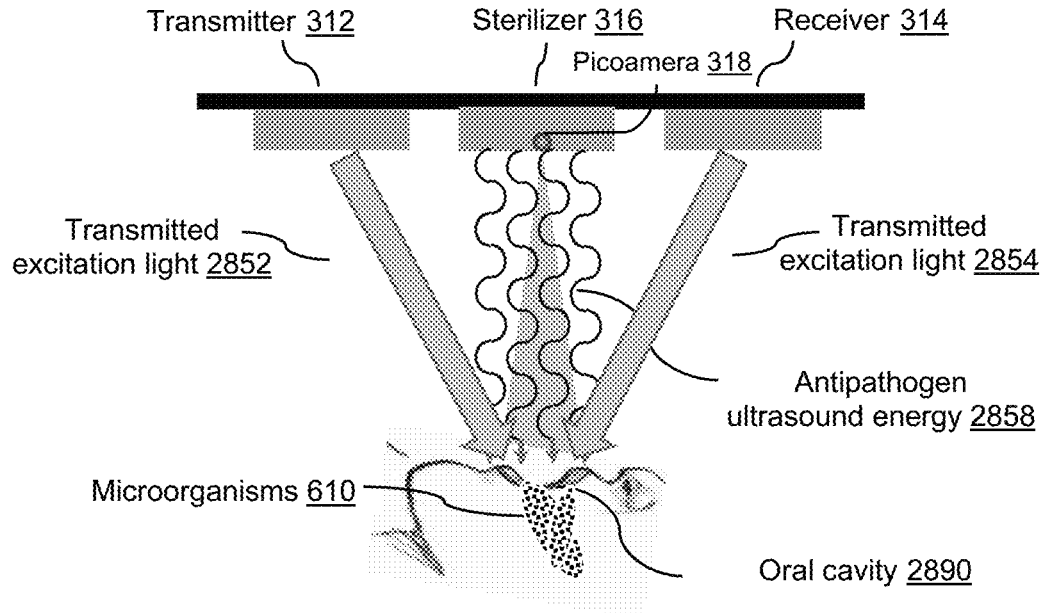
FIG. 28

Microbial biosensor nasal cavity test method diagram 2910
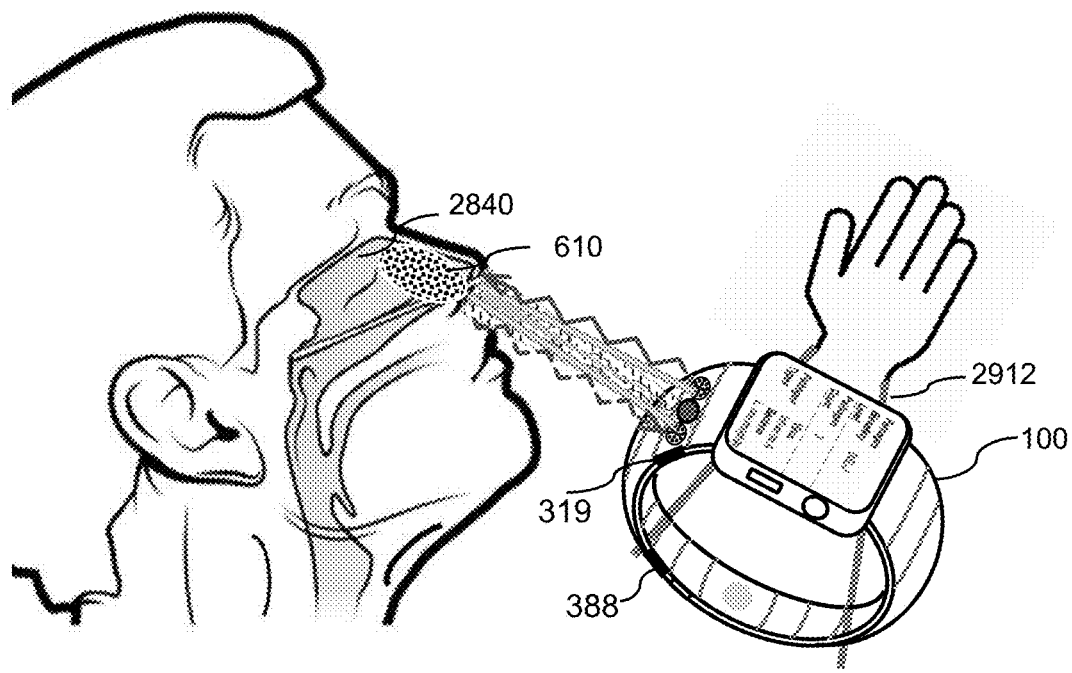
Microbial biosensor oral cavity test method diagram 2950
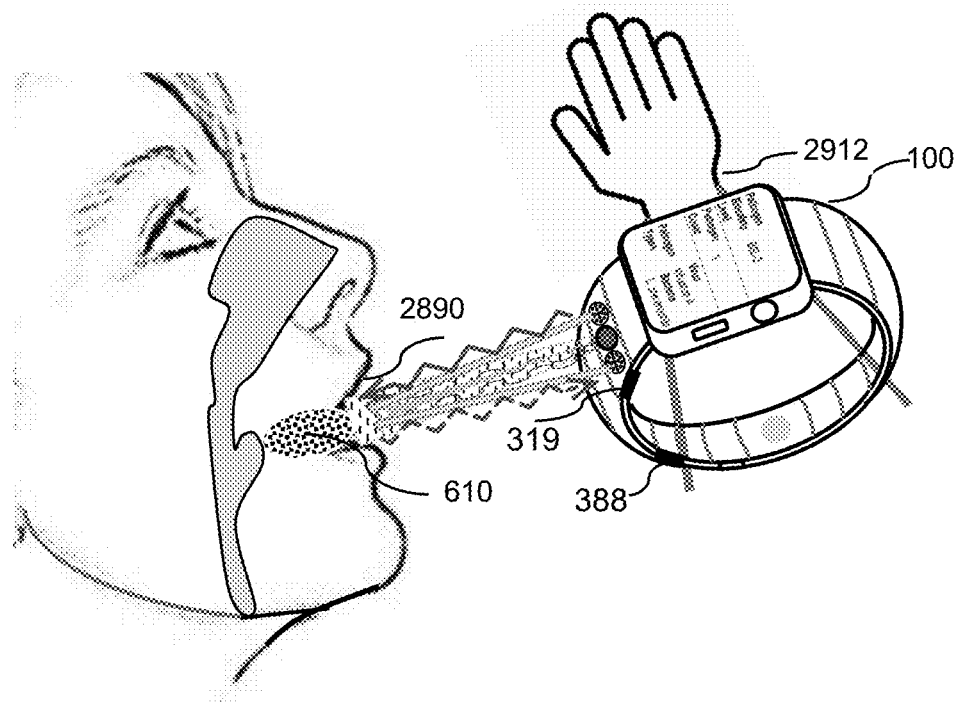
FIG. 29

Microbial biosensor surface test method diagram 3010
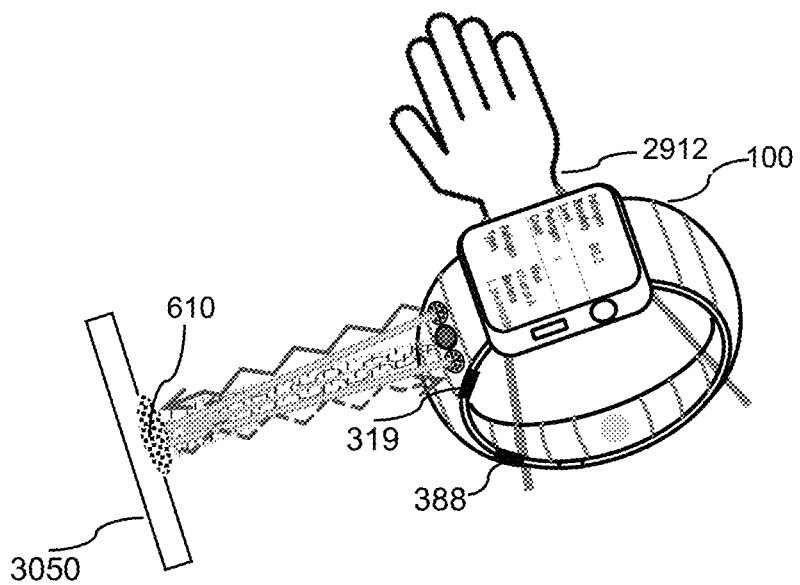
Surface 3050
Drinks 3052
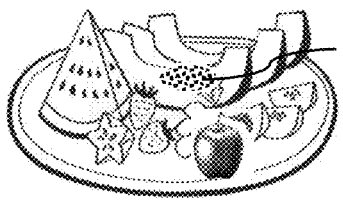
Food 3054
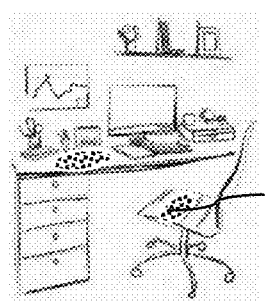
Furniture 3056
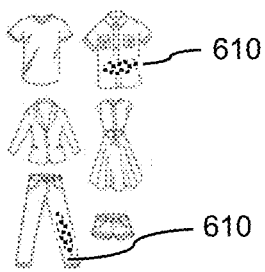
Clothes 3058
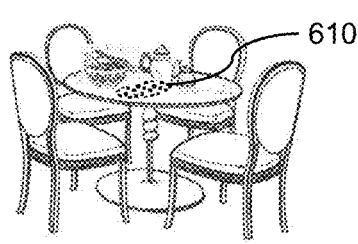
Dining Table 3060
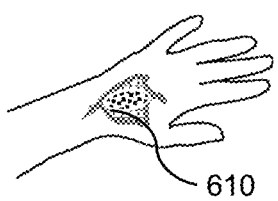
Skin Infection 3062
FIG. 30

Pollen grain diagram 3110

Pollen grain structure and components diagram 3150

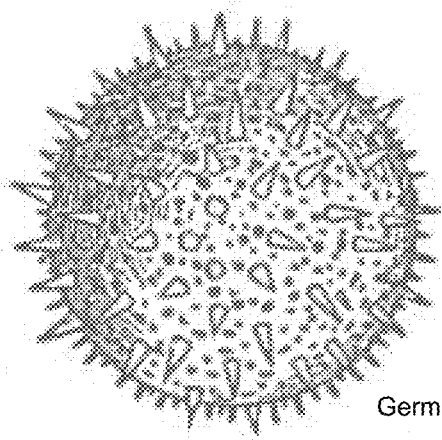
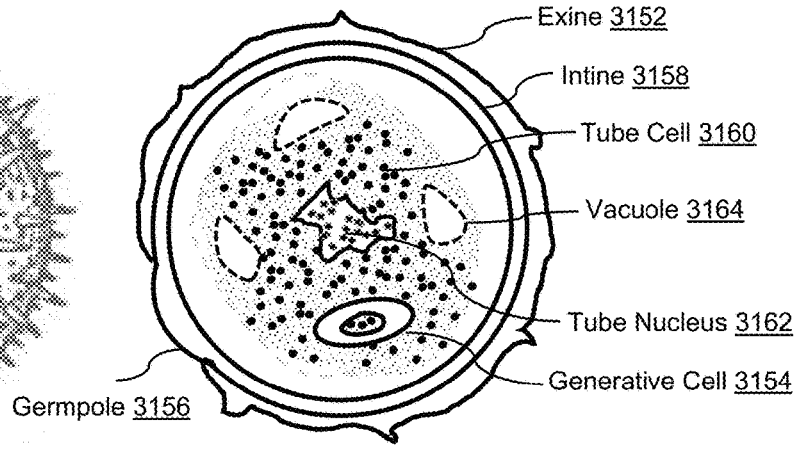

Germpole 3156

Pollen structure components, function, and chemical composition list 3170

| Component | Description of Primary Function(s) | Predominant chemical composition |
|---|---|---|
| Exine 3152 | Decay-resistant outer coating of a pollen grain or spore. It bears a characteristic surface pattern that is used in palynology | Cellulose and pectins. |
| Generative Cell 3154 | A reproductive cell, especially a cell of an angiosperm pollen grain that divides to produce two male gamete nuclei | Sperm nuclei |
| Germpole 3156 | A pore, pit, or thin area in the outer wall of a spore or pollen grain through which the germ tube or pollen tube makes its exit on germination | Cellulose and pectins |
| Intine 3158 | It is essential for the maturation of the pollen grain and pollen tube germination | Cellulose and pectins. |
| Tube Cell 3160 | The cell in the pollen grain that develops into the pollen tube (the tube which conveys the male gametes of seed-bearing plants to the ovule). | Cellulose and pectins |
| Tube Nucleus 3162 | Nuclei formed by mitotic division of a microspore during the formation of a pollen grain that is held to control subsequent growth of the pollen tube & that does not divide again | Cellulose and pectins |
| Vacuole 3164 | A space within a cell that is empty of cytoplasm, lined with a membrane filled with fluid | Water / inorganic and Organic molecule |

Percent chemical composition of an air-dried pollen list 3190

| Primary Constituents | Percent of dry weight |
|---|---|
| Proteins | 22.7 – 32.8% |
| Amino Acids | 10.4 – 11.5% |
| Reducing Sugars | 36.5 – 40.7% |
| Sucrose | 3.7% |
| Lipids | 7.3 – 12.8% |
| Others | 4.0% |
| Total % | 100% |

FIG. 31

Pollen grain shapes diagram 3200
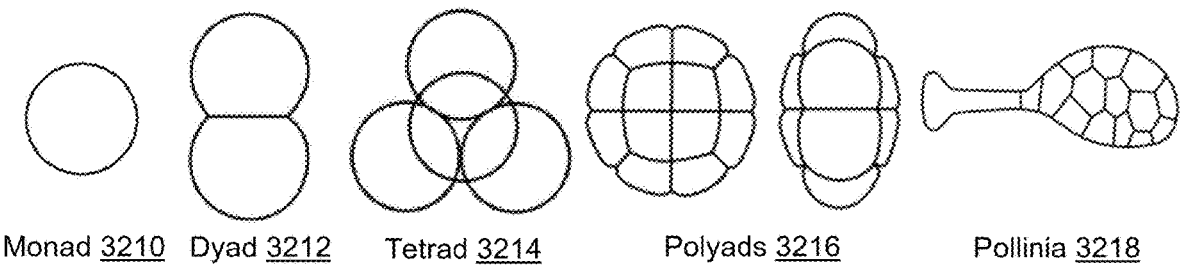
Monad 3210   Dyad 3212   Tetrad 3214   Polyads 3216   Pollinia 3218
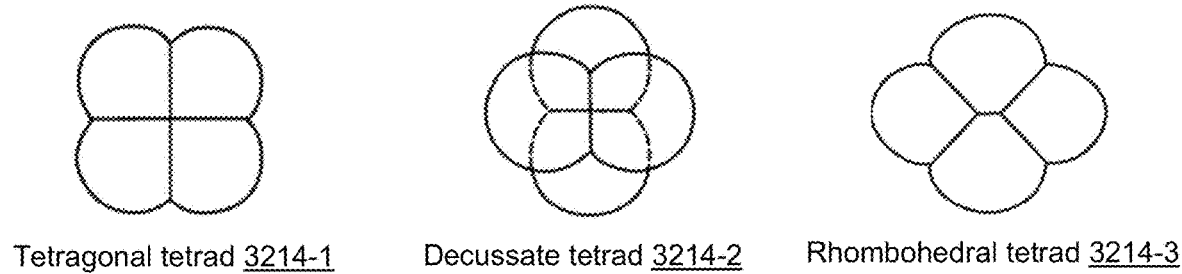
Tetragonal tetrad 3214-1   Decussate tetrad 3214-2   Rhombohedral tetrad 3214-3
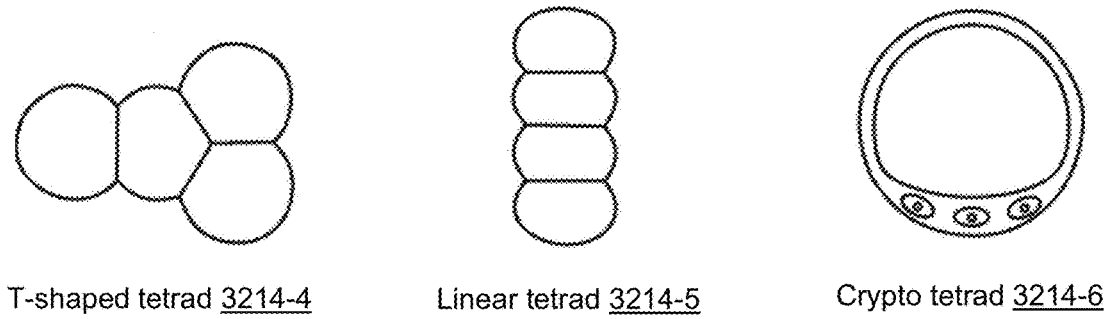
T-shaped tetrad 3214-4   Linear tetrad 3214-5   Crypto tetrad 3214-6
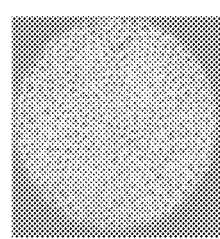 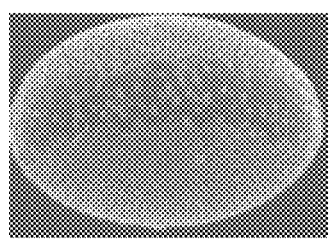 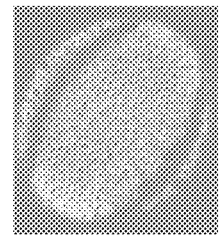
Single grains without apertures 3230   Single grains with furrows 3240   Single grains with apertures 3250
FIG. 32

Pollen type source, name, disease, source, shape, and size list 3300

| Order | Family | Type | General name | Genus Name | Disease / Allergy | Shape | Size (μm) |
|---|---|---|---|---|---|---|---|
| Fagales | Betulaceae | Tree | Birch | Betula verrucosa | Sneezing, Stuffy nose | Spheroidal | 10–25 D |
| Fagales | Fagaceae | Tree | Beech | Fagus engleriana | Rhinitis, Asthama | Ellipsoidal | 29–44 D |
| Salicales | Salicaceae | Tree | Willow | Salix caprea | Seneezing, Itchy eyes | Long and narrow | 28–34 x 20–21 D |
| Utricales | Ulmaceae | Tree | Elm | Ulmus americana | itching, sneezing, wheezing, headache, sinus pain, breathing problems, red or tearing eyes | Spheroidal | 25–36 D |
| Malvales | Moraceae | Tree | Mulberry | Morus alba | Asthma - acoughing and wheezing | Ellipsoidal | 13–22 D |
| Sapindales | Aceraceae | Tree | Maple | Olea europaea | Sneezing. Nasal congestion. Runny nose | Ellipsoidal | 22–28 D |
| Sapindales | Oleaceae | Tree | Olive | Olea europaea | Same as above | Ellipsoidal | 22–28 D |
| Pinales | Cupressaceae | Tree | Cypress | Cupressus arizonica | Same as above | Spheroidal | 20–29 D |
| Pinales | Pinaceae | Tree | Pine | Pinus densiflora | Same as above | Ellipsoidal | 40–85 D |
| Poales | Gramiceae | Grass | Orchard grass | Dactylis glomerata L. | Runny or stuffy nose. itchy throat, mouth, skin, or eyes. puffy eyes | Spheroidal to ovoidal | 22–122 D |
| Poales | Gramiceae | Grass | Sweet vernal grass | Anthoxantu odoratum | Same as above | Spheroidal to ovoidal | 22–122 D |
| Asterales | Asteraceae | Weed | Common ragweed | Ambrosia artemiiifolia L. | Itchy mouth, throat, tongue, or face | Spherical | 15–25 D |
| Caryophyllales | Amaranthaceae | Weed | Pigweed | A. retroflexus | Itchy mouth, throat, tongue, or face | Spherical | 18–31 D |

Pollen attributes and biosensor detector list 3390

| Pollen attributes | Shape, Size, Structure, Exine, Number of apertures |
|---|---|
| Biosensor detector | Particulate matter sensor |

FIG. 33

Pollen tree taxonomy 3410

| Pollen Taxonomy | | Kingdom | Plantae | | |
|---|---|---|---|---|---|
| Phylum | Class | Order | Family | Genus | Species |
| Angiospermatophyta | Dicotyledonouses | Asterales | Asteraceae | Ambrosia | Ambrosia artemisiifolia |
| Spermatophyta | Dicotyledonae | Urticales | Moraceae | Morus | Morus alba |

Pollen data 3430

| No | Data |
|---|---|
| 1 | Allergens of Pollen, Pollen Allergy |
| 2 | Annotation – Pollen grain and associated allergies |
| 3 | Pollen Safety Data Sheet – Pollen type, name, allergy identification, diagnosis, first aid / medical, and regulatory and other information |
| 4 | Attributes – Pollen grain size and shape, number, and arrangement of apertures, exine and intine thickness, exine sculpture, and internal texture. |
| 5 | Unique Identifiers – Unique identification of a pollen based on biosensor transducer used to detect pollen |

Pollen database 3450

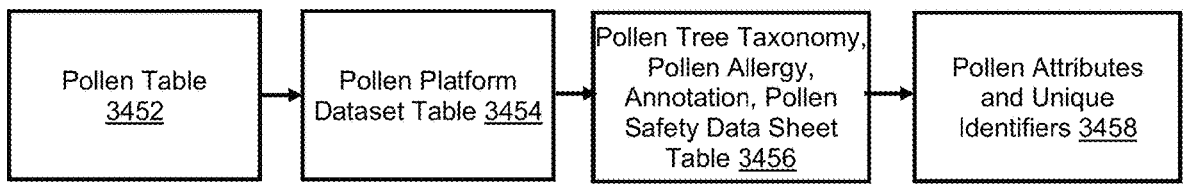

FIG. 34

Particulate matter sensor pinout 3510

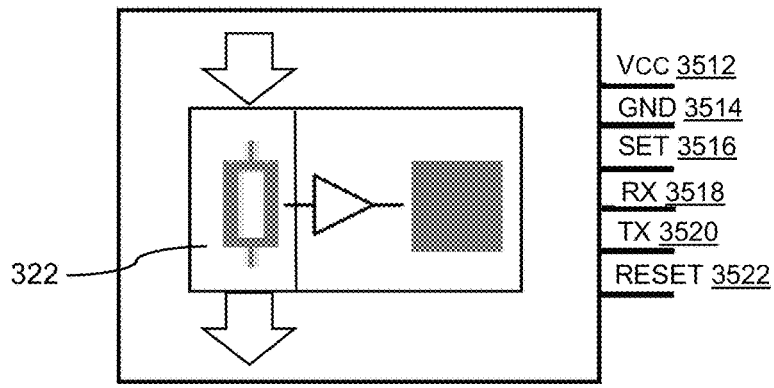

Particulate matter sensor wiring table 3550

| Particulate matter sensor pinout | Particulate matter sensor pin function | Steps to wire an particulate matter sensor pin to the SBC GPIO pin |
|---|---|---|
| Vcc 3512 | Vcc 3512 pin is used as positive power supply. | Connect particulate matter sensor Vcc 3512 pin to the assigned SBC GPIO pinout 370 5V power pin. |
| GND 3514 | GND 3514 pin is used as negative power ground. | Connect particulate matter sensor GND 3514 pin to the assigned SBC GPIO pinout 370 GND pin. |
| SET 3516 | SET 3516 pin is used as high level 3V3 or suspending normal working status, while low level is sleeping mode. | Connect particulate matter sensor SET 3516 pin to the assigned SBC GPIO pinout 370 pin. |
| RX 3518 | RX 3518 pin is used to configure and send data to the particulate matter control from the single board microcomputer. | Connect particulate matter sensor RX 3518 pin to the assigned SBC GPIO pinout 370 TXD pin. |
| TX 3520 | TX 3520 pin transmits data from the particulate matter control sensor to the single board microcomputer. | Connect particulate matter sensor TX 3520 pin to the assigned SBC GPIO pinout 370 RXD pin. |
| RESET 3522 | RESET 3522 pin is used to reset the particulate matter sensor. Reset signal is 3V3. | Connect particulate matter sensor RESET 3522 pin to the assigned SBC GPIO pinout 370 pin. |

FIG. 35

Particulate matter sensor working principle block diagram 3610

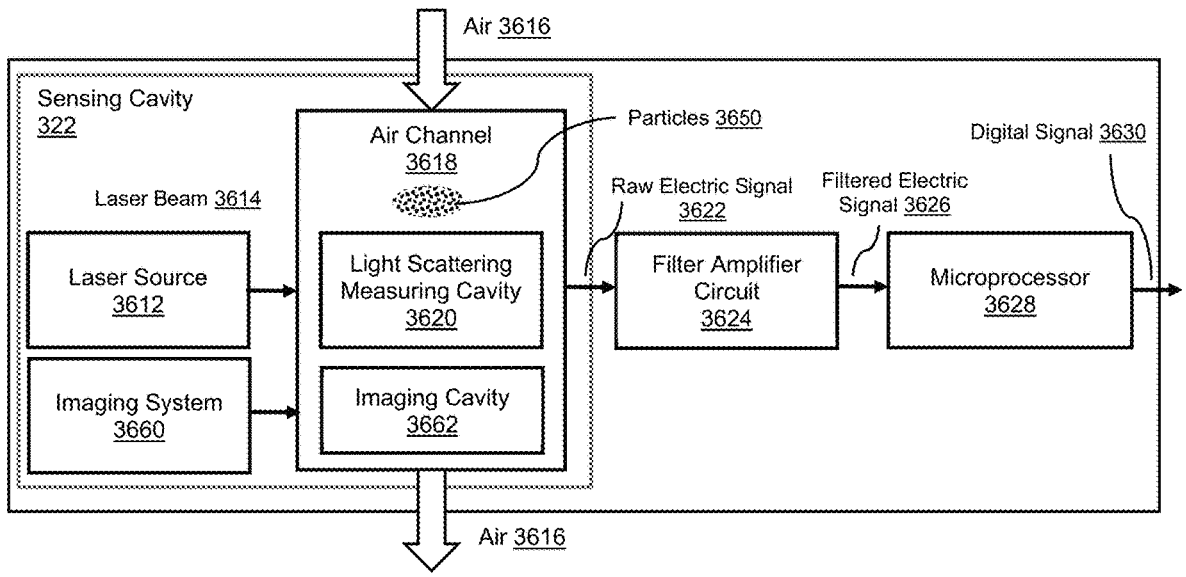

Air quality index level of concern table 3680

| AQI Color | Levels of Concern | Values of Index | Description of Air Quality |
|---|---|---|---|
| Green | Good | 0 to 50 | Air quality is satisfactory, and air pollution poses little or no risk. |
| Yellow | Moderate | 51 to 100 | Air quality is acceptable. However, there may be a risk for some people, particularly those who are unusually sensitive to air pollution. Some might require personal protective equipment (PPE) while going out. |
| Orange | Unhealthy for Sensitive Groups | 101 to 150 | Members of sensitive groups may experience health effects. The public is less likely to be affected. Sensitive groups might require PPE while going out. |
| Red | Unhealthy | 151 to 200 | Some members of the public may experience health effects; members of sensitive groups may experience more serious health effects. Wear PPE while going out. |
| Purple | Very Unhealthy | 201 to 300 | Health alert: the risk of health effects is increased for everyone. Wear PPE while going out. |
| Maroon | Hazardous | 301 and higher | Health warning of emergency conditions: everyone is more likely to be affected. Wear PPE while going out. |

FIG. 36

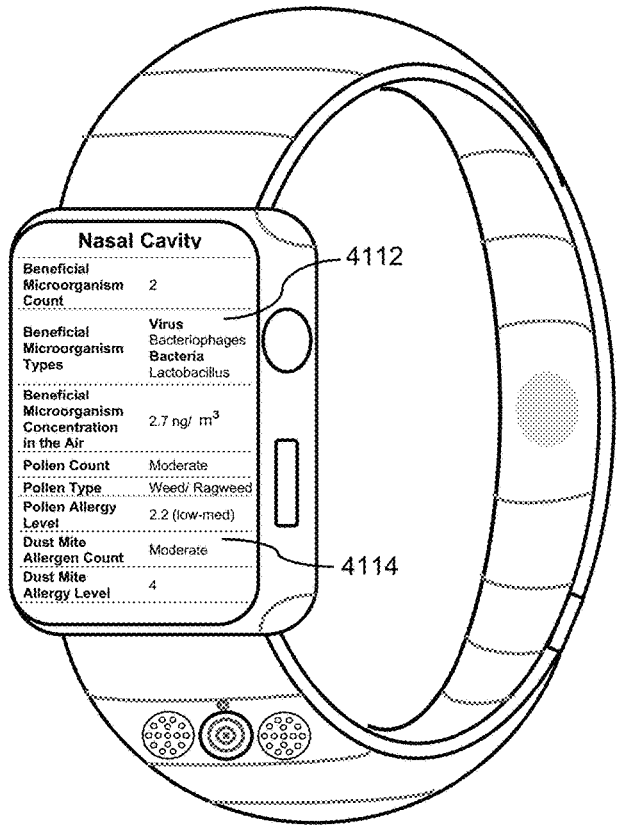
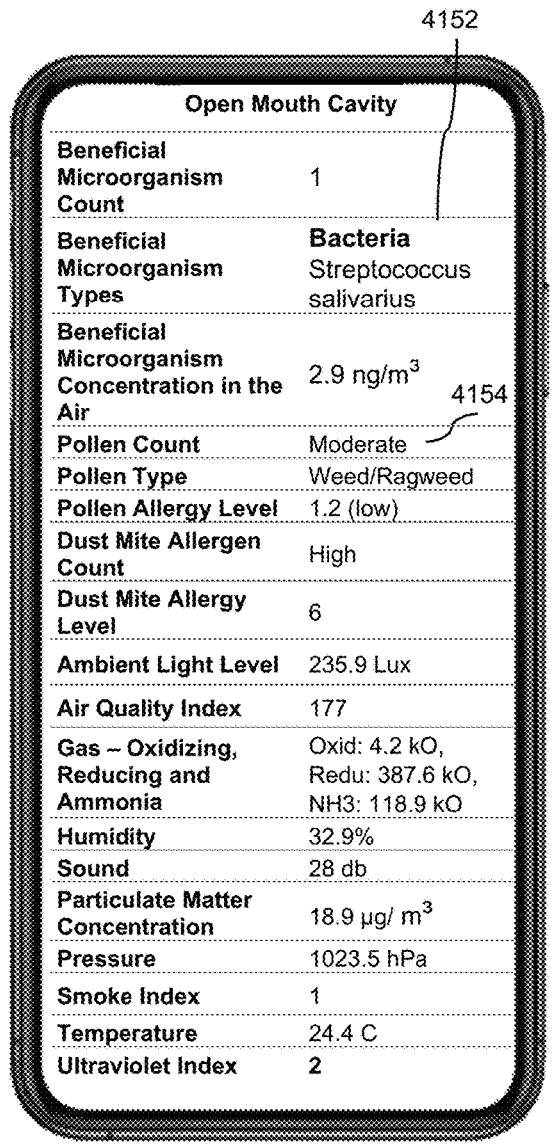
FIG. 41

Alerts 4300
Pathogen Biosafety Alert 4310
Virus Influenza virus type A found in <nasal cavity> or
<open mouth cavity> or <surrounding air>
Biosafety Level 1
User: First Name, Last Name
Date: June 27, 2021
Location: University Avenue, Palo Alto, California, USA
**Poll

PATHOGEN SAFETY DATA SHEET – Influenza virus type A

SECTION 1 - INFECTIOUS AGENT

NAME: Influenza virus type A.

SYNONYM OR CROSS REFERENCE: *Orthomyxovirus*, grippe, and flu

CHARACTERISTICS: Members of the *Orthomyxoviridae* family of segmented, negative sense, single-stranded RNA viruses. Type A influenza viruses are subdivided based on the antigenic nature of their membrane-bound surface glycoproteins, haemaglutinin (HA) and neuraminidase (NA).

SECTION 2 – HAZARD IDENTIFICATION INFORMATION

PATHOGENICITY/TOXICITY: An acute viral disease of the upper respiratory tract characterized by fever (temperature 37.8°C or above), headache, myalgia, malaise, sore throat, non-productive cough, sneezing and nasal discharge

EPIDEMIOLOGY: Influenza caused approximately 36,000 deaths per year in the United States between 1990 and 1999, and approximately 226,000 hospitalizations between 1979 and 2000.

HOST RANGE: Humans, swine, horses, domestic and wild avian species (predominantly ducks), geese, and shorebirds

INFECTIOUS DOSE: Unknown for specific influenza A subtypes. The infectious dose for the influenza A variant, Influenza A2, is greater than 790 organisms via the nasopharyngeal route.

MODE OF TRANSMISSION: Transmission of influenza in humans can occur via respiratory infection by aerosols and droplets (from coughing and sneezing) or from contact transmission from contaminated surfaces

INCUBATION PERIOD: Short, usually 1 to 3 days.

COMMUNICABILITY: Highly communicable. Infected persons can shed detectable amounts of influenza virus the day before symptoms begin. Adults usually shed the virus for 3 to 5 days, and up to 7 days in young children.

SECTION 3 – DISSEMINATION / TRANSMISSION

RESERVOIR: Humans are the principal reservoir of human influenza A viruses. The avian reservoir of influenza A viruses is wild birds, predominantly ducks, geese, and shorebirds. Animal reservoirs are suspected as sources of new human subtypes.

ZOONOSIS: Transmission from pigs to humans has been demonstrated. There are documented cases of human infections with swine influenza viruses, and zoonotic infection may occur frequently in those involved directly or indirectly in swine farming.

VECTORS: None.

Page 1

FIG. 44

SECTION 4 – STABILITY AND VIABILITY

DRUG SUSCEPTIBILITY: Seasonal influenza viruses are sensitive to the neuraminidase inhibitors oseltamivir (Tamiflu), and zanamivir (Relenza), and to amantadine, and rimantadine, which inhibit the M2 ion channel protein activity and block viral uncoating.

DRUG RESISTANCE: A significant increase in resistance to oseltamivir, adamantanes (amantadine, and rimantadine) has been observed recently.

SUSCEPTIBILITY TO DISINFECTANTS: Influenza A is susceptible to disinfectants, including sodium hypochlorite (freshly made 1:10 dilution of bleach), 60 to 95% ethanol, 2% alkaline glutaraldehyde, 5 to 8% formalin, and 5% phenol.

PHYSICAL INACTIVATION: Susceptible to moist heat at 121°C for 20 minutes or dry heat at 170°C for 1 hour, 160°C for 2 hours, or 121°C for at least 16 hours.

SURVIVAL OUTSIDE HOST: Influenza A virus can survive for 24 to 48 hours on hard, nonporous surfaces such as stainless steel and plastic and for approximately 8 to 12 hours on cloth, paper, and tissues.

SECTION 5 – FIRST AID / MEDICAL

SURVEILLANCE: Monitor for symptoms of influenza. Confirm diagnosis with RT-PCR (favored) or point-of-care testing and give appropriate antiviral treatment. Laboratory confirmation of the virus is not routinely performed, occurring only during an epidemic and consists of inoculating cell cultures with swabs or washings taken from the nose during the first days of illness.

Note: All diagnostic methods are not necessarily available in all countries.

FIRST AID/TREATMENT: Fluids and rest. Antiviral agents (mainly oseltamivir) can be employed to treat influenza A. Antibiotic treatment (in combination with antiviral treatment) may also be used to prevent or treat secondary bacterial pneumonia.

IMMUNIZATION: The most effective strategy for reducing the effect of influenza is through annual vaccination using a live, attenuated influenza vaccine (LAIV) or an inactivated influenza vaccine (TIV)

PROPHYLAXIS: Vaccines are available for influenza A subtypes H1N1 and H3N2; however, chemoprophylactic drugs must not be overlooked in the control or prevention of influenza. Antiviral prophylaxis must be initiated within 3 days of the detected illness of the index cases to be effective in slowing transmission.

SECTION 6 – LABORATORY HAZARDS

LABORATORY-ACQUIRED INFECTIONS: Fifteen reported cases up to 1974. Animal-associated infections are not reported; however, risk is high from infected ferrets.

SOURCES/SPECIMENS: Respiratory tissues, human secretions, and infected animals. In addition, the virus may be present in the intestines and cloacae of infected avian species. Influenza A may be disseminated in multiple organs in infected animal species.

Page 2

FIG. 45

PRIMARY HAZARDS: Inhalation of virus from aerosols generated when aspirating, dispensing, or mixing virus-infected samples (tissues, feces, secretions) from infected animals. Laboratory infection can also occur from direct inoculation of mucous membranes via virus contaminated gloves following the handling of tissues, feces and/or secretions from infected animals.

SPECIAL HAZARDS: Genetic manipulation of virus has an unknown potential for altering host range, pathogenicity, and/or for introducing transmissible viruses with novel antigenic composition into humans.

SECTION 7 – EXPOSURE CONTROLS / PERSONAL PROTECTION

RISK GROUP CLASSIFICATION: Risk Group 2. This risk group applies to the species as a whole and may not apply to every strain.

CONTAINMENT REQUIREMENTS: Containment Level 2 facilities, equipment, and operational practices for work involving infectious or potentially infectious materials and cultures.

PROTECTIVE CLOTHING: For diagnostic work: Lab Coat. Gloves when direct skin contact with infected materials or animals is unavoidable. Eye protection must be used where there is a known or potential risk of exposure to splashes.

OTHER PRECAUTIONS: All procedures that may produce aerosols or involve high concentrations or large volumes should be conducted in a biological safety cabinet (BSC). The use of needles, syringes, and other sharp objects should be strictly limited.

SECTION 8 - HANDLING AND STORAGE

SPILLS: Allow aerosols to settle and, wearing protective clothing, gently cover the spill with paper towels and apply suitable disinfectant, starting at the perimeter and working towards the center. Allow sufficient contact time (30 minutes) and then clean the area.

DISPOSAL: Decontaminate before disposal by steam sterilization, chemical disinfection, or incineration.

STORAGE: In sealed containers that are appropriately labelled.

SECTION 9 – EDUCATION AND TRAINING

SECTION 10 – REGULATORY AND OTHER INFORMATION

REGULATORY INFORMATION: The import, transport, and use of pathogens in the US is regulated under many regulatory bodies. If you are in country outside of the USA. Please check local regulations Users are responsible for ensuring they are compliant with all relevant acts, regulations, guidelines, and standards.

Although the information, opinions and recommendations contained in this Pathogen Safety Data Sheet are compiled from sources believed to be reliable, there is no guarantee that and we accept no responsibility for the accuracy, sufficiency, or reliability or for any loss or injury resulting from the use of the information. All attempts are made to keep the information uptodate. Newly discovered hazards are frequent, and this information may not be completely up to date. The information is provided for educational purpose only.

Page 3

FIG. 46

POLLEN SAFETY DATA SHEET – Ragweed

SECTION 1 – POLLEN TYPE

NAME: Ragweed/Weed

SYNONYM OR CROSS REFERENCE: *Family: Asteraceae, Scientific name: Ambrosia, Higher classification: Daisy family, Kingdom: Plantae, Order: Asterales, Rank: Genus*. Members of this plant family include Sage, Burweed marsh elder, Rabbit brush, Mugwort, Groundsel bush, Eupatorium.

CHARACTERISTICS: Ragweed is a weed that grows throughout the United States, especially in the Eastern and Midwestern states. Each plant lives only one season. But that one plant can produce up to 1 billion pollen grains. There are about 17 types of ragweed in North America, two species are the most abundant. Common ragweed (Ambrosia artemisiifolia) and Giant ragweed (Ambrosia trifida).

SECTION 2 – ALLERGY IDENTIFICATION

ALLERGY SYMPTOMS: Ragweed pollen inhaled from the air causes rhinitis (hay fever) symptoms. Rhinitis symptoms often include sneezing, stuffy or runny nose, Itchy eyes, nose, and throat, Itchy or puffy eyes, Mucus in the throat (postnasal drip)

HOST RANGE: Humans, and other mammalians.

MODE OF TRANSMISSION: Transmission of ragweed pollen in humans can occur via air or from contact transmission from contaminated surfaces with ragweed pollen.

SECTION 3 – DIAGNOSIS

Skin prick test to confirm your allergy.

SECTION 4 – FIRST AID / MEDICAL

There is no cure for a ragweed pollen allergy but there are ways to treat and manage it such as
Track the pollen count for your area.
Stay indoors in central air conditioning.
Prevent pollen from being tracked into your home.
Take anti-inflammatory or antihistamine medicines.

SECTION 5 – EDUCATION AND TRAINING

SECTION 6 – REGULATORY AND OTHER INFORMATION

REGULATORY INFORMATION:

Although the information, opinions and recommendations contained in this Pollen Safety Data Sheet are compiled from sources believed to be reliable, there is no guarantee that and we accept no responsibility for the accuracy, sufficiency, or reliability or for any loss or injury resulting from the use of the information. All attempts are made to keep the information uptodate. Newly discovered hazards are frequent, and this information may not be completely up to date. The information is provided for educational purpose only.

FIG. 47

Necklace 4810
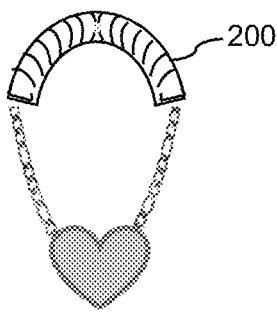
Waistband 4820
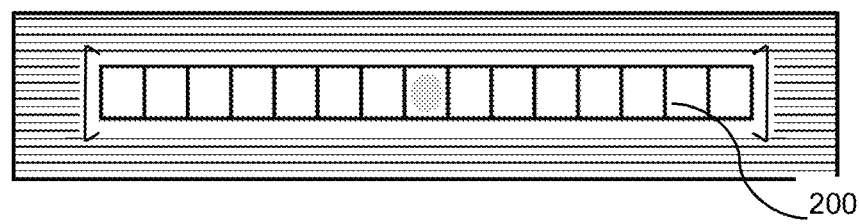
Belt 4830
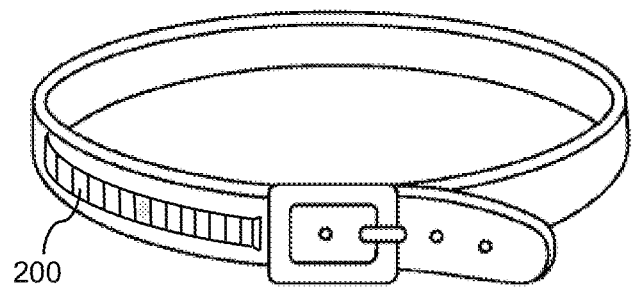
Headband 4840
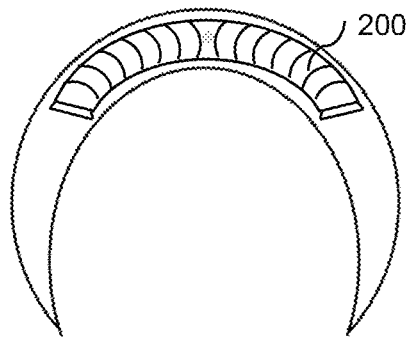
FIG. 48

WEARABLE DEVICE FOR DETECTING MICROORGANISMS, STERILIZING PATHOGENS, AND ENVIRONMENTAL MONITORING

FIELD OF THE INVENTION

This present invention relates generally to the field of microorganism detection, pathogen sterilization, and environmental monitoring, and more specifically to the wearable device comprising a smart band and a display unit. The smart band consists of a microbial biosensor which detects beneficial microorganisms, and pathogenic biological agents such as prions, viruses, bacteria, fungi, protists, and dust mites found in a nasal cavity, an oral cavity, or on a surface. The microbial biosensor can sterilize the pathogens. The particulate matter allows pathogenic biological agents such prions, viruses, bacteria, fungi, protists, dust mites, pollen, and dust mite allergens to be detected, measured, and monitored in the air surrounding the user. The enviro sensor detects, measures, and monitors environmental conditions in the air surrounding the user.

DESCRIPTION OF THE PRIOR ART

There exist various types of devices for microorganism detection, pathogen sterilization, and environmental monitoring. Current beneficial microorganism and pathogen detection tests usually require a visit to a hospital for sample collection. This is followed by sending the sample to a clinical laboratory for testing and reporting of the results. Testing is expensive, resource intensive, and time consuming, and results are only available after a few days. Some of the common test methods are as follows:

1) RT-PCR, which is the synthesis of cDNA (complementary DNA) from RNA by reverse transcription (RT) and the amplification of a specific cDNA by the polymerase chain reaction (PCR) from a nasopharyngeal or oropharyngeal swab sample.
2) Antibody Test, which is based on binding of antibodies from a blood or serum or plasma sample to labeled antigens.
3) Antigen Test, which is based on binding of antigens from a nasopharyngeal or oropharyngeal swab sample to labeled antibodies.
4) Microscope based test, the working principle of which involves viewing of a labeled pathogen image under a microscope from a blood, saliva, or tissue sample.
5) Next-generation sequencing is a term that collectively refers to high-throughput DNA sequencing strategies that can produce large amounts of genomic data in a single reaction by diverse methodologies. Customized pathogens panels allow for detection of pathogens in a sample. Microbial profiling using 16S ribosomal RNA (rRNA) sequencing is a common method for studying bacterial phylogeny and taxonomy.
6) Microarray is a microchip-based testing platform that allows high-volume, automated analysis of many pieces of DNA at once, including pathogen arrays.
7) Mass Spectrometry is useful for measuring the mass-to-charge ratio (m/z) of one or more molecules present in a sample. These measurements can often be used to calculate the exact molecular weight of the sample components as well. The Identification of pathogens by Mass Spectrometry can be done by cell enrichment, nucleic acid amplification, or direct sampling methods on microbial samples. The basic principle of mass spectrometry (MS) is to generate ions from either inorganic or organic compounds by a suitable method, to separate these ions by their mass-to-charge ratio (m/z) and to detect them qualitatively and quantitatively by their respective m/z and abundance.

These test methods include clinical laboratory testing run on an in vitro diagnostic instrument. The manufacturer of the test must establish analytical and clinical performance. The total testing process in the laboratory is a cyclical process divided into three phases: preanalytical, analytical, and postanalytical. In the pre-analytical phase, the patient sample is collected and sent to a clinical laboratory, where is it accessioned. In pre-analytical phase for certain methods the sample must go through microbial culture of multiplying microorganisms by letting them reproduce in predetermined culture media under controlled laboratory conditions. The analytic phase begins when the patient specimen is prepared for testing and ends when the test result is interpreted and verified. The analytical phase includes moderate or high complexity testing on an in vitro diagnostic instrument, using reagents and consumables, by the clinical laboratory scientist. The post-analytic phase is the final phase of the laboratory process. This phase culminates in the creation and reporting of patient results by the laboratory director. Along with laboratory testing, computed tomography of the chest, commonly known as CT scans, may be helpful to diagnose pathogens like COVID-19 in individuals with a high clinical suspicion of infection, especially in lungs. For samples like wastewater, food, and crime scenes, the pathogen or microbial testing is done in specialized labs like water testing laboratories, food testing laboratories, and forensic laboratories, respectively. The above tests and instruments are not noninvasive point of care devices to detect microorganisms, sterilize pathogens, and monitor the surrounding air environment. The tests require specialized laboratories, trained resources, sample transportation, and specialized equipment and consumables.

U.S. Patent App. No. US 2018/0298418 A1 to Ronnie J. Robinson et al. discloses a method and automated apparatus for rapid noninvasive detection of a microbial agent in a test sample, which is described herein. The apparatus may include one or more means for automated loading, automated transfer, and/or automated unloading of a specimen container. The apparatus also includes a detection system for receiving a detection container, e.g., container or vial, containing a biological sample and culture media. The detection system may also include one or more heated sources, holding structures or racks, and/or a detection unit for monitoring and/or interrogating the specimen container to detect whether the container is positive for the presence of a microbial agent therein. The U.S. Patent to Ronnie J. Robinson et al. does not teach or claim a no-invasive wearable device. The apparatus detection system is bulky and has to be installed in a special testing facility. The test sample must be collected and loaded on the system. The patent does not claim multiplex detection of prions, viruses, fungi, protists, dust mites, and pollen using a non-invasive wearable device.

Japan Patent No. JP5707399B2 to Katsuran Lee et al. discloses a microorganism method, a microorganism detection apparatus, and a program for inspecting an inspection object such as food by detecting bacteria such as *E. coli* and microorganisms such as eukaryotes. The test requires sample collection and laboratory testing. The patent does not support or claim a noninvasive wearable device and detection of prions, viruses, fungi, protists, dust mites, and pollen.

U.S. Patent App. No. 2016/U.S. Pat. No. 9,291,549 B2 to Eric Schwoebel et al. discloses a pathogen detection biosensor, which provides methods for the detection of target particles, such as pathogens, soluble antigens, nucleic acids, toxins, chemicals, plant pathogens, blood borne pathogens, bacteria, viruses, and the like. The method for detecting an antigen in a sample comprises a spraying of emitter cells onto a sample. The emitter cell comprises a receptor and an emitter molecule that emits a photon in response to binding of a target antigen in the sample to the receptor. The photon emission is indicative of the antigen in the sample. The optoelectronic sensor device can detect a target particle in a liquid sample, or in an air or aerosol sample. The biosensor size is about 2 feet and bulky. The U.S. Patent to Eric Schwoebel et al. does not teach or claim a wearable device. It does not test for beneficial microorganisms and pathogens in a nasal and an oral cavity. The technology involved is spraying of emitter cells. It does not have built in sterilizer, which is very important to disinfect. The device cannot be carried by the user.

U.S. Patent App. No. 2005/U.S. Pat. No. 6,996,472 B2 to Jon G. Wilkes et al. discloses a method of compensating for drift in fingerprint spectra of microorganisms caused by changes in their environment. These methods of compensating for drift permit identification of microorganisms from their fingerprint spectra regardless of the environment from which the microorganisms are obtained. The disclosed methods use a coherent database of fingerprint spectra that may be expanded even though the standard database conditions are no longer experimentally achievable. In particular embodiments, methods of compensating for drift in pyrolysis mass spectra, constructing coherent pyrolysis mass spectral databases, and identifying bacteria from their pyrolysis mass spectra are disclosed. The U.S. Patent to Jon G. Wilkes et al. does not teach or claim a wearable device with real time detection of beneficial microorganisms, pathogens, pollen, and environmental conditions. The disclosed method does not include the sterilization. The method disclosed is culturing of microorganisms and involves wet laboratory testing. It does not cover the fingerprint spectra database and does not detect viruses and pollen.

U.S. Patent App. No. 2009/U.S. Pat. No. 7,542,137 B2 to Sangeeta Murugkar, et al. provides a system and method for automatic real-time monitoring for the presence of a pathogen in water using coherent anti-stokes Raman scattering (CARS) microscopy. A water sample trapped in a trapping medium is provided to a CARS imager. CARS images are provided to a processor for automatic analyzing for the presence of image artifacts having pre-determined features characteristic to the pathogen. If a match is found, a CARS spectrum is taken and compared to a stored library of reference pathogen-specific spectra for pathogen identification. The system enables automatic pathogen detection in flowing water in real time. The U.S. Patent to Sangeeta Murugkar, et al. does not teach or claim a wearable device to test for pathogens in a nasal cavity, an oral cavity, on a surface, or in surrounding air. The device is very bulky and cannot be carried by the user. It tests for pathogens in water only.

U.S. Patent App. No. 2020/U.S. Pat. No. 10,724,068 B2 to Mansour Samadpour discloses methods for enrichment and detection of pathogens or other microbes in a food, water, wastewater, industrial, pharmaceutical, botanical, environmental sample, and other types of samples provided. In particular aspects, a sample is obtained and diluted at a first location and incubated at an optimal temperature and either tested locally or sent in a shipping incubator to a second location that may be a remote test location for testing with an assay suitable to detect the pathogen or other microbe. The U.S. Patent to Mansour Samadpour does not teach or claim a wearable device providing a real time beneficial microorganism, pathogen, and pollen detection. It is liquid sample-based testing run in a laboratory environment.

U.S. Patent App. No. 2008/U.S. Pat. No. 7,430,046 B2 to Jian-Ping Jiang et al. discloses a particle detector that has a sample area of cross section not in excess of about 2 mm for containing environmental fluid, a light source on one side of the sample area for directing a collimated or nearly collimated beam of light through the sample air or water so that part of the light beam will be scattered by any particles present in the air or water while the remainder remains unscattered, and a beam diverting device on the opposite side of the sample area for diverting or blocking at least the unscattered portion of the beam of light and directing at least part of the scattered light onto a detector. The detector produces output pulses in which each pulse has a height proportional to particle size, and a pulse height discriminator obtains the size distribution of airborne particles detected in the air or water sample at a given time from the detector output. The detector may also include a device for discriminating between biological agents and inorganic particles. The U.S. Patent to Jian-Ping Jiang et al. does not teach or claim a wearable device to detect and sterilize pathogens. The detector cannot be worn by the user for rapid detection of the pathogens.

There exist several beneficial microorganism and pathogen testing-based patents for RT-PCR, microarray, next generation sequencing (NGS), clustered regularly interspaced short palindromic repeats (CRISPR), mass spectrometer, microscope enzyme-linked immunosorbent assay (ELISA), an analytical technique to detect the presence of an antigen or antibody in a given sample. There are microscope-based methods which involve identification of bacteria based on morphological features of the cells, which can be visualized via microscopic observation, staining to detect important cellular structure, hyperspectral imaging darkfield microscopy, and so on. There also exist self-test devices or point of care pathogen testing devices which require sample collection and testing. All these patents involve wet lab clinical laboratory-based testing. These methods are limited to testing few beneficial microorganisms and pathogen types and are time consuming. The test requires a clinical laboratory facility and skilled clinical laboratory scientist. The testing protocol consists of use of in vitro diagnostic instrument, reagents, consumables, software, and data intensive computers.

In summary, the scope, and contents of the prior art of the above beneficial microorganism, pathogen devices, and detectors for testing and sterilizing pathogens are limited because of size of the device, fixed location, laboratory-based testing, and not being wearable devices. The pathogen testing is limited to few pathogen types within each of the categories of viruses, bacteria, and fungi. As such there exists a need for an inexpensive wearable device which can noninvasively detect both beneficial microorganisms and pathogens such as prions, viruses, bacteria, fungi, dust mites, pollen, and so on in a nasal cavity, an oral cavity, on a surface, or in the air surrounding the user in a cost-effective manner. The wearable device should also allow for detection of the pollen in the air, allergy forecast, and environmental conditions. The wearable device allows the user to diagnose medical diseases and conditions associated with pathogens, allergens, and pollen, and predict treatment response or reactions and define or monitor therapeutic measures in consultation with their physician.

The innovative wearable device is suitable for testing beneficial microorganisms, pathogens, pollens, and dust mite allergens. Lately, due to spread of infectious diseases like COVID-19, Dengue, Ebola, ringworm, strep throat, food poisoning, and other diseases, it has become increasingly important to do real time testing for pathogens like prions, viruses, bacteria, fungi, protists, dust mites, and so on without collecting a sample. The wearable device can also sterilize the pathogens. The wearable device does not use substrate made of glass, paper, polymer, and silicon with nasal, oral, blood, serum, tissue, or surface samples as needed by traditional wet lab-based test.

In conclusion, compared to prior art, the present invention incorporates a wearable device which comprises innovative sensors. A wearable device consists of a smart band, and a display unit. The smart band comprises a microbial biosensor, a particulate matter sensor, and an enviro sensor. The microbial biosensor detects, measures, and monitors a beneficial microorganism count, a beneficial microorganism type, and a beneficial microorganism concentration, a pathogen count, a pathogen type, a pathogen concentration, and a pathogen biosafety level in a nasal cavity, an oral cavity, or on a surface. The microbial biosensor sterilizer kills pathogens. The particulate matter sensor detects, measures, and monitors a set of suspended particles in the surrounding air comprising a beneficial microorganism, a pathogen, a pollen, and an air quality index. The enviro sensor detects, monitors, and measures environmental conditions surrounding the user. The agile sensor particle detection methods based on machine learning algorithms implement, operate, detect, measure, monitor, and store sensor data locally and transmit to the cloud server. The wearable device is a point of care (POC) device providing results while with the user or close to the user. The wearable device eliminates sample collection, transportation, laboratory testing, reporting of results, and associated biohazardous waste. The analytical and clinical performance of the wearable device is very high because of confirmation of results by multiple particle detection methods.

SUMMARY OF THE INVENTION

A wearable device consists of a smart band, and a display unit. The smart band comprises a microbial biosensor, a particulate matter sensor, an enviro sensor, a single board computer, a power supply unit, a band fastener, and a set of watch adapters. The microbial biosensor detects, measures, and monitors beneficial microorganisms and pathogens in a nasal cavity, an oral cavity, or on a surface. The microbial biosensor sterilizer kills pathogens. The particulate matter sensor detects, measures, and monitors a set of suspended particles in the surrounding air comprising beneficial microorganisms, pathogens, pollen grains, dust mite allergens, and an air quality index. The pathogen results comprise a pathogen count, a pathogen type, a pathogen concentration, and a pathogen biosafety level. The enviro sensor detects, monitors, and measures environmental conditions surrounding the user. A computing system comprises a wearable device, a microbiome mobile application, a user, a mobile device, a cloud server, a laboratory testing facility, a laboratory information system, a laboratory director, and a physician. The smart band sends and receives signals through a wireless network to the microbiome mobile application installed on the mobile device, and to the cloud server.

BRIEF DESCRIPTION OF THE DRAWINGS

FIG. 4 is an example schematic representation of a single board computer general purpose input output pin numbering diagram, and a general purpose input output pinout function that can be utilized to implement various embodiments.

FIG. 5 is an example single board computer general purpose input output pinout function description table that can be utilized to implement various embodiments.

FIG. 6 illustrates an example set of microorganisms, pollen grain, dust mite allergen, and relative size of particles that can be utilized to implement various embodiments.

FIG. 7 is an example prion structure and components diagram, a prion structure components, function, and chemical composition list, a prion disease, status, and source list, and a prion attributes and biosensor detector list, according to some embodiments.

FIG. 8 is an example virus structure and components diagram, a virus structure components, function, and chemical composition list, and a percent chemical composition of a virus list, according to some embodiments.

FIG. 10 is an example virus name, disease, status, source, shape, size, and nucleic acid list, and a virus attributes and biosensor detector list, according to some embodiments.

FIG. 11 is an example bacteria cell structure and components diagram, a bacteria cell structure components, function, and chemical composition list, and a percent chemical composition of a bacteria list, according to some embodiments.

FIG. 12 is an example bacterial cell shapes diagram, according to some embodiments.

FIG. 13 is an example bacteria name, disease, status, source, shape, size, and nucleic acid list, and a bacteria attributes and biosensor detector list, according to some embodiments.

FIG. 14 is an example fungi cell structure and components diagram, a fungi cell structure components, function, and chemical composition list, and a percent chemical composition of a fungi list, according to some embodiments.

FIG. 15 illustrates an example fungi cell shapes diagram, and a fungi cell shape in environment and shape shift in host diagram, according to some embodiments.

FIG. 16 is an example fungi name, disease, status, source, shape, size, and nucleic acid list, and a fungi attributes and biosensor detector list, according to some embodiments.

FIG. 17 is an example protist cell structure and components diagram, a protist cell component, function, and chemical composition list, and a protist attributes, disease, source, shape, size, and nucleic acid list, and a protist attributes and biosensor detector list, according to some embodiments.

FIG. 18 is an example dust mite structure and components diagram, a dust mite structure components, function, and chemical composition list, and a dust mite attributes and biosensor detector list, according to some embodiments.

FIG. 19 is an example virus, bacteria, and fungi attributes comparison list, according to some embodiments.

FIG. 20 is an example platform dataset, and a microorganism taxonomy, according to some embodiments.

FIG. 23 illustrates an electromagnetic spectrum, and a spectrum of sound, according to some embodiments.

FIG. 24 illustrates noninvasive biosensors for microorganism detection, and sterilization list, picomaterials, and a microorganism detection method working principle list, according to some embodiments.

FIG. 25 illustrates particle detection methods, according to some embodiments.

FIG. 27 illustrates an example microbial biosensor pinout and a microbial biosensor wiring table describing the hardware wiring connection steps of a microbial biosensor pinout connected to the single board computer general purpose input output pinout that can be utilized to implement various embodiments.

FIG. 28 illustrates an example microbial biosensor infrared spectroscopy working principle diagram and a microbial biosensor particle imaging working principle diagram that can be utilized to implement various embodiments.

FIG. 29 illustrates a microbial biosensor nasal cavity test method diagram and microbial biosensor oral cavity test method diagram that can be utilized to implement various embodiments.

FIG. 30 illustrates a microbial biosensor surface test method diagram, and surface types that can be utilized to implement various embodiments.

FIG. 31 is an example pollen grain diagram, a pollen grain structure and components diagram, a pollen structure components, function, and chemical composition list, and a percent chemical composition of an air-dried pollen list, according to some embodiments.

FIG. 32 illustrates pollen grain shapes diagram, according to some embodiments.

FIG. 33 is an example pollen type source, name, disease, shape, and size list, and a pollen attributes and biosensor detector list, according to some embodiments.

FIG. 34 is an example pollen tree taxonomy, pollen data, and a pollen database, according to some embodiments.

FIG. 35 illustrates an example particulate matter sensor pinout and a particulate matter sensor wiring table describing the hardware wiring connection steps of a particulate matter sensor pinout connected to the single board computer general purpose input output pinout that can be utilized to implement various embodiments.

FIG. 36 illustrates an example particulate matter sensor working principle block diagram, and an air quality index level of concern table that can be utilized to implement various embodiments.

FIG. 41 illustrates a microbiome mobile application displaying nasal cavity beneficial microorganism results, and a microbiome mobile application displaying oral cavity beneficial microorganism results, according to some embodiments.

FIG. 43 illustrates an example pathogen biosafety alert, a pollen allergy alert, a dust mite allergy alert, and an air quality alert, according to some embodiments.

FIG. 44 is an example first page of a pathogen safety data sheet.

FIG. 45 is an example second page of a pathogen safety data sheet.

FIG. 46 is an example third page of a pathogen safety data sheet.

FIG. 47 is an example page of a pollen safety data sheet.

FIG. 48 is an example smart band attached to a necklace, a waistband, a belt, and a headband.

Figure 1:
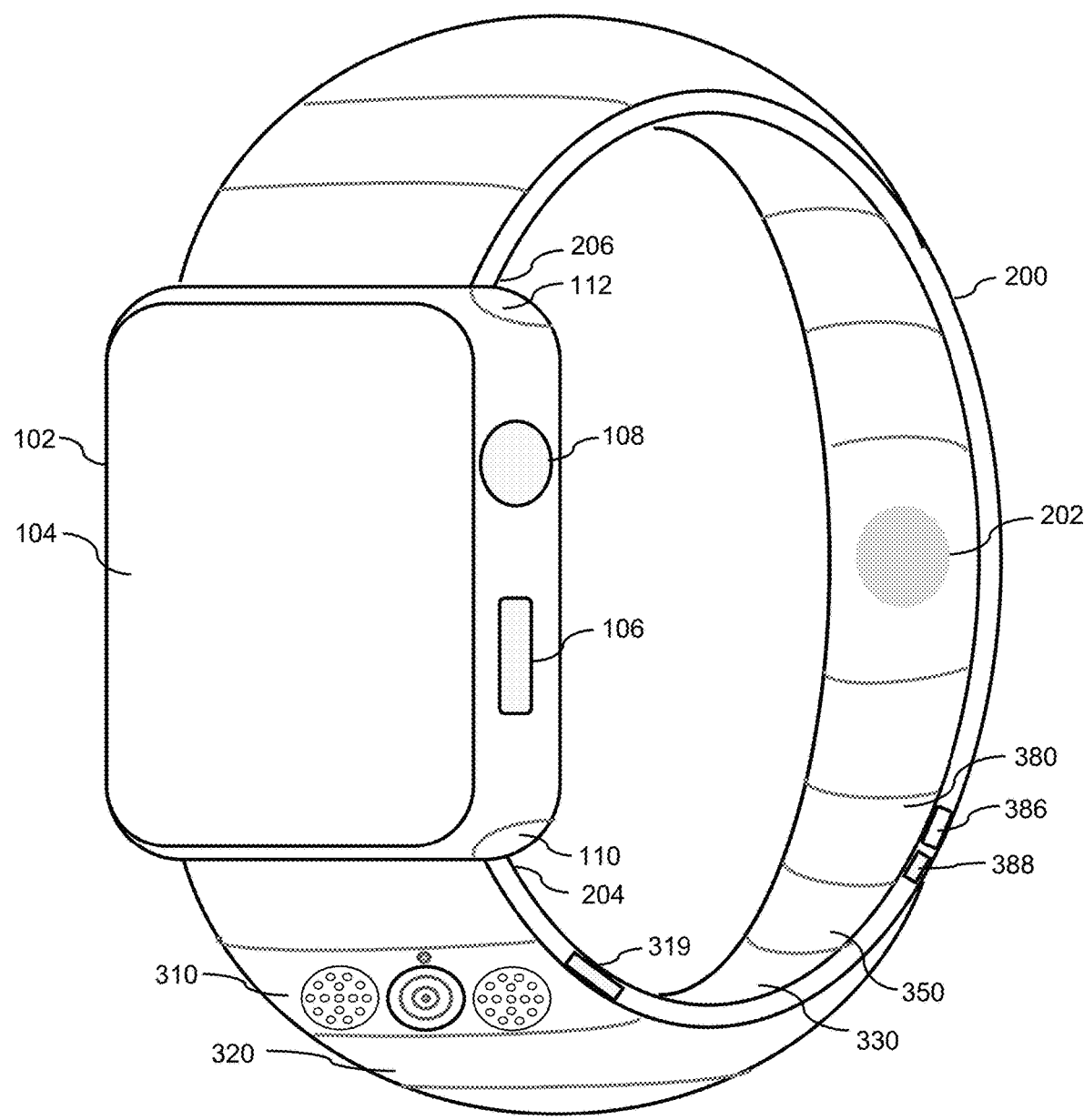
FIG. 1 is an example perspective view of an example wearable device design that can be utilized to implement various embodiments.

The Figures described above are a representative set and are not exhaustive with respect to embodying the invention.

DESCRIPTION

Disclosed are a system, method, and article of manufacture for methods and systems of a wearable device. The following description is presented to enable a person of ordinary skill in the art to make and use the various embodiments. Descriptions of specific devices, techniques, and applications are provided only as examples. Various modifications to the examples described herein can be readily apparent to those of ordinary skill in the art, and the general principles defined herein may be applied to other examples and applications without departing from the spirit and scope of the various embodiments.

Reference throughout this specification to "one embodiment," "an embodiment," "one example," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of how to operate, detect, measure, and monitor a beneficial microorganism count, a beneficial microorganism type, and a beneficial microorganism concentration, a pathogen count, a pathogen type, a pathogen concentration, and a pathogen biosafety level and environmental conditions surrounding the user using various sensors to provide a thorough understanding of embodiments of the invention. One who is skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The disclosed system consists of a wearable device, microbiome mobile application, and associated methods. A wearable device consists of a smart band, and a display unit. The smart band comprises a microbial biosensor, a particulate matter sensor, an enviro sensor, a single board computer, a power supply unit, a band fastener, and a set of watch adapters. The microbial biosensor detects, measures, and monitors beneficial microorganisms and pathogens in a nasal cavity, an oral cavity, or on a surface. The microbial biosensor sterilizer kills pathogens. The particulate matter sensor detects, measures, and monitors a set of suspended particles in the surrounding air comprising beneficial microorganisms, pathogens, pollen grains, dust mite allergens, and an air quality index. The pathogen results comprise a pathogen count, a pathogen type, a pathogen concentration, and a pathogen biosafety level. The enviro sensor detects, monitors, and measures environmental conditions surrounding the user. A computing system comprises a wearable device, a microbiome mobile application, a user, a mobile device, a cloud server, a laboratory testing facility, a laboratory information system, a laboratory director, and a physician. The smart band sends and receives signals through a wireless network to the microbiome mobile application installed on the mobile device, and to the cloud server.

In one embodiment, the system is twofold, with a hardware and software system. The hardware includes smart band, and a display unit. The display unit is removable, and a user smartwatch or standard watch can be connected. The smart band comprises a microbial biosensor, a particulate matter sensor, an enviro sensor, a single board computer, and a power supply unit. The software consists of microbiome mobile application which is preinstalled in the wearable device and displays the sensor data on the display unit. The microbiome mobile application can also be installed on the smartwatch and mobile devices. The microbiome mobile application includes different interactive user interfaces such as, inter alia: wearable device details, microbial biosensor data, a particulate matter sensor data, and an enviro sensor data. The microbiome mobile application can connect to a laboratory information system through application programmer interfaces and transmit the user wearable device data.

The disclosed invention runs on an end-to-end application workflow consisting of collecting wearable device sensor data, performing big data analysis, providing detailed results, pathogen safety data sheet, pollen safety data sheet, monitoring, trending, and reporting of performance data.

The wearable device sends a pathogen biosafety alert to the microbiome mobile application when the pathogen biosafety level is above a predetermined threshold level in the nasal cavity, oral cavity, surface, or in the air surrounding the user. The system can send the pathogen biosafety alert to the physician and laboratory information system.

The pathogen biosafety alert allows the user to take additional appropriate sterilization methods like heat treatment, ultraviolet light, acoustic wave, irradiation, thermal inactivation, and so on, to kill pathogens in a nasal cavity, an oral cavity, on a surface, or surrounding environment to ensure they are free of pathogens.

The wearable device and microbiome mobile application are self-contained and are operated independently and do not need to be connected to the cloud server. The connection to the cloud server allows for sharing of data with other users, laboratory information system, physicians, and so on.

The schematic flow chart diagrams included herein are generally set forth as logical flow chart diagrams. As such, the depicted order and labeled steps are indicative of one embodiment.

Exemplary Definitions

An accelerometer sensor can be used to measure the acceleration or deceleration of forces exerted upon the sensor. Such forces may be static, like the continuous force of gravity or, as is the case with many mobile or moving devices, dynamic, to sense movement or vibrations. The intended use of the accelerometer sensor is to measure the movement of the wearable device. The accelerometer sensor is used for centering the wearable device for nasal ID, open mouth ID, and surface ID recognition. The unit of measurement of the accelerometer sensor is the rate of change of velocity of an object expressed in meters per second squared ($m/s^2$). The accelerometer sensor sends real-time acceleration data to the microbiome mobile application and the cloud server. Accelerometers can measure acceleration in one, two, or three orthogonal axes. Accelerometer sensors are typically used in one of three modes: in the case of 1 dimension as an inertial measurement of velocity and position, as a sensor of inclination, tilt, or orientation in 2 or 3 dimensions, as referenced from the acceleration of gravity (1 $g=9.8$ $m/s^2$) and as a vibration or impact sensor. Most accelerometers are micro-electromechanical sensors (MEMS). The basic principle of operation of the MEMS accelerometer is the displacement of a small proof mass etched into the silicon surface of the integrated circuit and suspended by small beams. Per Newton's second law of motion ($F=ma$), as an acceleration is applied to the device, a force develops which displaces the mass. The support beams act as a spring and the air trapped inside integrated circuits (IC) as a damper. The common accelerometer sensor types can be capacitive sensing or use piezoelectric effect to sense the displacement of the proof mass proportional to the applied acceleration.

Air Quality Index (AQI) is an index for reporting air quality. The Air Quality Index is used to provide information about how polluted the air currently is or how polluted it is forecasted to become.

An algorithm is a precise, step-by-step plan or set of rules to be followed in calculations or computational procedures or other problem-solving operations, especially by a computer. An algorithm computational procedure begins with an input value and yields an output value in a finite number of steps. The microorganism and pathogen algorithms used are a computational procedure to calculate sensor data values, various cluster algorithms, a picocamera machine vision algorithm, a neural network algorithm, and so on. The algorithms implemented in the method can vary. Algorithms allow for rapid multiplex detection and characterization of microorganisms, pathogens, and pollen by calculating the unique identifiers.

An allergy is a damaging immune response by the body to a substance, especially pollen, a particular food, or dust, to which it has become hypersensitive. The substances that cause an allergic reaction are called allergens, which are proteins or glycoproteins. Usually they are harmless to most people. Allergy is an abnormal reaction to a very small amount of allergen. Allergens stimulate the production of allergic antibodies or sensitized cells. This response is mediated by immunoglobulin IgE antibody specific to the allergen. The basophils and mast cells are activated after IgE binding, starting a series of cellular and molecular events that results in clinical manifestation of allergic disease.

Aeroallergens are airborne particles that can cause respiratory or conjunctival allergy. Aeroallergens to be clinically significant, must be buoyant, present in significant numbers, and allergenic, such as ragweed and grass. Wind pollinated plants produce significant amount of allergen than can travel for miles. Fungal spores may be more numerous than pollen grains in the air. The house dust mite is also a very common indoor allergen.

An ambient light sensor (ALS) is an electronic component, also known as an illuminance or illumination sensor, optical sensor, brightness sensor, or simply light sensor, which is used to reduce the power consumption to provide the user with increased battery life. The intended use of the ambient light sensor is to detect, measure, and monitor ambient light inside or surrounding the wearable device to reduce power consumption and increase battery life. The wearable device can be programmed to go into power saving sleep mode when the device is turned off. The unit of measurement is lux, and it can be expressed in terms of ambient light level values of 1 to 5. The ambient light sensor sends real-time ambient light, i.e., illuminance data, to the microbiome mobile application and cloud server. Ambient light sensor technologies can be based on photo electric cell, photodiode, photo transistor, and photo integrated circuit (IC). Ambient light sensors contain a photodiode which can sense light wavelengths visible to the human eye in the 380-nm to 780-nm range and convert them into electricity. Light is measured depending upon its intensity.

Analytical performance means the ability of a device to correctly detect or measure a particular analyte. Analytical performance characteristics comprise parameters such as analytical sensitivity, analytical specificity, trueness (bias), precision (repeatability and reproducibility), accuracy (resulting from trueness and precision), limits of detection and measurement range, (information needed for the control of known relevant interferences, cross-reactions, and limitations of the method), measuring range, linearity.

An application programming interface (API) can specify how application software components of various systems interact with each other. APIs are source code-based specifications intended to be used as interfaces by application software components to communicate with each other. Microorganism and pathogen APIs allow connection and retrieval of data from public databases like National Center for Biotechnology (NCBI), European Pathogen databases, and other commercial pathogen databases. Pollen APIs allow for access to local pollen and allergy forecast data. Laboratory information system APIs are application programming interfaces that allow connection to patient health records, laboratory medical instruments, and a cloud server. Weather APIs are application programming interfaces that allow connection to large databases of weather forecast and historical information. For example, the microbiome mobile application and laboratory information system can connect to weather APIs such as OpenWeatherMap API, AccuWeather API, Dark Sky API, Air Quality API, and so on. The weather data imported from weather APIs can be used to display it on the microbiome mobile application and laboratory information system.

An audio port links the single board computer's sound hardware to speakers, microphone, headsets, or other equipment.

A bacterium is a member of a large group of unicellular microorganisms classified as prokaryotes, which have cell walls but lack organelles and an organized nucleus, including some that can cause disease. Bacteria are microorganisms made of a single cell, and those that cause infections are called pathogenic bacteria. Currently it is estimated that about 700 species of bacteria are found in the oral cavity, many which are still uncultivable and need to be identified. About 20 are known to be pathogenic. The most common bacteria sizes are about 1 to 2 µm in diameter and 5 to 10 µm long. The bacteria shapes are spherical bacteria (Coccus), rod-shaped bacteria (*Bacillus*), Spiral bacteria, Filamentous bacteria, Box Shaped bacteria, Appendaged bacteria, Pleomorphic bacteria, and so on. Bacteria are microscopic organisms not visible with the naked eye. Bacteria are everywhere, both inside and outside of our body. Bacteria can live in a variety of environments, from hot water to ice. Some bacteria are good for humans, while others can make us sick. These beneficial or good bacteria, also called probiotics, reside naturally in the body. Probiotics may be beneficial to health and are available in yogurt or in various dietary supplements. Some of the good bacteria are as follows: a) *Lactobacillus Acidophilus* resides in the intestines where it helps in the digestion of food. b) Bifidobacteria make up most of the "good" bacteria living in the gut. They help to digest dietary fiber, prevent infection, and produce vitamins and other important chemicals. c) *Streptococcus thermophilus* is for relief of the abdominal cramps, diarrhea, nausea, and other gastrointestinal symptoms associated with lactose intolerance. d) *Saccharomyces boulardii* is most used for treating and preventing diarrhea, including infectious types such as rotaviral diarrhea in children. e) *Bacillus coagulans* may be useful in the treatment of gastrointestinal disorders such as diarrhea associated with an antibiotic regimen, inflammatory bowel disease, and irritable bowel syndrome. Many disease-causing bacteria produce toxins—powerful chemicals that damage cells and make a person ill. Other bacteria can directly invade and damage tissues. Common pathogenic bacterial infections are as follows: a) Strep throat caused by pathogenic Group A *Streptococcus*. b) Urinary tract infection usually caused by *Escherichia coli*. c) Food poisoning caused by Norovirus and *Salmonella*. d) Tuberculosis, a serious infectious disease that affects lungs and is caused by *Mycobacterium tuberculosis*. e) Lyme disease caused by *Borrelia* burgdorfer. It is transmitted to humans through the bite of infected blacklegged ticks. Typical symptoms include fever, headache, fatigue, and a characteristic skin rash called erythema migrans.

Bluetooth is a wireless technology standard for exchanging data over short distances for, e.g., using short-wavelength UHF radio waves in the ISM band from 2.4 to 2.485 GHz from fixed and mobile devices, and building personal area networks (PANS), etc. It is noted that other communication systems which transmit signals with messages from a user's device to recipients can be used as well. Wearable device Bluetooth can be used to connect to a mobile device, smartwatch, or other devices such as personal wellness, rooftop rain and wind weather stations, and so on.

A biohazard is a risk to human health or the environment arising from biological work, especially with microorganisms. Biohazard materials are infectious agents or hazardous biologic materials that present a risk or potential risk to the health of humans, animals, or the environment. The risk can be direct through infection or indirect through damage to the environment.

Biosafety is the application of safety precautions that reduce users' risk of exposure to a potentially infectious microbe or pathogen and limit contamination of the work environment and, ultimately, the community. Pathogens are mapped to biosafety level. The laboratory information system and microbiome mobile application allow for automated training and instruction on biosafety policies and procedures to minimize the occupational risk of exposure to infectious agents in the surrounding environment, in accordance with current local, county, state, and governmental recommendations regarding the biosafety levels for working with different organisms.

Biosafety levels (BSLs) or Biological Safety Levels: there are four biosafety levels. Each level has specific controls for containment of microbes or pathogens and biological agents. The primary risks that determine levels of containment are infectivity, severity of disease, transmissibility, and the nature of the work conducted. The origin of the pathogen or microbe, or the agent in question, and the route of exposure are also important. Each biosafety level has its own specific containment controls that are required for the following best waste collection practices, safety equipment, and facility construction. The biosafety level 1 for sample organisms like nonpathogenic strains of *E. coli, Staphylococcus, Bacillus subtilis*, and *Saccharomyces cerevisiae* does not require containment and has pathogen type agents that present minimal potential hazard to the user and the environment and are unlikely to cause disease. The biosafety level 2 for sample organisms like Influenza, HIV, Lyme disease, Equine Encephalitis, and COVID-19 requires containment and has pathogen type agents associated with human disease that pose moderate hazards to personnel and the environment but can cause severe illness in humans and are transmitted through direct contact with infected material. The biosafety level 3 for sample organisms like Yellow Fever, West Nile Virus, and Tuberculosis requires high containment and has pathogen type agents that present a potential for aerosol transmission, and agents causing serious or potentially lethal disease. The biosafety level 4 for sample organisms like Ebola Virus, Tick Borne Encephalitis, Marburg Virus, and Crimean-Congo hemorrhagic fever requires maximum containment and has pathogen type agents that pose a high risk of aerosol transmitted infections and life threating diseases. The biosafety levels 3 and 4 require the user to sterilize the nasal cavity, oral cavity, top of the surface, and environment. The detection and monitoring of pathogen biosafety level allows for implementation of appropriate sterilization and containment actions. The pathogen safety data sheet also provides the detail about the biosafety level. The biosafety information allows the user of the wearable device to take appropriate measures to reduce exposure to pathogens.

A biosensor is a device used to detect the presence or concentration of a biological analyte or element, such as a biomolecule, a biological structure, an antibody, a biomimetic, a cell, a DNA, an enzyme, a pathogen comprising a virus, a bacterium, and a fungus, a phage, a tissue, or a microorganism. It has a sensor that integrates a biological element with a physiochemical or optical transducer to produce an electronic signal proportional to a single analyte which is then conveyed to a detector. Biosensors consist of three parts: a component that recognizes the analyte and produces a signal, a signal transducer with an amplifier, and a reader device.

A camera is a component or device for recording visual images in the form of photographs, film, or video signals. A picocamera is a high-magnification and high-resolution camera made of picomaterials. Picocameras can have an artificial intelligence machine vision sensor with multiple functions, such as nasal cavity, oral cavity, and top of the surface recognition, line tracking, and so on. The intended use of the picocamera is to take photos and videos of the nasal cavity, oral cavity, or surface which can be used for nasal ID, open mouth ID, and surface ID recognition. The picocamera also takes images and videos of the small particles such as small molecules, proteins, microorganisms, and, and after image analysis identifies the microorganism type. The specialized picocamera can continually learn new surfaces such as top of the water, food, wall, table, and so on, even from different angles and in various ranges. The powerful picocamera optics can take high magnification and high-resolution images of the microorganisms. The more it learns, the more accurate it is when it is running its neural network algorithm. The picocamera is part of the microbial biosensor and particulate matter sensor, which also includes a flash. The picocamera is made of picomaterials, nanomaterials, and MEMS. To detect microorganisms clearly, the size of the wavelength should be considerably smaller, in the picometer and nanometer range. Gamma rays and X rays cannot be used because they are hazardous to humans. The wavelength of visible light is far larger than the small molecules, lipids, proteins, and microorganisms. The picocamera working principle involves passing the light rays through picofibers or picotubes, thereby by cutting or slicing and compressing them into multiple smaller excitation quanta (MSEQ). These excitation quanta are smaller than small molecules and strike the microorganisms. A picocamera lens using picofibers and picotubes takes all the excitation quanta bouncing around from the microorganisms and uses glass to redirect them to a single point, creating an image. The visible light can also be spliced when it strikes the nano structured metallic surface at the tip of the picofibers before it hits the particle. The picocamera sends real-time photo and video data files to the microbiome mobile application and cloud server.

A camera serial interface (CSI) is a specification of the Mobile Industry Processor Interface (MIPI) Alliance. It defines an interface between a picocamera and a single board computer (SBC). The high-speed protocol primarily is intended for point-to-point image and video transmission between cameras and host devices. Usually, it is in the form of a ribbon cable. The picocamera is connected to the single board computer (SBC) through a CSI cable.

Clinical performance is the ability of a device to yield results that are correlated with a particular clinical condition or a physiological or pathological process or state in accordance with the target population and intended user. The clinical performance comprises parameters, such as diagnostic sensitivity, diagnostic specificity, positive predictive value, negative predictive value, likelihood ratio, expected values in normal and affected populations.

A cloud server can involve deploying groups of remote servers and/or software networks that allow centralized data storage and online access to computer application software or resources. These groups of remote servers and/or software networks can be a collection of remote computing services. A cloud server can contain algorithms, methods, http web server, program logic, middleware stack, and databases. Wearable device data is stored locally in a secure digital card (SDC) and is also sent to the cloud server and stored in a database for further processing and can be accessed by the microbiome mobile application or laboratory information system.

A cell is the basic smallest structural, functional, and biological unit of all organisms. Cells are the smallest units of life, and hence are often referred to as the "building blocks of life." All living things are composed of cells. New cells are produced from the existing cell. The cell is the basic membrane-bound unit that contains the fundamental molecules of life and of which all living things are composed. Organisms typically consist of a cell, which is either prokaryotic or eukaryotic. Prokaryotes have cell membranes and cytoplasm but do not contain nuclei. The cells of eukaryotes contain nuclei. Cells may also be classified based on the number of cells that make up an organism, i.e., "unicellular," "multicellular," or "acellular." Cells make up tissues, tissues make up organs, and organs make up organ systems. The study of cells is called cellular biology, cell biology, or cytology. The branch of science that deals with microorganisms is called microbiology.

Clustering is a machine learning technique that involves the grouping of data points. It usually involves the grouping of similar things or people positioned or occurring closely together. For example, microorganisms' data from same genus and species but different variant can be clustered. Wearable devices can be clustered based on zip code, location, content type, and so on. Wearable devices sensor data can be clustered to predict and forecast the environmental conditions surrounding the user.

A database is a structured set of data held in a computer, especially one that is accessible in various ways. The software computing environment allows for various operations associated with wearable device data. Wearable device data is held in a structured manner in the database. The database includes tables and records for a wearable device, location, laboratory information system, laboratory testing facility, laboratory director, physician, system administration, external weather data, and so on. Predefined, agile models are created for which extra attributes can be added to the existing models. The program logic allows data definition operations like creating databases, files, groups, tables, views, and so on; data manipulation operations like creating, inserting, reading, updating, deleting data from objects; data control operations like grant, revoke, rollback, commit; and database maintenance operations like backup, restore, and rebuild. The program logic is responsible for getting the wearable device big data and performing standard database relational operations like select, project, join, product, union, intersect, difference, divide, and so on. The wearable device database consists of a microorganism database, pollen database, wearable device data, and user information data.

A display serial interface (DSI) specifies a high-speed differential signaling point-to-point serial bus. DSI is the hardware in the single board computer. The display serial interface defines a high-speed serial interface between a host processor and a display module. The display serial interface (DSI) standard allows for high-speed communication between Liquid Crystal Display (LCD) screens. DSI supports ultra-high definition such as 4K and 8K required by mobile displays. It specifies the physical link between the chip and display in devices such as smartphones, tablets, and connected cars. The DSI interface can be used to connect a capacitive touchscreen to the wearable device to display all the sensor data. It is usually in the form of connectors or ribbon cables. The DSI can be used to connect to the touchscreen for testing of the wearable device. The DSI port can connect to display unit. The DSI port connectors can be made available to connect to any smartwatch through a set of attachment slots in the smart band.

Deoxyribonucleic Acid (DNA) is a self-replicating material that is present in nearly all living organisms as the main constituent of chromosomes. It is the carrier of genetic information. DNA is the molecule that contains within it all the instructions and information about an organism. It is the chemical name for the molecule that carries genetic instructions in all living things. DNA contains information regarding how the organism will develop, how it lives and reproduces, and is described as the blueprint of a living organism. The DNA molecule consists of two strands that wind around one another to form a shape known as a double helix. Each strand has a backbone made of alternating sugar (deoxyribose) and phosphate groups. Attached to each sugar is one of four bases: adenine (A), cytosine (C), guanine (G), and thymine (T). The two strands are held together by bonds between the bases: adenine bonds with thymine, and cytosine bonds with guanine. The sequence of the bases along the backbones serves as instructions for assembling protein and RNA molecules. Given that DNA molecules are found inside the cells, they are too small to be seen with the naked eye. A microscope is needed. It possible to see the nucleus (containing DNA) using a light microscope. DNA strands/threads can only be viewed using microscopes that allow for higher resolution. A picocamera is a component of a particle imaging system that allows for high-magnification and high-resolution pictures of microorganisms and small molecules. The particle imaging system allows for detection of microorganisms based on DNA segments.

A dust mite is a microscopic organism that is the primary cause of allergies related to house dust. Dust mites work their way into soft places like pillows, blankets, mattresses, and stuffed animals. Many people with asthma are allergic to dust, but it's the droppings produced by the mites in the dust, along with the body fragments of dead dust mites, that really cause allergic reactions. The term "dust mite allergy" is a misnomer because it is the fecal excretion of these mites to which people are allergic. Dust mites can therefore trigger allergic reactions even when dead. When breathed in, these can lead a person to develop allergy or asthma symptoms. Dust mites are 0.5-50 μm in size, and a high efficiency particulate air (HEPA) filter can filter contaminants as small as 0.3 μm.

An enviro sensor consists of an RFID tag sensor, a location sensor, an ambient light sensor, a gas sensor, a smoke sensor, a temperature, humidity, and pressure sensor, a sound sensor, and an ultraviolet light sensor. It detects, measures, and monitors the surrounding environment sensor data.

A eukaryote is an organism with cells that contain a nucleus. In addition to a nucleus, a cell membrane, and cytoplasm, most eukaryote cells contain dozens of other specialized structures, called organelles, which perform important cellular functions. These organelles are mitochondria, plastids, endoplasmic reticulum, and Golgi apparatus. These organelles are not present in prokaryotic cells. The wearable device picocamera and particle imaging system can take pictures of organelles.

A fungus is a group of spore-producing single-celled or multinucleate organisms feeding on organic matter, including molds, yeast, mushrooms, and toadstools. A fungus is any member of the group of eukaryotic organisms which includes yeasts, rusts, smuts, mildews, molds, and mushrooms. Most microscopic or smaller fungi are 2 to 10 micrometers. The cell shapes include spherical, ellipsoidal, or cylindrical yeast cells or chains of highly polarized cylindrical cells which form pseudo hyphae or hyphae. There are lots of good or beneficial fungi to eat, like some mushrooms or foods made from yeast, like bread or soy sauce. Molds from fungi are used to make cheese, beer, and wine. Scientists use fungi to make antibiotics, which doctors sometimes use to treat bacterial infections. Fungi also help to decompose by releasing enzymes to break down the decaying material, after which they absorb the nutrients in the decaying material, from leaves to insects. Fungi can cause disease in many ways, for example: a) Replication of the fungus such that fungal cells can invade tissues and disrupt their function, b) Immune response by immune cells or antibodies, c) Competitive metabolism by which they consume energy and nutrients intended for the host, d) Toxic metabolites, for example, *Candida* species that can produce acetaldehyde, a carcinogenic substance, during metabolism. Fungi are linked to human ailments, such as allergic and asthmatic diseases that affect millions of people. Some fungi reproduce through tiny spores in the air. Inhaled spores result in fungal infections which often start in the lungs or on the skin. Fungi cause eye infections which can result in blindness. Fungi create harm by spoiling food, destroying timber, and by causing diseases of crops, livestock, and humans. Only a few of the fungi cause sickness and infection. Common fungal infections are as follows: a) Ringworm, which is a contagious fungal infection caused by common mold-like parasites that live on the cells in the outer layer of the skin. Types of fungi that cause ringworm are *Trichophyton, Microsporum*, and *Epidermophyton*. b) Fungal nail infections and athlete's foot (tinea pedis), a fungal infection that usually begins between the toes caused by dermatophytes. Athlete's foot is caused by several different fungi, including species of *Trichophyton, Microsporum*, and *Epidermophyton*. c) Mouth, throat, esophagus, and vaginal yeast infections caused by the yeast *Candida*. The biohazards associated with different fungi can be reported in the form of biosafety level. The biosafety level allows the user and physician to take appropriate preventive measures to sterilize the fungus.

A gas sensor is an electronic component that can be used to detect the presence or concentration of gases. The sensor has different sensitivities to different types of gases in the ambient air. The intended use of the gas sensor is to detect, measure, and monitor gas types such as reducing gases with low oxidation numbers, such as carbon monoxide (CO), ammonia ($NH_3$), ethanol ($C_2H_5OH$), hydrogen (H), methane ($CH_4$), propane ($C_3H_8$), and isobutane ($C_4H_{10}$) Oxidizing gases generally provide oxygen, cause, or contribute to the combustion of other material more than air does. They include nitrogen dioxide ($NO_2$), nitrogen oxide (NO), and hydrogen (H). Gases that react to ammonia include hydrogen (H), ethanol ($C_2H_5OH$), ammonia ($NH_3$), propane ($C_3H_8$), and isobutane ($C_4H_{10}$), either inside or surrounding the user. The gas type information can be used by the user or physician to take appropriate actions such as removal of toxic gases or evacuation based on set acceptance criteria. The gas types of information surrounding the user can also be used by the user to take appropriate preventive measures by wearing appropriate personal protective equipment. The gas type can also provide information about potential fire hazards due to the presence of highly flammable gases like methane. Improperly managed harmful gases can serve as a rich source of disease and contribute to global climate change through the generation of greenhouse gases, and even promote urban violence with the degradation of urban environments. The detection of gas is expressed as a gas type present. The gas sensor sends real-time gas types surrounding the user data to the cloud server. The gas sensor working principle can be based on variation to the electrical resistance or capacitance in response to the concentration of the gas. In the case of electrical resistance type, the concentration of the gas near the sensor produces a corresponding potential difference by changing the resistance of the material inside the sensor, which can be measured as output voltage. Based on this voltage value, the type and concentration of the gas can be estimated. The gas type which the sensor can detect depends on the sensing material present inside the sensor. Gas sensors are typically classified based on the type of the sensing element they are built with (i.e., a metal oxide based gas sensor uses the measurement of change in resistance, a fluorescence gas sensor uses the detection of wavelength change of fluorescence, an optical gas sensor detects gas types based on spectral range, an electrochemical gas sensor is operated based on the diffusion of gas of interest into the sensor, a capacitance-based gas sensor uses changes in the capacitance value to detect gas types, and calorimetric gas sensors and acoustic based gas sensors are based on a change in the resonant frequency). The most common gases found in home or work areas are carbon monoxide, ammonia, chlorine, methane, carbon dioxide, nitrogen, hydrogen sulfide, and hydrogen.

General purpose input output pins, also known as GPIO pins, are uncommitted digital signal pins on an integrated circuit or electronic circuit board whose behavior—including whether they act as input or output—is controllable by the user at run time. GPIOs have no predefined purpose and are unused by default. Sensor software drivers are used to map and assign the GPIO to the sensor pinout. Microbial biosensor, particulate matter sensor, enviro sensor, and display unit pinouts are connected to single board computer GPIO pins.

A global positioning system (GPS) is a satellite-based navigation system made up of at least 24 satellites. GPS works in any weather condition, anywhere in the world, 24 hours a day, with no subscription fees or setup charges. A GPS measures elevation below the orbit of the satellites. To convert this to altitude, it subtracts the distance from the center of the earth (i.e., center of the satellites' orbits) from the average sea level. It provides geospatial position data which can be mapped to street addresses and altitudes. The geospatial position data allows for tracking of wearable device location.

A graphics processing unit (GPU) is a specialized electronic circuit designed to rapidly manipulate and alter memory to accelerate the creation of images in a frame buffer intended for output on a display device. A GPU is one of the components of a system on chip of a single board computer. The GPU accelerates the processing of picocamera photos and videos for multiple functions, such as microorganism recognition, particulate matter size, object ID recognition, surface type recognition, and so on.

A gyroscope can be used for measuring or maintaining the orientation and angular velocity of the wearable device. The orientation allows centering of the wearable device to an object like a nasal cavity, an oral cavity, or a surface.

A haptic technology can interface with the user through the sense of touch. A wearable device touchscreen is touch sensitive.

A humidity sensor is an electronic component that detects and measures water vapors. The intended use of the humidity sensor is to detect, measure, and monitor the relative humidity surrounding the user. The wearable device humidity value can be used by the user of a wearable device to ensure that humidity is within set acceptance criteria. It is very important to reduce the high moisture content; otherwise, it can also result high microbial activity and could even facilitate growth of pathogens, foul odor, unpleasant smell, and infectious diseases. Dust mites thrive in temperatures of 20 to 25 degrees Celsius. Dust mites also like humidity levels of 70 to 80 percent. The unit of measurement of the results of the humidity sensor can be a percentage of relative humidity surrounding the user. The humidity is reported in the form of a percentage that runs from 0 to 100. The humidity sensor sends real-time humidity data surrounding the user to the cloud server. The humidity sensor detects the relative humidity of the immediate environments in which it is placed. It measures both the moisture and temperature in the air and expresses relative humidity as a percentage of the ratio of moisture in the air to the maximum amount that can be held in the air at the current temperature. The working principles of the humidity sensor can be based on capacitive humidity sensors, resistive humidity sensors, thermal conductive sensors, and such. A nano and MEMS relative humidity sensor is a differential capacitance type that consists of a layer sensitive to water vapor that is sandwiched between two electrodes acting as capacitor plates. The upper water vapor permeable electrode consists of a grid that allows water vapor to pass into the humidity sensitive polymer layer below, which is a backplate electrode, thus altering the capacitance between the two electrodes. The above units are on top of a base substrate. On-chip circuits carry out automatic calibration and signal processing to produce a relative humidity measurement.

Illuminance is the amount of luminous flux per unit area. The unit for the quantity of light flowing from a source in any one second or luminous flux is called the lumen. In a sensor, the unit of measurement is the lux, which is equal to one lumen per square meter.

An LED flash is an electronic component device that emits light when charged with electricity. LEDs come in white and many colors, including non-visible light such as infrared and ultraviolet. Bright white LEDs are commonly used for phone camera flashes and LCD display backlights. The LED flash is part of the picocamera.

A laboratory director is a person responsible for the overall operation and administration of the laboratory, including provision of timely, reliable, and clinically relevant test results and compliance with applicable regulations and accreditation requirements. The responsibility also includes employment of competent personnel, test validations, availability of equipment and consumables, safety, laboratory policies, quality assurance, proficiency testing, and test reports. The laboratory director reviews patient test data and determines the cause of disorders and reports out user test results. The laboratory director routes the critical value test results such as pathogen and abnormal patient test results to report to the physician and patient.

A laboratory information system (LIS) or laboratory information management system (LIMS) have a local or cloud system comprising of computer hardware and software serving the information needs of the laboratory. The laboratory database contains all the information for patient specimen accessioning, pre-analytical, analytical, and post analytical testing, and quality control information. Laboratory director reviews the patient result in the laboratory information system before reporting the results out to physician.

A laboratory testing facility includes a clinical laboratory, biorepository, healthcare facility, water testing facility, food testing facility, forensic testing facility, and so on. A healthcare facility provides a wide range of laboratory procedures which aid the physicians in carrying out the diagnosis, treatment, and management of patients. The water and food testing facilities test for pathogens in water, liquids, and food. The forensic testing facility tests involve pathology tests associated with crime.

A location sensor is an electronic component that can determine and monitor the geospatial position which includes latitude, longitude, and altitude, or the street location of an object, and provide internet access. The intended use of the location sensor is to determine the geospatial location of a wearable device and provide internet access to a wearable device. The information can also include time and other data. The wearable device location value can be used to associate the sensor data with the location. It can consist of global positioning system (GPS) receivers and cellular adapter elements. The location sensor working principle can be based on GPS and cellular network internet connectivity. The GPS is a satellite-based navigation system that provides geolocation and time information to a GPS receiver anywhere on or near the Earth where there is an unobstructed line of sight to four or more GPS satellites. The GPS part of location sensors are receivers with antennas that use a satellite-based navigation system with a network of satellites in orbit around the Earth to provide position, velocity, and timing information. A cellular adapter part of the location sensor enables cellular internet connectivity. The location sensor sends real-time data to the cloud server. The wearable device location information can be used to track it through connected mobile devices.

Machine learning can be a method of data analysis that automates analytical model building. Machine learning is a branch of artificial intelligence that uses statistical techniques to give computer systems the ability to learn from data, without being explicitly programmed. Example machine learning techniques that can be used herein include, inter alia: decision tree learning, association rule learning, artificial neural networks, inductive logic programming, support vector machines, clustering, Bayesian networks, reinforcement learning, representation learning, similarity, metric learning, and/or sparse dictionary learning. Historical user sensor data sets can be used as training data sets. Machine learning, along with neural network algorithms, can continually learn to recognize new objects like food, liquids, paper, containers, cardboard boxes, and such, from different angles and in various ranges from the photos and videos taken by the picocamera. Machine learning can also learn and predict pathogens on surfaces of different type of objects. The more learning, the more accurate the prediction, thereby increasing the accuracy of the results. Machine learning algorithms of the wearable devices allow for identification of the microorganisms, pollens, and other particulate matter.

Magnetism can be a physical phenomenon produced by the motion of an electric charge, resulting in attractive and repulsive forces. A magnet can be piece of iron that has its component atoms so ordered that the material exhibits properties of magnetism, such as attracting other iron-containing ferromagnetic materials such as iron, cobalt, nickel, and gadolinium. A magnetic field is a vector field that describes the magnetic influence on moving electric charges, electric currents, and magnetic materials. Magnetic fields surround magnetized materials and are created by electric currents such as those used in electromagnets, and by electric fields varying in time. Since both the strength and direction of a magnetic field may vary with location, they are described as a map assigning a vector to each point of space. Magnetic fields are produced by moving electric charges and the intrinsic magnetic movements of elementary particles associated with a fundamental quantum property, their spin. The electromagnetic waves method uses a Hall sensor array to detect microorganisms containing ferromagnetic material. A Hall sensor is a type of sensor which detects the presence and magnitude of a magnetic field using the Hall effect. The output voltage of a Hall sensor is directly proportional to the strength of the field. The effect of Earth's electromagnetic waves is masked out to increase the accuracy of the results.

Methane is a gas byproduct generated through the natural decomposition of solid waste in landfills. Methane is an odorless and flammable gas. When present in very high concentrations, it can be potentially explosive. Methane is nonreactive and not harmful to human health, but if there is excess methane in a room and it displaces the oxygen, one could die from suffocation. The user should leave the area immediately if there is excessive methane gas in the surrounding area. Excessive methane gas is linked to global warming. There is a type of beneficial bacteria, methanotrophs, which hold the key to dismantling methane gas. Methanotrophs survive extreme conditions by eating methane.

A method can be a particular procedure for accomplishing a task or activity. Wearable devices, various other sensors, and software computing environments use methods and algorithms to set specific acceptance criteria to detect and sterilize pathogens and monitor the environment. A method can implement many algorithms. A wearable device can have sensor methods to implement, operate, calculate, and monitor pathogens, pollens, and the environment. Software computing environments can contain pathogen detection and sterilization methods. Microorganisms can be detected through particle detection methods such as infrared spectroscopy, fluorescence imaging, particle imaging, nucleic acid sequence identification, electromagnetic waves, ultrasound waves, light scattering, and so on.

Micro-electromechanical systems (MEMS) devices contain tiny integrated devices or systems that combine mechanical and electrical components. They now also include nanomaterials and picomaterial based components. They are fabricated using integrated circuit (IC) batch processing techniques and can range in size from a few micrometers to millimeters. MEMS devices combine small mechanical and electronic components on a silicon chip. The fabrication techniques used for creating transistors, interconnects, and other components on an integrated circuit (IC) can also be used to construct mechanical components such as springs, deformable membranes, vibrating structures, valves, gears, and levers. This technology can be used to make a variety of sensors such as microbial biosensors, particulate matter sensors, enviro sensor comprising RIFD tag sensors, location, temperature, humidity, pressure, air quality, smoke, gas, ambient light, and so on. MEMS enables the combination of accurate sensors, powerful processing, and wireless communication (for example, Wi-Fi or Bluetooth) on a single integrated circuit. Large numbers of devices can be made at the same time, so they benefit from the same scaling advantages and cost efficiencies as traditional ICs. MEMS based sensors allow for the manufacturing of compact and power efficient wearable devices. The microbial biosensor, particulate matter sensor, and enviro sensor are very small MEMS devices that fit on a wrist smart band.

A microorganism, or microbe, is an organism that is microscopic or submicroscopic, which may exist in its single-celled form or a colony of cells. A microscopic organism is usually a prion, virus, bacterium, fungus, protist, or dust mite. The study of microorganisms is called microbiology. Prions and viruses are non-living but are usually considered part of microorganisms. The microorganisms can be beneficial or harmful to humans. The exact number is not known, but there are about one trillion species of microbes on Earth, and 99.999 percent of them have yet to be discovered. Viruses are considered neither prokaryotes nor eukaryotes because they lack the characteristics of living things, except the ability to replicate in host cell. Bacteria are prokaryotes, i.e., microscopic single-celled organisms that have neither a distinct nucleus with a membrane nor other specialized organelles. In contrast, fungi and dust mites are eukaryote organisms consisting of a cell or cells in which the genetic material is DNA in the form of chromosomes contained within a distinct nucleus. Microorganisms can be good or beneficial for humans, such as microbes that contribute to digestion, produce vitamins, promote development of the immune system, and detoxify harmful chemicals. Microorganisms or microbes are essential to making many foods we enjoy, such as bread, cheese, and wine. Microorganisms or microbes that cause disease are called pathogens.

A microphone is a device that converts the air pressure variations of a sound wave to an electrical signal. The wearable device microphone and speaker allow users near the wearable device two-way communication with a person on the mobile device through the microbiome mobile application or laboratory information system. The microphone can be used as an input for voice activated commands.

A microprocessor is an integrated circuit that contains all the functions of a central processing unit of a computer.

A microscope is an optical instrument used for viewing very small objects, such as animal or plant cells, or large microorganisms, typically magnified several hundred times. The limit of resolution for a light microscope is 0.2 µm or 200 nm, and most viruses are smaller than that. As such, an electron microscope is needed. An electron microscope is a microscope with high magnification and resolution, employing electron beams in place of light and using electron lenses. The electron microscopes have a higher resolving power than light microscopes and can reveal the structure of smaller objects such as viruses, bacteria, and fungi. An electron microscope can have magnifications of up to about 10,000,000×, whereas most light microscopes are limited by diffraction to about 200-nm resolution and useful magnifications below 2,000. The electron microscope types usually are Transmission Electron Microscope (TEM), Scanning Electron Microscope (SEM), Reflection Electron Microscope (REM), Scanning Transmission Electron Microscope (STEM), and Scanning Tunneling Microscopy (STM). Atomic force microscopy (AFM) is a kind of scanning probe microscopy, where a probe or tip is used to map the contours of the sample. These instruments are bulky, costly, and require an experienced person to look at magnified images. To view the DNA, RNA, as well as a variety of other protein molecules, an electron microscope is used. Whereas the typical light microscope is only limited to a resolution of about 0.25 µm, the electron microscope is capable of resolutions of about 0.2 nanometers, which makes it possible to view smaller molecules. This is achieved because electron microscopes use electron beams rather than the visible light used for light microscopes. Existing microscopes require sample to be put on substrates like glass, are very bulky, and require a special room and light. The electron or e-beam is like X rays and gamma radiation and ionizes the material it strikes by stripping electrons from the atoms of the exposed surface and is damaging to the humans and microorganisms. The wearable device picocamera instead uses MEMS and a picomaterials based specialized magnifying lens, aperture, and auto adjustment of the image or video and objective. The optical micro, nano, and picomaterials enable super high magnification and resolution biological imaging and video of microorganisms using visible light that is compressed and not harmful to humans or environment. Picomaterials have diameters in the picometer range. Picofibers have fibers with diameters in the picometer range, and nanofibers are fibers with diameters in the nanometer range. Picofibers and nanofibers can be generated from different polymers. The picocamera hardware uses picomaterials.

A microbial biosensor is a device that detects microorganisms. Microorganisms detected include both beneficial microorganisms and pathogenic microorganisms also known as pathogens. A microbial biosensor is an electronic component that utilizes optical, mass based, and acoustic sensors to detect microorganisms and kill pathogens. The intended use of the microbial biosensor is to detect, measure, and monitor pathogen types, concentrations, and biosafety levels, and kill pathogens in a nasal cavity, an oral cavity, or on a surface of the object. The microbial biosensor also detects, measures, and monitors a beneficial microorganism count, a beneficial microorganism type, and a beneficial microorganism concentration in a nasal cavity, an oral cavity, or on a surface of the object. The microorganisms detected can be prions, viruses, bacteria, fungi, protists, dust mites, and so on. Pathogens of all classes must have mechanisms for entering their host and for evading immediate destruction by the host immune system. Pathogens that are most contagious and cause the most severe symptoms are SARS-CoV-2, *E. coli*, Hepatitis A, Nontyphoidal *Salmonella, Norovirus, Shigella*, and *Salmonella Typhi*. Software computing environments can contain pathogen detection and sterilization methods. Microorganisms can be detected through particle detection methods such as infrared spectroscopy, fluorescence imaging, particle imaging, nucleic acid sequence identification, electromagnetic waves, ultrasound waves, light scattering, and so on.

A microbiome mobile application is a computer program or software application, or an app designed to run on a wearable device to set up a wearable device and access the sensor data. The microbiome mobile application can also be installed on the smartwatch and mobile devices. The microbiome mobile application retrieves public, private, and commercial pathogen annotation information stored in a microorganism database and pollen database. The microbiome mobile application, microorganism database, and pollen database reside in the secure digital card of the single board computer. In a system software computing environment, they are also stored in the cloud server database for global access.

A microorganism database stores the platform dataset, genome, annotation, pathogen safety data sheet, attributes, and unique identifiers based on biosensor transducers and the microorganism detection method used. The taxonomy data comprises pathogen kingdom, phylum, class, order, family, genus, species, and so on. The genomic information contains organism name, organism groups, gene assembly, assembly level, length of genome assembly, GC %, host, protein coding genes, neighbor nucleotides, cell type, number of cells, size, microscopy, shape, cellular machinery, type of organism, structure, cell wall, cellular membrane, genome (DNA or RNA), strand type (single, double), nucleic acid, mRNA, ribosomes, living attributes, replication, cells infected, diseases/infections, duration of illness, treatment, and so on. The pathogen safety data sheet contains information such as infectious agent, hazard identification, dissemination, stability, and viability, first aid/medical, laboratory hazards, exposure controls/personal protection, handling and storage, and regulatory and other information. The microorganism attributes comprise structure, morphology, component, function, chemical composition, constituent or element, and so on.

A middleware stack is software that lies between an operating system and the applications running on it. A middleware stack functions as a hidden translation layer and enables communication and data management for distributed applications. It connects two applications together so data and databases can be easily passed between them. For example, middleware allows users to perform such requests, allowing the web server to return dynamic web pages based on a user's profile, or submitting forms on a web browser. The microbiome mobile application and laboratory information system dynamic web pages interface with the middleware stack to send and fetch the data and display it on the web browser.

A model can be a system or thing or procedure or a proposed structure used as an example to follow. Models are created for methods like clusters based on microorganism types, pathogen types, shape, size, composition, wearable device location, and zip codes. Models are also created for the wearable device database structure to contain all the wearable device information.

A nasal cavity is a large, air-filled space above and behind the nose in the middle of the face. The nasal septum divides the cavity into two cavities, also known as fossae. Each cavity is the continuation of one of the two nostrils. The origin of organisms that are introduced into the sinuses and may eventually cause sinusitis is the nasal cavity. The normal flora of that site includes *Staphylococcus aureus, Staphylococcus epidermidis*, Streptococci, *Propionibacterium acnes*, and aerobic diphtheroid. The most common aerobic bacteria are *Staphylococcus epidermidis*, diphtheroids, and *Staphylococcus aureus*. The wearable device nasal cavity detection can be based on the entire nasal cavity measurement area or can be programmed to look for microorganisms in a specific area within the nasal cavity. Individual user nasal cavity can be profiled and setup initially. This allows for masking the nasal cavity tissues for faster detection of microorganisms. The particle detection methods are programmed to first do the comparison of detected microorganisms with the commonly found microorganisms in the nasal cavity. Also, based on enviro sensor data, some of the microorganisms are not present in the nasal cavity and can be ruled out during microorganism detection.

Nucleobases, also known as nitrogenous bases or often simply bases, are nitrogen-containing biological compounds that form nucleosides, which, in turn, are components of nucleotides, with all these monomers constituting the basic building blocks of nucleic acids. The ability of nucleobases to form base pairs and to stack one upon another leads directly to long-chain helical structures such as ribonucleic acid (RNA) and deoxyribonucleic acid (DNA). Five nucleobases—adenine (A), cytosine (C), guanine (G), thymine (T), and uracil (U)—are called primary or canonical. They function as the fundamental units of the genetic code, with the bases A, G, C, and T being found in DNA while A, G, C, and U are found in RNA. Thymine and uracil are distinguished merely by the presence or absence of a methyl group on the fifth carbon (C5) of these heterocyclic six-membered rings. Adenine and guanine have a fused-ring skeletal structure derived of purine; hence they are called purine bases. The simple-ring structure of cytosine, uracil, and thymine is derived of pyrimidine, so those three bases are called the pyrimidine bases. Each of the base pairs in a typical double-helix DNA comprises a purine and a pyrimidine: either an A paired with a T or a C paired with a G. These purine-pyrimidine pairs, which are called base complements, connect the two strands of the helix and are often compared to the rungs of a ladder. The super sensitive picocamera based on picomaterials, capable of registering single electrons, is used to take high-resolution images of the DNA and RNA, which includes base molecules. Bases are identified based on the A, G, C, T, and U bond structures.

An oral cavity or open mouth cavity is the lining inside the cheeks and lips, the front two thirds of the tongue, the upper and lower gums, the floor of the mouth under the tongue, the bony roof of the mouth, and the small area behind the wisdom teeth. The oral cavity flora is home many microorganisms. The presence of nutrients, epithelial debris, and secretions makes the mouth a favorable habitat for a great variety of bacteria, including both beneficial and pathogens. Oral bacteria include *streptococcus*, granulicatella, gemella, *veillonella*, lactobacilli, staphylococci, and corynebacteria, with a great number of anaerobes. Anaerobes such as *Treponema denticola* and *Porphyromonas gingivalisoral* cause diseases such as periodontitis. In addition, specific oral bacterial species have been implicated in several systemic diseases, such as bacterial endocarditis, aspiration pneumonia, osteomyelitis in children, preterm low birth weight, and cardiovascular disease. The wearable device oral cavity detection can be based on the entire open mouth measurement area or can be programmed to look for microorganisms in specific area within the oral cavity. Individual user oral cavity can be profiled and setup initially. This allows for masking the oral cavity tissues for faster detection of microorganisms. The particle detection methods are programmed to first do the comparison of detected microorganisms with commonly found microorganisms in the oral cavity. Also, based on enviro sensor data, some of the microorganisms are not present in the oral cavity and can be ruled out during microorganism detection.

An organelle is a specialized structure that performs important cellular functions within a eukaryotic cell. Examples of membrane-bound organelles are nucleus, endoplasmic reticulum, Golgi apparatus, mitochondria, plastids, lysosomes, and vacuoles.

Particulate matter concentrations refer to the amount of fine particulate matter in the air. Particulates, also known as atmospheric aerosol particles, bioaerosol particles, atmospheric particulate matter, particulate matter (PM), suspended particles in the air, or suspended particulate matter (SPM)—are microscopic particles of solid or liquid matter suspended in the air. The term aerosol commonly refers to the particulate/air mixture. Particulates are the most harmful form of air pollution due to their ability to penetrate deep into the nasal cavity, lungs, blood stream, and brain, causing health problems including heart attacks, respiratory disease, and premature death. Bioaerosols (short for biological aerosols) are a subcategory of particles released from terrestrial and marine ecosystems into the atmosphere. They consist of both living and non-living components, such as prions, viruses, bacteria, fungi, protists, dust mites, and pollen.

A particulate matter sensor is an electronic component which can be used to obtain the number of suspended particles in the air, i.e., the concentration of particles, and output it in the form of a digital interface. The intended use of the particulate matter sensor is to detect, measure, and monitor the air quality index value surrounding the user, and it can be used to provide the level of health concern information. The wearable device air quality index value can be used by the user to decontaminate or use personal protective equipment based on set acceptance criteria. The air quality index value is reported in the form of a number that runs from 0 to 500. The EPA Office of Air Quality Planning and Standards (OAQPS) has set National Ambient Air Quality Standards. The particulate matter sensor sends real-time air quality information, i.e., the concentration of particles data, to the cloud server. The detected suspended particles in the air can include microorganisms, pathogens, dust, dust mites, pollens, and so on. The particulate matter sensor can use the laser scattering principle, which produces scattering by using a laser to radiate suspending particles in the air, collects scattering light in a certain degree, and finally obtains the curve of the scattering light change with time. In the end, the equivalent particle diameter, and the number of particles with different diameters per unit volume, can be calculated by a microprocessor based on the MIE theory of absorption and scattering of plane electromagnetic waves by uniform isotropic particles of the simplest form. The MIE theory is an analytical solution of Maxwell's equations for the scattering of electromagnetic radiation by particles of any size. The particulate matter sensor can distinguish types of particulate matter. PMx defines particles with a size smaller than "x" micrometers (e.g., PM2.5=particles smaller than 2.5 μm); PM.001, PM.01, PM.1, PM1, PM2.5, and PM10 in both standard and environmental units, and numbers of particles of various sizes: >0.001, >0.01, >0.1, >0.3, >0.5, >1.0, >2.5, >5, and >10 μm. The particulate matter unit of measurement is $μg/m^3$ or $ng/m^3$.

A pathogen is a prion, virus, bacterium, fungus, protist, dust mite, or other microorganism that can cause disease. Pathogens are disease-causing microorganisms and non-living things such as viruses. In total, there are approximately 1,400 known species of human pathogens that includes viruses, bacteria, and fungi. Human pathogens account for much less than 1% of the total number of microbial species on the planet. There are about 220 virus species that are known to be able to infect humans. The pathogenic viruses are known to cause disease in humans, and all can break into human cells. There are more than 900 bacteria species that are known to cause disease in humans. Pathogenic fungi are fungi that cause disease in humans or other organisms. Approximately 300 fungi are known to be pathogenic to humans.

A pathogen count is the total number of distinct prions, viruses, bacteria, fungi, protists, dust mites, or other microorganisms.

A pathogen type can be a type of prion, virus, bacterium, fungus, protist, dust mite or other microorganism. For example, a type of virus can be Influenza A/B virus, Rhinovirus, SARS-CoV-2 virus or COVID-19 virus, HIV, Smallpox, and so on. A type of bacteria can be *Legionella pneumophila, Mycobacterium tuberculosis, Staphylococcus aureus*, and so on. A type of fungus can be *Histoplasma capsulatum, Aspergillus flavus, Blastomyces dermatitidis*, and so on.

A pathogen concentration refers to the number of pathogen particulate matter in the air.

A pathogen biosafety level measurement is based on biological safety levels.

A physician is a person qualified to practice medicine. A physician can diagnose a disease based on pathogen type and prescribe applicable medication. The physician reviews patient test results in conjunction with physiological data and determines the root cause of the disorder to treat the user.

A platform dataset comprises a set of reference microorganism, microbiome, microbial genome, pathogen data, pollen genome, and pollen data from publicly available sources that constitutes the framework within which microorganism beneficial, pathogenic, and pollen data information is handled by the platform. The platform dataset can be derived from National Center for Biotechnology Information (NCBI), European Molecular Biology Laboratory/European Bioinformatics Institute (EMBL-EB), MicrobeNet—Centers for Disease Control and Prevention (CDC), Pathosystems Resource Integration Center (PATRIC), Virus Pathogen Resources (ViPR), Fungi Database (FungiDB), and the Ensembl genome browser, which provides access to organized information from the analysis of biological data for prions, virus, bacteria, fungi, protists and so on, and pollen data from National Centers for Environmental Information. The actual sources, versions, genome build(s), and external links per platform dataset version are available in the microbiome mobile application user interface. The platform dataset curation can add or delete the references to dataset. A version number is assigned to platform dataset based on existing public database content. A new version of the platform dataset is created to incorporate new data available in the public databases. The updated data can include addition of new microorganisms and pathogens. The platform dataset version used by the microbiome mobile application can be selected by a user.

A pollen is a fine powdery substance, usually yellow, consisting of microscopic grains discharged from the male part of a flower or from a male cone. Each grain contains a male gamete that can fertilize the female ovule, to which pollen is transported by the wind, insects, or other animals. Pollen is produced by the anther of flowering plants. Each pollen grain contains a gametophyte that can produce sperm to fertilize an egg within the female part of the flower—the pistil. Pollen is a common name for the male gametophyte of seed plants. It can be all pollen or a single pollen grain. Pollen can also be a mass of microspores in a seed plant appearing usually as a fine dust.

A pollen grain is a structure that contains entire male gametes in seed plant. A pollen grain is one of the granular microspores that occur in pollen and give rise to the male gametophyte of a seed plant. A pollen grain is a microscopic body that contains the male reproductive cell of a plant. Pollen grains are microscopic structures that carry the male reproductive cell of plants. The inside of the grain contains cytoplasm along with the tube cell (which becomes the pollen tube) and the generative cell (which releases the sperm nuclei). The outer shell is made of two layers. The inside layer intine (interior) is composed partly of cellulose, a common component in the cell walls of plant cells. The outer layer is known as the exine (exterior). This highly sophisticated and complex outer layer is rich in a compound known as sporopollenin. A pollen grain seen through a microscope displays an extremely durable body and has a tough outer coating. This hardy coat offers great protection from the harsh outdoor environment. This is important because inside this tough shell lie two cells: the tube cell, which will eventually become the pollen tube, and a generative cell, which contains the male sperm nuclei needed for fertilization. Pollen grains are microscopic particles, typically single cells, of which pollen is composed. Pollen grains have a tough coat that has a form characteristic of the pollen-producing plant. Pollen grain is a structure produced by plants containing the male haploid gamete to be used in reproduction. Each pollen grain contains vegetative (non-reproductive) cells (only a single cell in most flowering plants but several in other seed plants) and a generative (reproductive) cell. In flowering plants the vegetative tube cell produces the pollen tube, and the generative cell divides to form the two sperm nuclei. Angiosperms are flowering plants that have seeds inside a protective chamber called an ovary. Gymnosperms are plants that produces seeds that are exposed rather than seeds enclosed in fruits. Pollen grains are produced by seed plants (angiosperms and gymnosperms), and spores by fungi, bacteria, ferns, lycopods, horsetails, and mosses.

Pollination is the transfer of pollen from the male reproductive structure gametophyte to the female reproductive structure gametophyte. Most gymnosperms and some angiosperms are wind pollinated, whereas most angiosperms are pollinated by animals.

A pollen allergy is a damaging immune response by the body caused by pollen or dust in which the mucous membranes of the eyes and nose are itchy and inflamed, causing a runny nose and watery eyes. The symptoms are usually sneezing, nasal congestion, runny nose, watery eyes, itchy throat and eyes, and wheezing. The pollen allergy level is reported as very high, moderate, or very low. It can also report as low (0-2.4), low-med (2.5-4.8), medium (4.9-7.2), med-high (7.3-9.6), and high (9.7-12). The pollen allergy level can be set in the microbiome mobile application.

A pollen count is the measurement of the number of pollen grains in a cubic meter of air. High pollen counts result in increased rates of pollen allergic reaction for people with allergic disorders. The pollen count can be reported as number or qualitative value as very low, low, moderate, high, very high, extreme.

The pollen type reported can be grass, tree, and weed. Grass pollen causes a runny nose and other hay fever symptoms. In North America, grass pollen generally affects people from mid-May to July. The types of grasses that are most likely to cause allergy symptoms are Orchard, Sweet Vernal, Bermuda, Rye, and so on. Tree pollens occur during different times of the year. The trees that are most likely to cause allergy symptoms include Oak, Birch, Cedar, Willow, Ash, Aspen, Cottonwood, Mulberry, Beech, and so on. Weed pollen is most likely to cause hay fever. The following weeds most likely to cause allergy symptoms include Sagebrush, Tumbleweeds, Pigweed, Burning Bush, Russian Thistle, and so on.

A pollen database stores the pollen type, subtype, type of allergy, symptoms, medication, location, history, and pollen safety data sheet related information.

A pressure sensor is an electronic component that can be used to measure atmospheric or air pressure in environments. The intended use of the pressure sensor is to detect, measure, and monitor air pressure or simply pressure surrounding the user. The wearable device air pressure value can be used by a physician to associate a medical condition associated with pressure based on set acceptance criteria. The unit of measurement of pressure is reported in pascal units, or in short, kilopascal (kPa). It is also reported as hPa which is the abbreviated name for hectopascal (100×1 pascal) pressure units which are exactly equal to millibar pressure unit (mb or mbar). The pressure sensor sends real-time wearable device pressure data surrounding the user to the cloud server. In older days, mercury and aneroid barometers were used to measure the pressure. The working principle of a pressure sensor can use membranes, thin plates, piezo resistive sensors, capacitive sensors, optoelectronic pressure sensors, and so on. The modern-day barometer uses MEMS technology, making it capable of measuring atmospheric pressure in a small and flexible structure. The pressure sensor sends real-time data to the cloud server. The landfill and wearable device methane and other gas emissions are strongly dependent on changes in barometric pressure; the rising barometric pressure suppresses the emission while the falling barometric pressure enhances the emission, a phenomenon called barometric pumping. Lower pressure will result in more gas seeping out from landfills and waste bins, and into the air. Microorganisms that require high atmospheric pressure for growth are called barophiles. The bacteria that live at the bottom of the ocean are able to withstand great pressures. Exposure to high pressure kills many microbes. In the food industry, high-pressure processing (also called pascalization) is used to kill bacteria, yeast, molds, parasites, and viruses in foods while maintaining food quality and extending shelf life. High pressure can be used to sterilize or kill pathogenic microorganisms in a nasal cavity, or an oral cavity, or a surface.

A prion is a type of protein that can cause disease in humans and animals by triggering normally healthy proteins usually in the brain to fold abnormally. Prions are misfolded proteins with the ability to transmit their misfolded shape onto normal variants of the same protein. Prions are smaller than viruses. Prions are also unique since they do not contain nucleic acid, unlike bacteria, fungi, viruses, and other pathogens. Prion diseases include Creutzfeldt-Jakob disease (CJD) in humans, bovine spongiform encephalopathy (BSE or "mad cow" disease) in cattle, scrapie in sheep, and chronic wasting disease (CWD) in deer, elk, moose, and reindeer. Human prion diseases comprise: a) Creutzfeldt-Jakob Disease (CJD)—It is a rapidly progressive, invariably fatal neurodegenerative disorder believed to be caused by an abnormal isoform of a cellular glycoprotein known as the prion protein; b) Variant Creutzfeldt-Jakob Disease (vCJD)—It is also called human mad cow disease or human bovine spongiform encephalopathy (BSE). It is a rare, degenerative, and fatal brain disease that can occur in humans. The disease damages brain cells and the spinal cord; c) Gerstmann-Straussler-Scheinker Syndrome—It results in progressive loss of coordination; d) Fatal Familial Insomnia—a rare hereditary disorder causing difficulty sleeping; and e) Kuru, caused by eating human brain tissue contaminated with infectious prions.

A protist is any eukaryotic organism that is not an animal, plant, or fungus. Pathogenic protists are single-celled organisms that cause diseases in their hosts like human, animal, or plant. These types of protists enter a host and live within the organism. Protists, when they are inside the organism, feed, grow, and reproduce, causing harm. Pathogenic protists vary in the severity of the damage they cause, but they all have a negative impact on their host. For example, *plasmodium* species are known to infect humans, and *Plasmodium falciparum* are causative agents of malaria, African sleeping sickness, amoebic encephalitis, and waterborne gastroenteritis in humans. *Trypanosomes brucei* is a flagellated endoparasite responsible for the deadly disease nagana in cattle and horses, and for African sleeping sickness in humans. Some protist pathogens prey on plants, effecting massive destruction of food crops. The oomycete Plasmopara viticola parasitizes grape plants, causing a disease called downy mildew.

Program logic is instructions in a program arranged in a prescribed order to solve a problem, usually a user request through application software. Program logic can receive the sensor data from wearable devices and store it into the database of the cloud server. It can also receive data and instructions from the microbiome mobile application and laboratory information system and process them. It can send the performance data to the laboratory information system. It can branch off and execute various methods and algorithms.

A prokaryote is a single celled microorganism that lacks a nucleus. Prokaryotes have cell membranes and cytoplasm but do not contain nuclei. All bacteria are prokaryotes. Example prokaryotes are as follows: a) *Escherichia coli*, which live in intestines, are harmless and are an important part of a healthy human intestinal tract. However, some *Escherichia coli* are pathogenic, meaning they can cause illness, either diarrhea or illness outside of the intestinal tract; and b) *Staphylococcus aureus*, which causes skin infection.

Proteins are a very important class of molecules found in all living cells. A protein is composed of one or more long chains of amino acids, the sequence of which corresponds to the DNA sequence of the gene that encodes it. Proteins act as structural components of body tissues such as muscle, hair, collagen, etc., and as enzymes and antibodies. Proteins play a variety of roles in the cell, including structural (cytoskeleton), mechanical (muscle), biochemical (enzymes), and cell signaling (hormones). Proteins are also an essential part of diet. Microorganism protein and composition information can be used for detection.

RAM (random access memory) is the hardware in a single board computer (SBC) where the operating system (OS), application programs, and sensors data in current use are kept so they can be quickly reached by the device's processor. RAM is the main memory in a computer, and it is much faster to read from and write to than other kinds of storage such as a hard disk drive (HDD), solid-state drive (SSD), or secure digital card (SDC). The wearable device SBC uses RAM to temporarily store the operating system software and sensor data.

Radio frequency identification (RFID) is a form of wireless communication that incorporates the use of electromagnetic fields in the radio frequency portion of the electromagnetic spectrum to uniquely identify an object.

A radio frequency identification tag sensor (RFID tag sensor) is an electronic tag or identification that exchanges data with an RFID reader and writer through radio waves. An RFID tag is also known as an RFID chip. The intended use of the RFID tag sensor is to detect and send RFID digital data of the wearable device. The RFID tag sensor can be passive or active. Passive RFID tag sensors have no power of their own and are powered by the radio frequency energy transmitted from RFID readers and writer antennas. The signal sent by the reader and writer is used to power on the tag and reflect the energy back to the reader. Active RFID tag sensors use battery power that continuously broadcasts its own signal. Active tags provide a much longer read range than passive tags. Wearable devices use active RFID tag sensors. RFID tag memory is split into three: unique tag identifier (TID) memory, electronic product code (EPC) memory, and user memory. Every wearable device has a unique tag identifier. The electronic product code can be a wearable device type, content type, and so on. There can be additional writeable memory locations called the access password and kill password. The access password can be used to prevent people from reconfiguring wearable device tags. The kill password is used to disable a wearable device tag permanently and irrevocably. This can be done if a wearable device is damaged or broken.

A radio frequency identification reader and writer (RFID reader) is a device used to gather information from an RFID tag, which is used to track individual objects. The device is used to write new RFID tag information. Physicians and laboratory directors are equipped with RFID readers and writers to read the wearable device RFID tag sensor electronic data. The RFID tag with unique device identifier can be used for tracking the user device. The unique device identification (UDI) is a unique numeric or alphanumeric code related to a device. It allows for a clear and unambiguous identification of specific devices with the user and facilitates their traceability. The UDI comprises a device identifier, and a production identifier. These provide access to useful information about the device. The specificity of the UDI makes traceability of the device more efficient, allows easier recall of devices, combats counterfeiting, and improves patient safety.

Resolution is the least count or smallest detectable change in the physical quantity, property, or condition being measured.

Ribonucleic acid (RNA) is a nucleic acid present in all living cells. RNA's principal role is to act as a messenger carrying instructions from DNA for controlling the synthesis of proteins. In some viruses RNA rather than DNA carries the genetic information. The RNA is single-stranded. An RNA strand has a backbone made of alternating sugar (ribose) and phosphate groups. Attached to each sugar is one of four nitrogenous bases—adenine (A), uracil (U), cytosine (C), or guanine (G). Different types of RNA exist in the cell such as messenger RNA (mRNA), ribosomal RNA (rRNA), and transfer RNA (tRNA). The picocamera, a component of the particle imaging system, allows for high-magnification and high-resolution pictures of microorganisms and small molecules. The particle imaging system allows for detection of microorganisms based on RNA segments.

A secure digital card (SDC) is a tiny flash memory card designed for high-capacity memory and various portable devices such as car navigation systems, cellular phones, e-books, PDAs, smartphones, digital cameras, music players, digital video camcorders, and single board computers. An SDC is used in a single board computer to install wearable device operating software, software compilers, utilities, and sensor software drivers. Wearable device data is stored locally in a secure digital card (SDC). The data includes a microorganism database and pollen database allowing the wearable device to be operated without being connected to the network.

A sensor can be a module or electronic component or device that receives a stimulus or input such as quantity, property, or condition, and responds with an electrical signal. It acquires a physical quantity, property, or condition and converts it into a signal suitable for processing (e.g., optical, electrical, mechanical). The intended use of the sensor is to detect and respond to some type of stimulus or input from the physical environment or motion. The stimulus or specific input can be pathogen, particulate matter, geospatial position, temperature, humidity, pressure, air quality, smoke, gas, ambient light, motion event, RFID tag sensor, or any one of a great number of other environmental phenomena. The output is generally a signal that is converted to a human-readable display at the sensor location or transmitted electronically over a network to the cloud server for reading or further processing. A sensor in general is intended to detect, measure, and monitor input. Sensors are classified in several different ways. Sensors can be classified based on external excitation signals, or a power signal, as an active or passive sensor. Active sensors are those which require an external excitation signal or power signal. Passive sensors, on the other hand, do not require any external power signal and directly generate output responses. The next classification is based on physical principles of sensing conversion phenomena, i.e., the input and the output. Some common conversion phenomena are capacitance, magnetism, induction, resistance, photoelectric, piezoelectric effect, thermoelectric effect, sound waves, thermal properties of materials, heat transfer, electrochemical, electromagnetic, and such. Sensors can also be classified based on output signal types, namely analog or digital sensors. An analog sensor is a sensor that outputs a signal that is continuous in both magnitude and space. A digital sensor is a sensor that outputs a signal that is discrete in time and/or magnitude. Wearable devices can use any of the above sensor types, which are accurate, reliable, and robust.

A single board computer is a complete computer built on a single board with central processing unit, memory, Wi-Fi/Bluetooth, accelerometer, gyroscope, microphone, speaker, secure digital card (SDC), display DSI port, camara CSI port, general purpose input/output, ports, power supply, and other features required of a functional computer. Wearable device sensors are either built in or connected to a single board computer using general purpose input/output pins.

A skin infection or a wound infection or an infected wound is a localized defect or excavation of the skin or underlying soft tissue in which pathogens have invaded into viable tissue surrounding the wound. A wound infection occurs when germs, such as bacteria, grow within the damaged skin of a wound. Symptoms can include increasing pain, swelling, and redness. More severe infections may cause nausea, chills, or fever. Many infections will be self-contained and resolve on their own, such as a scratch or infected hair follicle. Other infections, if left untreated, can become more severe and require medical intervention. Common skin infections include cellulitis, erysipelas, impetigo, folliculitis, furuncles and carbuncles. The most common pathogens found in wound infections are *Staphylococcus aureus*, Coagulase-negative staphylococci, Enterococci, and *Escherichia coli*. A bacterial wound culture is primarily ordered to detect pathogens, and to prepare a sample for susceptibility testing where required. Currently, the doctor often orders microscopy, culture, and sensitivity testing (M/C/S) as the initial test for bacterial wound culture.

A software library is a collection of non-volatile resources used by computer programs, often for application software development. These may include configuration data, documentation, help data, message templates, pre-written code, and subroutines such as math, network, internet, and so on, classes, values, or type specifications. In single board computers, the software library can include the board configuration data, peripheral interfaces, and general purpose input/output pinout configurations.

Smoke is a visible suspension of carbon or other particles in air, typically emitted from a burning substance. Smoke is a collection of tiny solid, liquid, and gas particles. Although smoke can contain hundreds of different chemicals and fumes, visible smoke is mostly carbon (soot), tar, oils, and ash. Smoke occurs when there is incomplete combustion (not enough oxygen to burn the fuel completely). Smoke can contain carbon dioxide, carbon monoxide, nitrogen oxide, and particulate matter. Particulate matter is a complex mixture of small solid or tar (liquid) particles. The size, shape, density, and other physical properties are highly variable, but the individual particles are too small to be seen with the naked eye. Smoke contributes to modifications of the nasal, oral, lung and gut microbiome, leading to various diseases, such as periodontitis, asthma, chronic obstructive pulmonary disease, heart disease, Crohn's disease, ulcerative colitis, and cancers.

A smoke sensor is an electronic component that can be used to detect the presence or concentration of smoke. The intended use of the smoke sensor is to detect, measure, and monitor smoke surrounding the user. A smoke sensor is usually used to detect the presence or concentration of smoke surrounding the user. The wearable device smoke value can be used by the user to take appropriate actions based on set acceptance criteria. The smoke sensor information can also be used to take appropriate preventive measures such as fire reporting and activating the fire alarm system during high temperature days. The smoke value is critical for the early detection of a fire and could mean the difference between life and death. In a fire, smoke and deadly gases tend to spread farther and faster than heat. Inhaling smoke for a short amount of time can cause immediate (acute) effects, especially during hot summer days. A wearable device can provide early warning and location of the fire. Smoke is irritating to the eyes, nose, and throat, and its odor may be nauseating. Exposure to heavy smoke causes temporary changes in lung function, which makes breathing more difficult. Real-time smoke sensing is important for fire detection and industrial production to detect problems in time and protect personnel safety. The unit of measurement of smoke is usually parts per million, which can be reported as smoke value such as 1 (white), 2 (slightly grey), 3 (grey), 4 (dark grey), and 5 (black) based on the opacity of the smoke. The smoke sensor sends real-time smoke data to the cloud server. The smoke sensor working principle can be based on any of the commonly used technologies like metal oxide semiconductor (MOS), also known as chemiresistors, optical scattering, filter/dilution tunnel, ringelmann scale, and interference from carbon monoxide, which is incompletely burned carbon, and so on.

A software driver is a type of software program that controls a hardware device. The wearable device software driver is used to control the sensor hardware through a single board computer. The software drivers tell the single board computer what type of sensor is connected, what it can do, and how to communicate with it from other software on the single board computer, including the operating system. Software drivers allow setup, control, and changing of settings of the microbial biosensor, particulate matter sensor, and enviro sensor.

The software graphical user interface is a user interface that includes graphical elements, such as windows, icons, buttons, menus, tabs, and pointers, which allow users to interact with electronic software and devices. A microbiome mobile application or laboratory information system software graphical user interface offers visual representations of the available commands and functions of an operating system or software program. The commands and functions can be methods and algorithms. These visual representations consist of elements like windows, icons, buttons, menus, tabs, and pointers.

Speakers are transducers that convert electromagnetic waves into sound waves. The wearable device microphone and speaker allow a person near the wearable device two-way communication with the person on the mobile device through the microbiome mobile application.

A spore is an asexual structure that can develop into an adult organism. Usually found in fungi and algae, a spore is a reproductive cell capable of developing into a new organism without fusion with another reproductive cell. Spores are produced by bacteria, fungi, algae, and plants. Spores of bacteria, fungi, algae, and protists are rarely preserved, but those of terrestrial plants are very common fossils. Terrestrial plants produce extremely resistant spores and pollen which are easily transported by wind, insects, and water. The main difference between spores and seeds as dispersal units is that spores are unicellular, the first cell of a gametophyte, while seeds contain within them a developing embryo, produced by the fusion of the male gamete of the pollen tube with the female gamete. Spores are usually 10 to 20 μm in diameter, although larger sizes also occur in some species.

A system on Chip (SoC) is an integrated circuit that integrates most of the components of the single board computer (SBC). The components include a central processing unit (CPU), graphical processing unit (GPU), memory input/output ports, and secondary storage, all on a single substrate or microchip.

A temperature sensor is an electronic component that measures the temperature of its environment and converts the input data into electronic data to record, monitor, or signal temperature change. The intended use of the temperature sensor is to detect, measure, and monitor temperature surrounding the user. The wearable device temperature value can be used by the user to take appropriate actions based on set acceptance criteria. The temperature value can also be used to take appropriate preventive measures such as cooling the environment around the user or moving to a shade. Temperature units of measurement are usually Celsius and Fahrenheit. The temperature of the wearable device can be reported in the form Celsius or Fahrenheit. The temperature sensor sends real-time temperature data to the cloud server. The temperature sensor working principle can be based on any of the four commonly used temperature sensor types such as: 1) Thermocouple, which is made from two dissimilar metals that generate electrical voltage in direct proportion to changes in temperature, 2) Resistance temperature detector (RTD), which measures temperature by correlating the resistance of the RTD element with temperature, 3) Negative temperature coefficient (NTC) thermistor, consisting of a thermally sensitive resistor that exhibits a large, predictable, and precise change in resistance correlated to variations in temperature, and 4) Semiconductor-based MEMS sensors placed on integrated circuits (ICs). These sensors are effectively two identical diodes with temperature-sensitive voltage vs current characteristics that can be used to monitor changes in temperature. Microorganisms can also be classified according to the range of temperature at which they can grow. The growth rates are the highest at the optimum growth temperature for the organism. The lowest temperature at which the organism can survive and replicate is its minimum growth temperature. The highest temperature at which growth can occur is its maximum growth temperature. High temperature can result in deactivation of the microorganisms.

A wearable device consists of a smart band, and a display unit. The smart band consists of a microbial biosensor, a particulate matter sensor, an enviro sensor, a single board computer, a power supply unit, a band fastener, and a set of watch adapters. The intended use of the wearable device is for detection of microorganisms, sterilization of pathogens, and environmental monitoring. A wearable device sensor can be worn on the wrist and ankle. Wearable devices can be attached on a necklace, a waistband, a belt, or a headband. Users can wear one or more wearable devices. In this case, when more than one wearable device is used, each one of them can be uniquely identified using an RFID tag sensor.

An ultraviolet light sensor intended use is to measure ultraviolet radiation. Ultraviolet radiation (UV) is present in sunlight, and constitutes about 10% of the total electromagnetic radiation output from the sun. The UV index is a measure to help determine the effects of the sun on outdoor activities. It is computed using forecast ozone levels, cloudiness, and elevation. Values are usually highest at solar noon, which is when the sun is at its highest point of the day. The UV index ranges from 1-11+ based on how the sun's UV rays affect the person. The ranges are: 1-2 (low), 3-5 (moderate), 6-7 (High), 8-10 (very high), 11+(extreme). The UV region covers the wavelength range 100-400 nm and is divided into three bands: UV-A (315-400 nm), UV-B (280-315 nm), UV-C (100-280 nm). The ultraviolet light sensor outputs an analog voltage that is directly proportional to UV radiation incident on a planar surface. Higher ultraviolet light inhibits growth of most of the microorganisms. High ultraviolet light inactivates microorganisms by forming pyrimidine dimers in RNA and DNA, which can interfere with transcription and replication.

A unique identifier (UI) is a unique identification of a microorganism based on a biosensor transducer used to detect microorganisms. This biosensor transducer signal to detect microorganisms comprises: a) Optical—infrared spectroscopy, fluorescence imaging, particle imaging—nucleic acid sequence read, light scattering, and imaging; b) Mass based electromagnetic wave; c) Ultrasound—acoustic wave. The picocamera image detection is based on microorganism image acquisition and classification. The UI can be used to identify and characterize microorganisms for diverse goals such as beneficial microorganism and pathogen detection in the nasal cavity, in the oral cavity, or on a surface, real time monitoring of environment, medical diagnostics, biodefense, and microbial forensics. The desired microorganism and pathogen detection resolution varies based on type but could easily range from family to genus to species to strain to isolate. The UI can be an already identified value based on the biosensor transducer method or can be an artificial intelligence method based calculated predictive value using microorganism database information.

A universal serial bus (USB) is a common interface that enables communication between devices and a single board computer. A USB is a type of computer port that can be used to connect to items such as a keyboard, mouse, and camera. In the case of wearable devices, it can be used to connect to other sensors like weight, wind, and rain. There are several types of USB such as A, B, C, Mini-USB, and Micro-USB. The single board computer is compatible with various types of USB.

A user is a person who is using a wearable device to detect microorganisms, sterilize pathogens, and monitor environment.

A virion is a complete, infective form of a virus outside a host cell, with a core of RNA or DNA and a capsid. It is an entire fully assembled virus particle, consisting of an outer protein shell called a capsid and an inner core of nucleic acid (either RNA or DNA) outside the cell.

A viroid is an infectious entity affecting plants, smaller than a virus and consisting only of nucleic acid without a protein coat. Viroids are plant pathogens that consist of a very short stretch of circular, single-stranded RNA that does not have a protein coat. Viroids are strands of naked RNA.

A virus is an infective agent that typically consists of a nucleic acid molecule in a protein coat, is very small to be seen by light microscopy, and can multiply only within the living cells of a host. Viruses are particles of nucleic acid, protein, and in some cases lipids that can reproduce only by infecting living cells. Viruses are made up of a piece of genetic code, such as DNA or RNA, and protected by a coating of protein. All viruses enter living cells, and once inside, use the machinery of the infected cell to produce more viruses. Viruses differ widely in terms of size, structure, and chemical composition. Most viruses have a diameter from 20 nm to 250-400 nm. The largest measure about 500 nm in diameter and are about 700-1,000 nm in length.

Virus shapes are usually complex (comprising head, DNA, tail, tail fiber), helical, polyhedral, spherical or enveloped. Viruses can affect humans, plants, and bacteria. A tobacco mosaic virus causes the leaves of tobacco plants to develop a pattern of spots called a mosaic. Most viruses have a pathogenic relationship with their hosts, but they are not all bad. Some viruses can kill bacteria, while others can fight against more dangerous viruses. Like protective bacteria (probiotics), there are protective viruses in our body. Viruses that help humans comprise: a) Bacteriophages that infect and destroy specific bacteria. Bacteriophages are found in the mucous membrane lining in the digestive, respiratory, and reproductive tracts. Bacteriophages have been used to treat dysentery, sepsis caused by *Staphylococcus aureus, salmonella* infections, and skin infections; b) An oncolytic virus preferentially infects and kills cancer cells. As the infected cancer cells are destroyed by oncolysis, they release new infectious virus particles or virions to help destroy the remaining tumor; c) Viruses can be used to inject genes into cells, which can reverse genetic diseases. For example, some viruses have been able to cure hemophilia, a blood disorder that prevents clotting; and d) Viral infections at a young age are important to ensure the proper development of our immune systems. The immune system can be continuously stimulated by systemic viruses at low levels sufficient to develop resistance to other infections. Viral infection can be as follows: a) COVID-19 disease. The SARS-CoV-2 virus belongs to the same large family of viruses as SARS-CoV, known as coronaviruses, and results in severe acute respiratory syndrome. This normally happens because of poor handwashing or from consuming contaminated food or water. The airborne transmission occurs through sneezing. Common symptoms include fever, dry cough, and shortness of breath, and the disease can progress to pneumonia in severe cases; b) Flu is caused by influenza viruses that infect the nose, throat, and lungs. These viruses spread when people with flu cough, sneeze, or talk, sending droplets with the virus into the air and potentially into the mouths or noses of people who are nearby; c) Dengue is a mosquito-borne viral infection causing a severe flu-like illness; d) Ebola virus causes fatigue, fever, and muscle pain; e) Rabies virus transmitted through an infected animal's saliva causes brain damage; f) HIV (human immunodeficiency virus) is a virus that attacks cells that help the body fight infection, making a person more vulnerable to other infections and disease; g) Rotavirus infection usually spreads from fecal-oral contact due to poor sanitation and causes diarrhea; and h) Marburg virus causes hemorrhagic fever, meaning that infected people develop high fevers and bleeding throughout the body that can lead to shock, organ failure, and death.

Wi-Fi is a family of wireless networking technologies, allowing computers, smartphones, or other devices to connect to the internet or communicate with one another wirelessly within a particular area. The microbiome mobile application allows users to access the wearable device data through Wi-Fi. Wi-Fi can also be used to connect to other sensor devices like external rooftop rain and wind weather stations to monitor other environmental conditions near the user.

Exemplary Systems and Methods

FIG. 1-48 illustrate an example wearable device 100, according to some embodiments.

FIG. 1 is an example perspective view of an example wearable device 100 design that can be utilized to implement various embodiments.

A wearable device 100 consists of a smart band 200 and a display unit 102.

The smart band 200 comprises a microbial biosensor 310, a particulate matter sensor 320, an enviro sensor 330, a single board computer 350, a power supply unit 380, a band fastener 202, and a set of watch adapters 204 and 206. Smart band 200 also has set of clip adapters 208 and 210 to connect to a necklace 4810, a waistband 4820, a belt 4830, a headband 4840, and so on for discreet monitoring.

The band fastener 202 is a mechanism that closes or secures the smart band 200. The band fastener 202 can be a magnetic lock, clip, or any other locking mechanism which secures the two sides of the smart band 200.

The display unit 102 comprises a touchscreen 104, a display unit power button 106, a crown 108, and a set of attachment slots 110 and 112.

The microbial biosensor 310 comprises a transmitter 312, a receiver 314, a sterilizer 316, a picocamera 318, and a microbial biosensor power button 319.

The particulate matter sensor 320 comprises a sensing cavity 322.

The enviro sensor 330 comprises a set of sensors 332-346.

The power supply unit 380 comprises a wireless charging unit 382, a battery 384, a charging port 386, and a band power button 388.

A microbiome mobile application 250 allows a user to access the wearable device 100 sensor data.

Figure 2:
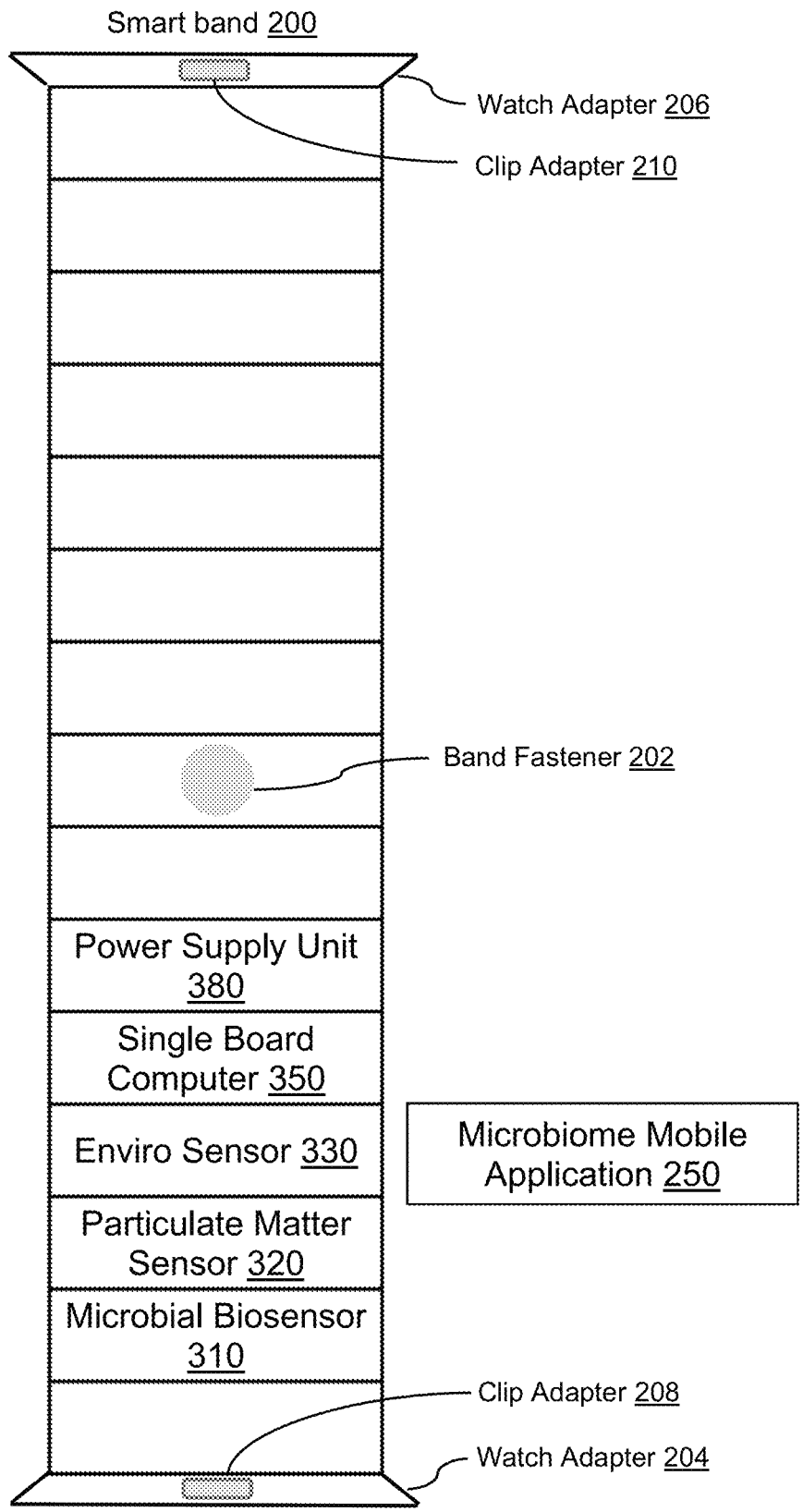
FIG. 2 is an example smart band design that can be utilized to implement various embodiments.

FIG. 2 is an example smart band 200 design that can be utilized to implement various embodiments.

The smart band 200 comprises a microbial biosensor 310, a particulate matter sensor 320, an enviro sensor 330, a single board computer 350, a power supply unit 380, a band fastener 202, a set of watch adapters 204 and 206, and a set of clip adapters 208 and 210. The watch adapters 204 and 206 allow the smart band 200 to be connected to any watch. The set of clip adapters 208 and 210 allow it to be attached to a necklace 4810, a waistband 4820, a belt 4830, a headband 4840, and so on for discreet monitoring.

Figure 3:
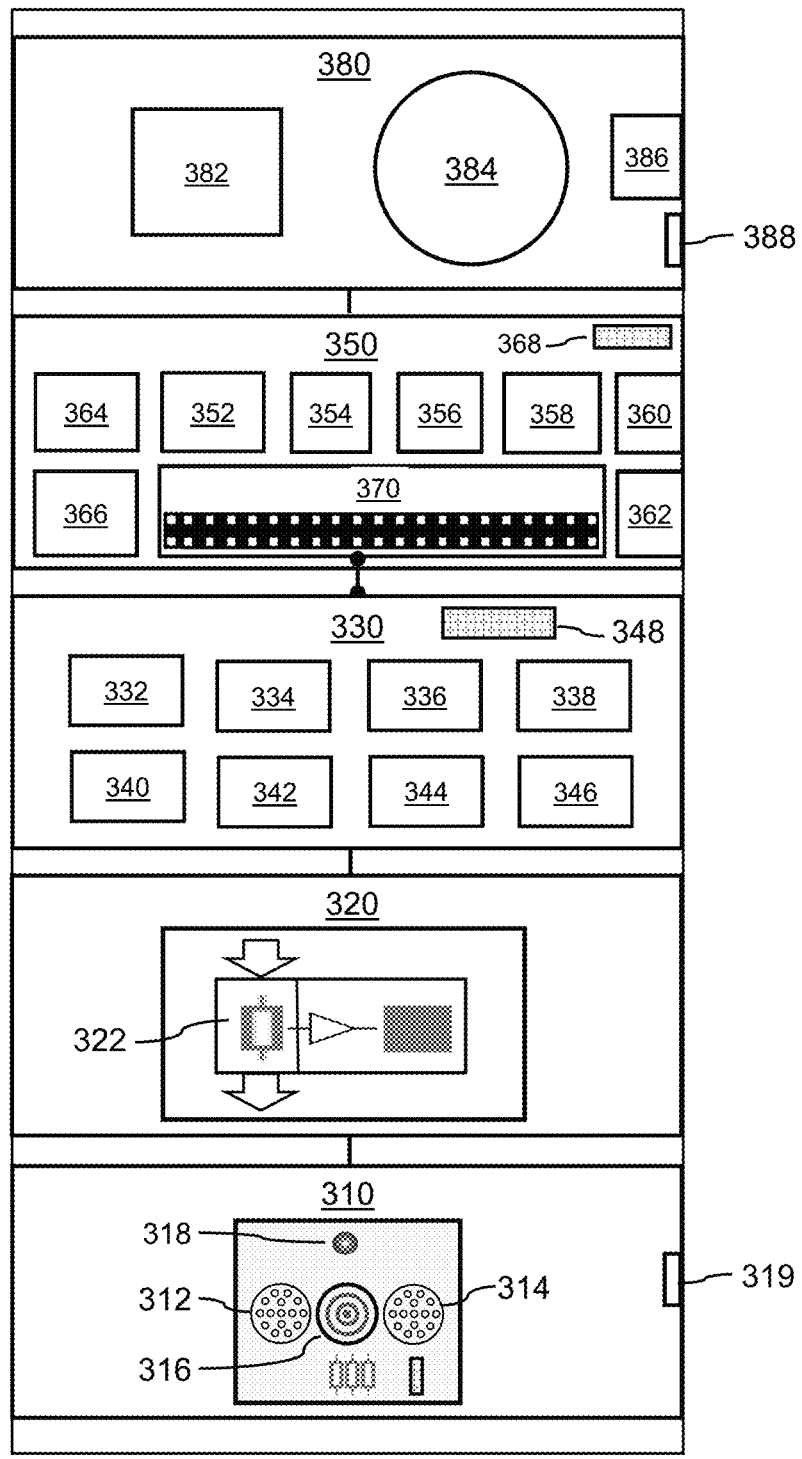
FIG. 3 is an example smart band circuit block diagram, according to some embodiments.

FIG. 3 is an example smart band circuit block diagram 300, according to some embodiments.

The wearable device circuit block diagram 300 of the smart band 200 consists of following items:

The microbial biosensor 310, particulate matter sensor 320, enviro sensor 330, single board computer 350, and power supply unit 380.

The microbial biosensor 310 comprises a transmitter 312, a receiver 314, a sterilizer 316, a picocamera 318, and a microbial biosensor power button 319.

The particulate matter sensor 320 comprises a sensing cavity 322.

The enviro sensor 330 comprises a set of sensors 332-346. The set of sensors are an RFID tag sensor 332, location sensor 334, ambient light sensor 336, gas sensor 338, smoke sensor 340, temperature, humidity, and pressure sensor 342, sound sensor 344, and ultraviolet light sensor 346. The enviro pinout cable 348 is connected to the single board computer 350 general purpose input/output (GPIO) pinout 370.

The single board computer 350 comprises a system on chip (SOC) 352, RAM 354, accelerometer 356, gyroscope 358, secure digital card (SDC) 360, display DSI port 362, Wi-Fi Bluetooth 364, microphone and speaker 366, camera CSI port 368, and general purpose input/output (GPIO) pinout 370.

The power supply unit 380 comprises a wireless charging unit 382, a battery 384, a charging port 386, and a band power button 388.

The microbial biosensor 310, particulate matter sensor 320, enviro sensor 330, and power supply unit 380 are connected to single board computer 350 through GPIO pinout 370.

A microbiome mobile application 250 allows a user to access the wearable device 100 and sensor data.

The wearable device 100 enviro sensor 330 detects, monitors, and measures environmental conditions surrounding the user, comprising:

an RFID tag sensor 332 to detect, measure, and monitor RFID tag digital data.

a location sensor 334 to detect, measure, and monitor a geospatial position and an altitude.

an ambient light sensor 336 to detect, measure, and monitor an ambient light level.

a gas sensor 338 to detect, measure, and monitor a gas type.

a smoke sensor 340 to detect, measure, and monitor a smoke level.

a temperature, humidity, and pressure sensor 342 to detect, measure, and monitor a temperature.

a temperature, humidity, and pressure sensor 342 to detect, measure, and monitor a humidity.

a temperature, humidity, and pressure sensor 342 to detect, measure, and monitor a pressure.

a sound sensor 344 to detect, measure, and monitor a sound level.

an ultraviolet light sensor 346 to detect, measure, and monitor an ultraviolet index.

The enviro sensor data is used to predict a pathogen biosafety level risk, a pollen allergy level risk, a dust mite allergy level risk, an air quality index risk, a fire risk, a hearing loss risk, and an unprotected sun exposure risk. The risk factors allow the user to take appropriate corrective and protective actions to prevent exposure to unhealthy environmental conditions.

The sensors 332-346 are made up of space saving rugged micro-electromechanical system (MEMS) and picomaterial components.

FIG. 4 is an example schematic representation of a single board computer general purpose input output pin numbering diagram 410, and a general purpose input output pinout function 450 that can be utilized to implement various embodiments.

The general purpose input output pin numbering diagram 410 shows the layout of pins 1-42 of GPIO pinout 370. The light gray pinout is either a 3V3-volt (3.3-volt) or 5-volt power supply. The black pinout is represented as Ground or GND.

The remaining GPIO pins are uncommitted digital signal pins on an integrated circuit or electronic circuit board of the single board computer 350 whose behavior—including whether they act as input or output—is controllable by the user at run time. Sensor software drivers are used to map the GPIO pinout 370 to the sensor pinout of microbial biosensor 310, particulate matter sensor 320, enviro sensor 330, and power supply unit 380.

The general purpose input output pinout function 450 shows pins 1-42 of GPIO pinout 370 functions.

FIG. 5 is an example single board computer 350 general purpose input output pinout function description table 500 that can be utilized to implement various embodiments.

The voltage 502 describes the ground and power functions.

The inputs 504 describe how the GPIO pin is assigned an input pin through single board computer 350 software settings.

The outputs 506 describe how the GPIO pin is assigned an output pin through single board computer 350 software settings.

The pulse-width modulation (PWM) 508 is a technique for getting analog results with digital means. Digital control is used to create a square wave, a signal switched between on and off. This on-off pattern can simulate voltages in between full on (5 volts) and off (0 volts) by changing the portion of the time the signal spends on versus the time that the signal spends off. The duration of "on time" is called the pulse width. To get varying analog values, one can change, or modulate, that pulse width. If this on-off pattern is repeated fast enough with an LED, for example, the result is as if the signal is a steady voltage between 0 and 5 V, controlling the brightness of the LED of the flash.

The serial peripheral interface (SPI) 510 is a synchronous serial communication interface specification used for a short distance communication. The serial peripheral interface (SPI) is an interface bus commonly used to send data between the single board computer 350 and small peripherals such as shift registers, microbial biosensor 310, particulate matter sensor 320, enviro sensor 330, and a secure digital card 360. It uses separate clock and data lines, along with a select line to connect to the sensor component. SPI allows attachment of multiple compatible microbial biosensor 310, particulate matter sensor 320, and enviro sensor 330 to a single set of pins by assigning them different chip-select pins. SPI is another type of communication protocol for communicating between sensors. It also uses a master/slave setup but is primarily used in short distances between a main (master) controller and peripheral devices (slaves) such as sensors. SPI typically uses three wires to communicate with the single board computer 800: SCLK, MOSI, and MISO. SPI needs to be enabled within the single board computer 350 configuration menu before it can be used. There are two types of SPI modes as below:

Standard mode—In standard SPI master mode, the peripheral implements the standard 3-wire serial protocol (SCLK, MOSI, and MISO).

Bidirectional mode—In bidirectional SPI master mode, the same SPI standard is implemented, except that a single wire is used for data (MOMI) instead of the two used in standard mode (MISO and MOSI). In this mode, the MOSI pin serves as MOMI pin.

Either of the two SPI modes can be used by the microbial biosensor 310, particulate matter sensor 320, and enviro sensor 330 based on the sensor pinout connection requirements.

The inter-integrated circuit (I2C) 512 protocol is a synchronous protocol intended to allow multiple "slave" digital integrated circuits ("chips") to communicate with one or more "master" chips. It is widely used for attaching lower-speed peripheral ICs to processors and the single board computer 350 in short-distance, intra-board communication. It only requires two signal wires to exchange information. This is a common type of communication between the single board computer 350 and microbial biosensor 310, particulate matter sensor 320, and enviro sensor 330. It works by having a master and a slave. The master in this case is the single board computer 350, and the slave devices are hardware peripherals like microbial biosensor 310, particulate matter sensor 320, and enviro sensor 330 that would normally extend the functionality of the device. The advantage of I2C is that one can connect hundreds of sensors up to the same master using the same two-wire interface, providing that each device has a different I2C address. This is very useful in the case of a wearable device 100 containing many sensors.

In serial interface 514, a serial pin TX is used to transmit, and a serial pin RX is used to receive the data. In telecommunication and data transmission, serial communication is the process of sending data one bit at a time, sequentially, over a communication channel or computer bus. This contrasts with parallel communication, when several bits are sent as a whole, on a link with several parallel channels. Sensors like GPS are connected to GPIO TX and RX pins.

FIG. 6 illustrates an example set of microorganisms 610, pollen grain 630, dust mite allergen 640, and relative size of particles 650 that can be utilized to implement various embodiments.

The set of microorganisms 610 can be a prion or prions 612, virus or viruses 614, bacterium or bacteria 616, a fungi or fungus 618, a protist or protists 620, and a dust mite or dust mites 622.

The prions 612 are found in diseased meat, skin, brain, and so on. The prions are also found in leaves, at levels that should be able to infect an animal.

The most common microorganisms 610 found in the nasal cavity 2840 and oral cavity 2890 comprise:

Virus 614 comprising SARS-CoV-2, Dengue, Ebola, Hepatitis A, Norovirus, Rotavirus, Adenoviruses, Astroviruses, and so on;

Bacteria 616 comprising *Salmonella, Escherichia coli, Streptococcus, Shigella, Pseudomonas aeruginosa, mycobacterium, Giardia Lamblia, Yersinia, Klebsiella*, and so on; and Fungi 618 comprising Ringworm, Dermatophytes, Yeast *candida*, and so on.

Most protists 620 are aquatic organisms. Protists 620 need a moist environment to survive. As such they are found mainly in contaminated water, damp soil, marshes, puddles, lakes, and the ocean. Protists are found on the surfaces of an object.

The dust mites 622 are found in bedding, mattresses, upholstered furniture, carpets, or curtains in your home. They feed on dead human skin cells and hair cells. There are two main types of house dust mites in North America. The American Dust Mite is known as *Dermatophagoides farinae*, and the European Dust Mite is known as *Dermatophagoides pteronyssinus*. Dust mites 622 do not bite humans or animals. House dust mite 622 excrements are considered the main source of allergy. The dust mite 622 excrement or droppings are the major source of allergens and a major contributor to allergic diseases such as asthma, rhinitis, and atopic dermatitis.

Pollen grains 630 are microscopic structures that carry the male reproductive cell of plants. Pollen grains 630 have many different kinds of shapes and usually identified by shape and number of apertures.

The dust mite allergens 640 are dust mite excrements 1818 found in the environment air.

The relative size of particles 650 provides insight into various sizes of particles like atoms, small molecules, lipids, proteins, prions, viruses, bacteria, organelles, fungi, protists, eukaryotic cells (depicted bigger than actual size), pollen, and dust mites. The relative size of particles 650 provides visual correspondence to the size of the microorganisms 610.

The smallest particle is the atom, which is 100 picometers (μm), and dust mites are 0.2-0.3 mm (millimeters) long. The eye can see particles of sizes up to 0.1 mm. Light microscopes allow seeing of particle sizes as small as about 500 nanometers (nm). The electron microscope allows seeing of particle sizes less than 1 nm and about 100 micrometers (μm). Light microscope and electron microscope disadvantages are cost, size, maintenance, training, and image artifacts resulting from specimen preparation. They are large, cumbersome, expensive pieces of equipment, extremely sensitive to vibration and external magnetic fields. The electromagnetic spectrum 2300 used by electron microscopes fails in the region ionizing radiation and is hazardous to humans. The picocamera 318 and particle imaging 2530 detection method allow seeing of particle sizes less than 1 nm and about 1 mm.

FIG. 7 is an example prion structure and components diagram 710, a prion structure components, function, and chemical composition list 730, a prion disease, status, and source list 750, and a prion attributes and biosensor detector list 790, according to some embodiments.

The prion structure and components diagram 710 shows how normal prion protein 712 amino acids in alpha helix 716 form transforms to misfolded prion protein 712 amino acids in beta helix 718 form and causes disease.

The prion structure components, function, and chemical composition list 730 lists the amino acids in alpha helix 716 form and amino acids in beta helix 718 form primary function and shape and chemical composition.

The prion disease, status, and source list 750 describes the prion disease, its contagious or noncontagious status, and source.

The prion attributes and biosensor detector list 790 describes the prion attributes.

The above structure, components, chemical composition information for each prion 612 is used by the microbial biosensor 310 and particulate matter sensor 320 to detect it. The particle detection methods 2500 of particle imaging 2530, and light scattering and imaging 2570, are more suitable to detect prions 612.

FIG. 8 is an example virus structure and components diagram 810, a virus structure components, function, and chemical composition list 830, and a percent chemical composition of a virus list 850, according to some embodiments.

The virus structure and components diagram 810 shows the various components and their shapes of an exemplary SARS-CoV-2 virus.

The virus structure components, function, and chemical composition list 830 describes the component name, its primary function, and predominant chemical composition.

The percent chemical composition of a virus list 850 describes primary constituents and corresponding percent of dry weight.

The above structure, components, and chemical composition information for each virus 614 is used by the microbial biosensor 310 and particulate matter sensor 320 to detect it. The particle detection methods 2500 of particle imaging 2530, nucleic acid sequence identification 2540, and light scattering and imaging 2570 are more suitable to detect virus 614.

Figure 9:
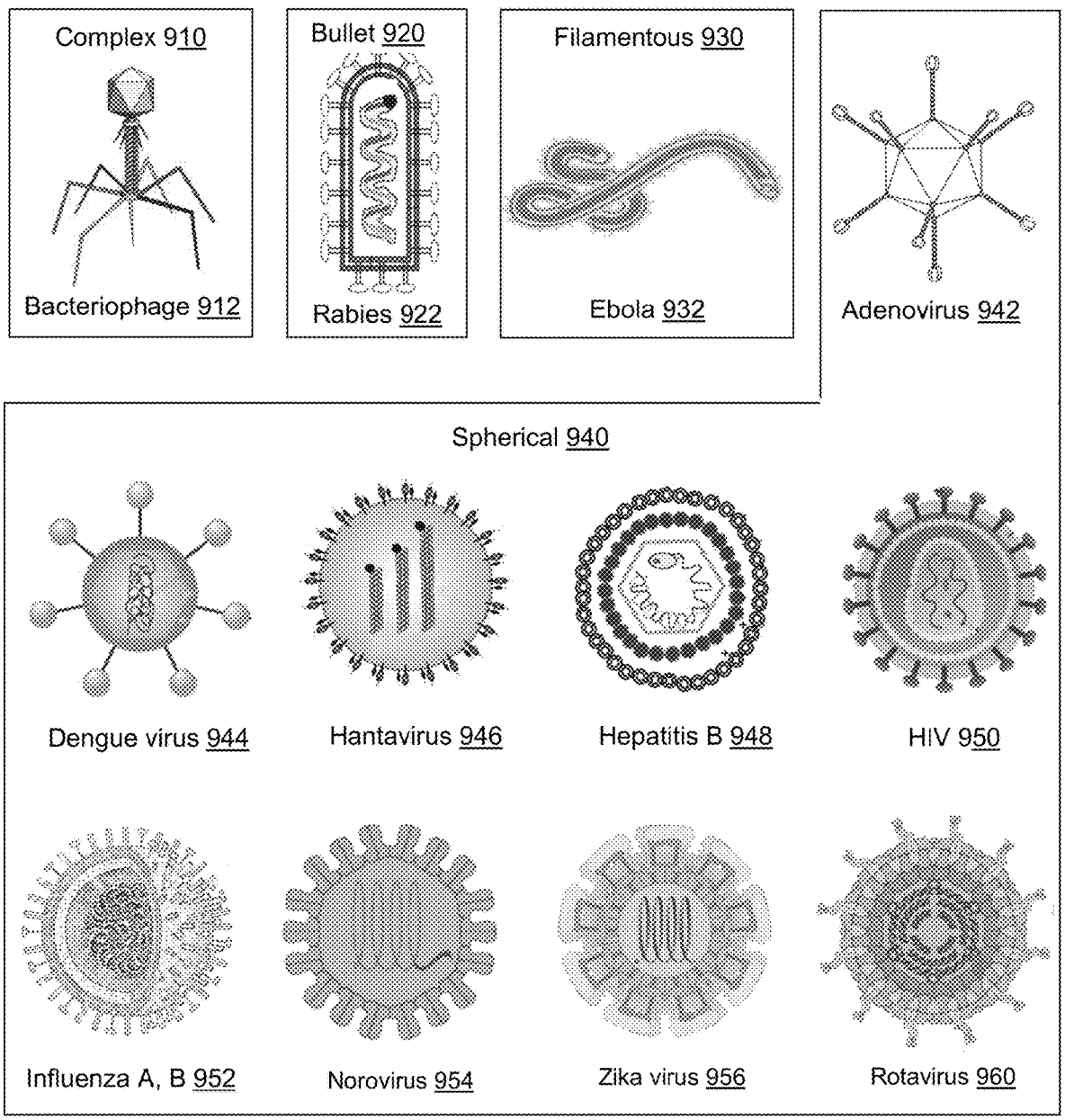
FIG. 9 is an example virus shapes diagram, according to some embodiments.

FIG. 9 is an example virus shapes diagram 900, according to some embodiments.

The virus 614 shapes can be a Complex 910, a Bullet 920, a Filamentous 930, and a Spherical 940.

The example viruses 614 for each shape are listed below:
Complex 910 e.g., Bacteriophage 912
Bullet 920 e.g., Rabies 922
Filamentous 930 e.g., Ebola 932 and Marburg
Spherical 940 e.g., Adenovirus 942, Dengue virus 944, Hantavirus 946, Hepatitis B 948, HIV 950, Influenza A, B 952, Norovirus 954, Zika virus 956, Rotavirus 960.

The above virus shape attribute information for each virus 614 is used by the microbial biosensor 310 and particulate matter sensor 320 to detect it.

FIG. 10 is an example virus name, disease, status, source, shape, size, and nucleic acid list 1000, and a virus attributes and biosensor detector list 1090, according to some embodiments.

The virus name, disease, status, source, shape, size, and nucleic acid list 1000 and a virus attributes and biosensor detector list 1090 are used by the microbial biosensor 310 and particulate matter sensor 320 to detect it. The virus 614 pathogen safety data sheet of FIG. 44, FIG. 45, and FIG. 46 information is derived from this data.

FIG. 11 is an example bacteria cell structure and components diagram 1110, a bacteria cell structure components, function, and chemical composition list 1130, and a percent chemical composition of a bacteria list 1150, according to some embodiments.

The bacteria cell structure and components diagram 1110 shows the various components and their shapes of an exemplary *Escherichia coli* bacteria.

The bacteria cell structure components, function, and chemical composition list 1130 describes the component name, its primary function, and predominant chemical composition.

The percent chemical composition of a bacteria list 1150 describes primary constituents and corresponding percent of dry weight.

The above structure, components, and chemical composition information for each bacterium 616 is used by the microbial biosensor 310 and particulate matter sensor 320 to detect it. The particle detection methods 2500 of infrared spectroscopy 2510, fluorescence imaging 2520, particle imaging 2530, nucleic acid sequence identification 2540, ultrasound waves 2560, and light scattering and imaging 2570 are more suitable to detect bacteria 616.

FIG. 12 is an example bacterial cell shapes diagram 1200, according to some embodiments.

The bacteria 616 shapes can be Spherical 1210, Spiral 1220, Rod 1230, Comma 1250, Box 1260, Appendaged 1270, and Pleomorphic 1280.

The example bacteria 616 for each shape are listed below:
Spherical (Cocci) 1210 e.g., *Streptococcus pneumoniae* 1212, *Staphylococcus aureus* 1214
Spiral 1220 e.g., *Treponema pallidum* 1222
Rod (*Bacillus*) 1230 e.g., *Legionella pneumophila* 1232, *Clostridium botulinum* 1234, *Streptobacillus moniliformis* 1236, *Salmonella typhi* 1238, *Helicobacter pylori* 1240
Comma 1250 e.g., *Vibrio cholerae* 1252
Box 1260 e.g., Halophilic 1262
Appendaged 1270 e.g., *Hyphomicrobium* 1272
Pleomorphic 1280 e.g., *Corynebacterium diphtheria* 1282

The above bacteria cell shapes 1200 information for each bacterium 616 is used by the microbial biosensor 310 and particulate matter sensor 320 to detect it.

FIG. 13 is an example bacteria name, disease, status, source, shape, size, and nucleic acid list 1300, and a bacteria attributes and biosensor detector list 1390, according to some embodiments.

The bacteria name, disease, status, source, shape, size, and nucleic acid list 1300 and bacteria attributes and biosensor detector list 1390 are used by the microbial biosensor 310 and particulate matter sensor 320 to detect it. The bacteria 616 pathogen safety data sheet information is derived from this data.

FIG. 14 is an example fungi cell structure and components diagram 1410, a fungi cell structure components, function, and chemical composition list 1440, and a percent chemical composition of a fungi list 1450, according to some embodiments.

The fungi cell structure and components diagram 1410 shows the various components and their shapes of an exemplary yeast fungi.

The fungi cell structure components, function, and chemical composition list 1440 describes the component name, its primary function, and predominant chemical composition.

The percent chemical composition of a fungi list 1450 describes primary constituents and corresponding percent of dry weight.

The above structure, components, chemical composition information for each fungus 618 is used by the microbial biosensor 310 and particulate matter sensor 320 to detect it. The particle detection methods 2500 of infrared spectroscopy 2510, fluorescence imaging 2520, particle imaging 2530, nucleic acid sequence identification 2540, ultrasound waves 2560, and light scattering and imaging 2570 are more suitable to detect fungi 618.

FIG. 15 illustrates a fungi cell shapes diagram 1510, and a fungi cell shape in environment and shape shift in host diagram 1520, according to some embodiments.

The fungi 618 shapes can be a Yeast cell 1512, Septate hyphae 1514, and Coenocytic hyphae 1516.

The yeast cell 1512 is described in fungi cell structure and components diagram 1410.

Septate hyphae 1514 have dividers between the cells, called septa (singular septum). The septa have openings called pores between the cells, to allow the flow of nutrients, cytoplasm, ribosomes, mitochondria, and sometimes nuclei to flow among cells and throughout the mycelium.

Coenocytic hyphae 1516 are nonseptate, meaning they are one long cell that is not divided into compartments. Coenocytic hyphae are big, multinucleated cells. The branches are hyphae, or filaments, of a mold called *Penicillium*. A mycelium may range in size from microscopic to very large. One of the largest living organisms on Earth is the mycelium of a single fungus 618.

The fungi cell shape in environment and shape shift in host diagram 1520 describes the shape of fungi 618 in the environment 1522 to shape shift in host 1524 as follows:

*Aspergillus fumigatus* 1530 shape shift in host 1524 is to Conidia to hyphae 1532

*Coccidioides immitis* 1540 shape shift in host 1524 is to Arthrosporic to sphere 1542

*Blastomyces dermatitidis* 1550 shape shift in host 1524 is to Spores to yeast cell 1552 in lungs and blood stream

*Candida albicans* 1560 shape shift in host 1524 is to Hyphae to Pseudo hyphae 1562

*Histoplasma capsulatum* 1570 shape shift in host 1524 is to Conidia to budding 1572

The above fungi cell shape in environment and shape shift in host diagram 1520 for each fungus 618 is used by the microbial biosensor 310 and particulate matter sensor 320 to detect it. The microbial biosensor 310 uses the data associated with shape shift in host 1524, whereas the particulate matter sensor 320 uses data associated with the shape in the environment 1522 to detect fungi 618.

FIG. 16 is an example fungi name, disease, status, source, shape, size, and nucleic acid list 1600, and a fungi attributes and biosensor detector list 1690, according to some embodiments.

The fungi name, disease, status, source, shape, size, and nucleic acid list 1600, and a fungi attributes and biosensor detector list 1690 are used by the microbial biosensor 310 and particulate matter sensor 320 to detect it. The fungi 618 pathogen safety data sheet information is derived from this data.

FIG. 17 is an example protist cell structure and components diagram 1710, a protist cell components, function, chemical composition list 1750, and a protist attributes, protists disease, source, shape, size, and nucleic acid list 1780, and protist attributes and biosensor detector list 1790, according to some embodiments.

The protist cell structure and components diagram 1710 shows an example Paramecia protist. Paramecia are single-celled protists that are naturally found in aquatic habitats. They are typically oblong or slipper-shaped and are covered with short hairy structures called cilia as shown in the diagram. The protist 620 can be found in the mouth after drinking contaminated water.

The protist cell structure and components diagram 1710, protist cell components, function, chemical composition list 1750, and protist attributes, protists disease, source, shape, size, and nucleic acid list 1780, and protist attributes and biosensor detector list 1790 information for each protist 620 is used by the microbial biosensor 310 and particulate matter sensor 320 to detect it. The particle detection methods 2500 of infrared spectroscopy 2510, fluorescence imaging 2520, particle imaging 2530, nucleic acid sequence identification 2540, ultrasound waves 2560, and light scattering and imaging 2570 are more suitable to detect protists 620.

FIG. 18 is an example dust mite structure and components diagram 1810, a dust mite structure components, function and chemical composition list 1850, and a dust mite attributes and biosensor detector list 1890, according to some embodiments.

The dust mite structure and components diagram 1810, dust mite structure components, function and chemical composition list 1850, and dust mite attributes and biosensor detector list 1890 information for each dust mite 622 is used by the microbial biosensor 310 and particulate matter sensor 320 to detect it. The particulate matter sensor 320 also detects the dust mite allergens 640 which are excrements 1818 found in the environment air. Dust mite allergen 640 are Peptidase 1 enzymes found in the fecal pellets of mites. Enzymes structures are made up of a amino acids which are linked together via amide (peptide) bonds in a linear chain. This is the primary structure. The resulting amino acid chain is called a polypeptide or protein and is used to detect the dust mite allergen 640.

The particle detection methods 2500 of infrared spectroscopy 2510, fluorescence imaging 2520, particle imaging 2530, nucleic acid sequence identification 2540, electromagnetic waves 2550, ultrasound waves 2560, and light scattering and imaging 2570 are more suitable to detect dust mites 622.

FIG. 19 is an example virus, bacteria, and fungi attributes comparison list 1900, according to some embodiments.

The comparison attributes allow the initial sorting of data based on size, shape, color, cell membrane, genetic material, and so on. This reduces the amount of time it takes to detect the virus 614, bacteria 616, and fungi 618 in the nasal cavity 2840, or in the oral cavity 2890, or on the surface 3050.

FIG. 20 is an example platform dataset 2010, and a microorganism taxonomy 2050, according to some embodiments.

The platform dataset 2010 comprises information from important open-source resources such as NCBI, EMBL-EB, CDC MicrobeNet, and prion, virus, bacteria, fungi, protist, dust mite, and pollen databases. The data is further augmented with annotated information associated with attributes and unique identifiers based on biosensor detector and particle detection methods 2500.

The microorganism taxonomy 2050 allows for classifying new organisms or reclassifying existing ones. Microorganisms are scientifically recognized using a binomial nomenclature using two words that refer to the genus and the species. The names assigned to microorganisms are in Latin.

This includes variants associated with same microorganism based on structure component and/or DNA/RNA sequence. Taxonomy is the science of naming, describing, and classifying organisms and includes all plants, animals, and microorganisms of the world. Biological classification uses taxonomic ranks such as Domain, Kingdom, Phylum, Class, Order, Family, Genus, Species, and Strain. Currently there is no prion taxonomy. Prions have not been classified in the same way as viruses, thus there are no families, genera, or species. They first are identified by their host species, and associated clinical disease, and then characterized further by their molecular and biological properties. The microorganism taxonomy 2050 lists consist of examples associated with virus taxonomy, bacteria taxonomy, fungi taxonomy, protist taxonomy, and dust mite taxonomy.

Figure 21:
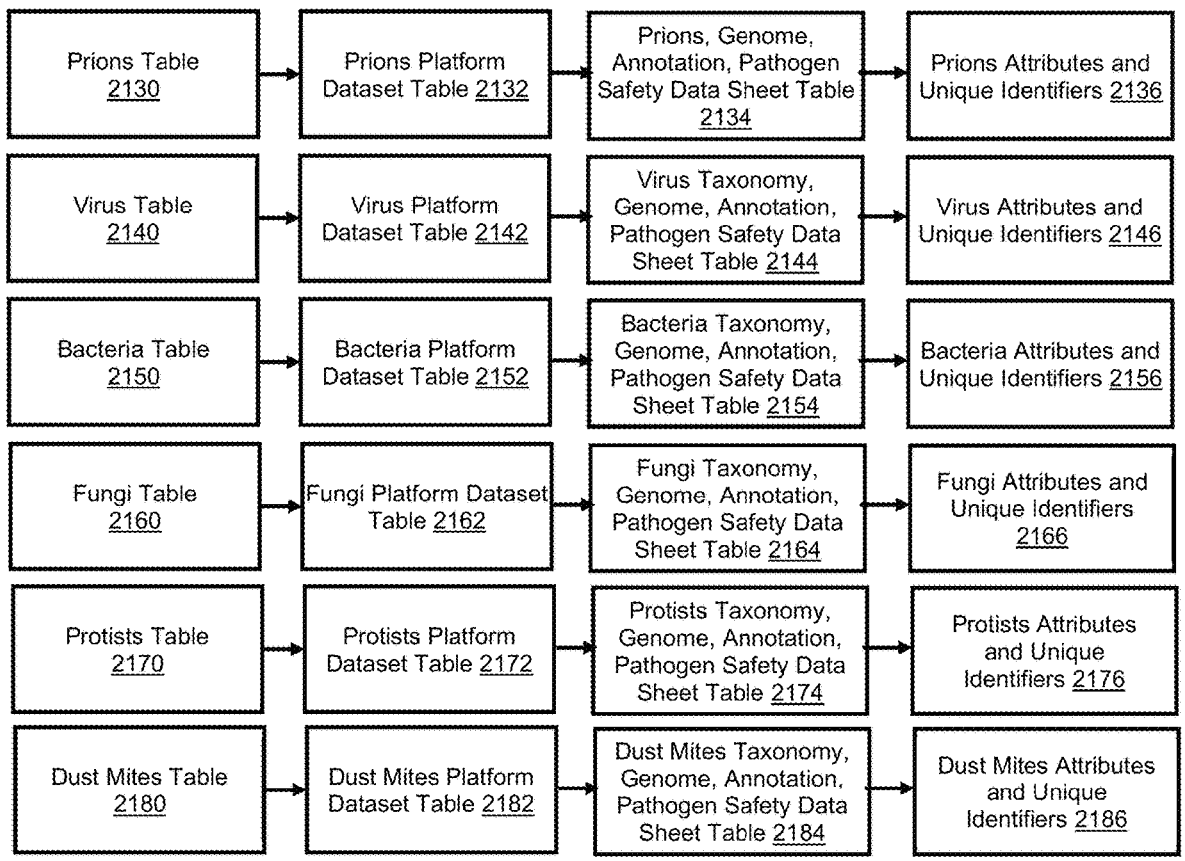
FIG. 21 is an example microorganism data, and a microorganism database, according to some embodiments.

FIG. 21 is an example microorganism data 2110, and a microorganism database 2120, according to some embodiments.

The microorganism data 2110 contains genomic information derived from platform datasets, annotation information, pathogen safety data sheets, attributes, and unique identifiers based on the particle detection methods 2500 used.

The microorganism database 2120 comprises following important tables:

Prions Table 2130 which comprises: Prions Platform Dataset Table 2132, Prions, Genome, Annotation, Pathogen Safety Data Sheet Table 2134, Prions Attributes and Unique Identifiers 2136;

Virus Table 2140 which comprises: Virus Platform Dataset Table 2142, Virus Taxonomy, Genome, Annotation, Pathogen Safety Data Sheet Table 2144, Virus Attributes and Unique Identifiers 2146;

Bacteria Table 2150 which comprises: Bacteria Platform Dataset Table 2152, Bacteria Taxonomy, Genome, Annotation, Pathogen Safety Data Sheet Table 2154, Bacteria Attributes and Unique Identifiers 2156;

Fungi Table 2160 which comprises: Fungi Platform Dataset Table 2162, Fungi Taxonomy, Genome, Annotation, Pathogen Safety Data Sheet Table 2164, Fungi Attributes and Unique Identifiers 2166;

Protists Table 2170 which comprises: Protists Platform Dataset Table 2172, Protists Taxonomy, Genome, Annotation, Pathogen Safety Data Sheet Table 2174, Protists Attributes and Unique Identifiers 2176;

Dust Mites Table 2180 which comprises: Dust Mites Platform Dataset Table 2182, Dust Mites Taxonomy, Genome, Annotation, Pathogen Safety Data Sheet Table 2184, Dust Mites Attributes and Unique Identifiers 2186;

The curated microorganism database 2120 containing the unique identifiers associated with particle detection methods 2500 allows for fast detection, and reporting a given microorganism for a given type of biosensors 2202.

The microorganism database 2120 contains publicly available as well as curated information such as taxonomy, morphology, organelles, physiology, cultivation, geographic origin, application, interaction or sequences for genomes, images. Apart from images taken by wearable device 100 microbial biosensor 310 and particulate matter sensor 320, the microorganism database 2120 also contains the images and other identification information obtained from other orthogonal or comparator detection methods such as electron microscope images, scanning probe microscope, surface enhanced Raman spectroscopy, surface plasmon resonance and so on. This comparator detection methods information allows to increase the accuracy of microorganisms 610 detection.

Figure 22:
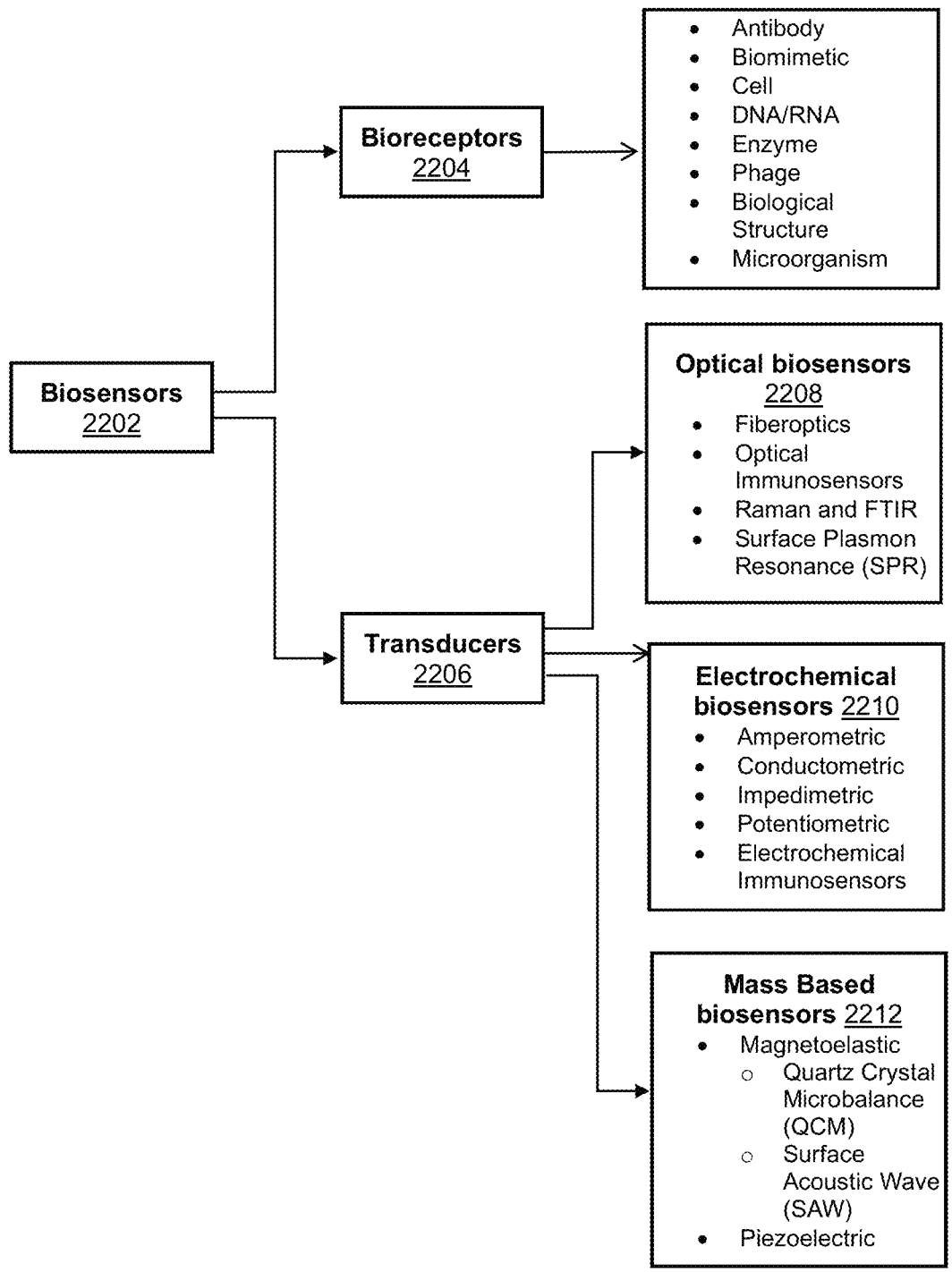
FIG. 22 illustrates biosensors classification based on bioreceptors and transducers, according to some embodiments.

FIG. 22 illustrates biosensors classification based on bioreceptors and transducers 2200, according to some embodiments.

Biosensors 2202 are devices used to detect the presence or concentration of bioreceptors 2204. The bioreceptors 2204 or biological analyte or element comprises antibody, biomimetic, cell, DNA/RNA, enzyme, phage, a biological structure, a microorganism comprising a prion 612, a virus 614, a bacterium 616, a fungus 618, a protist 620, a dust mite 622, a tissue, and so on. It has a sensor that integrates a biological element with a physiochemical transducer to produce an electronic signal proportional to an analyte, which is then conveyed to a detector. The process of signal generation (in the form of light, heat, pH, charge, or mass change, etc.) upon interaction of the bioreceptor with the analyte is termed bio-recognition. Biosensors consist of three parts: a component that recognizes the analyte and produces a signal, a signal transducer with an amplifier, and a reader device. The transducers 2206 are elements that convert one form of energy into another. In a biosensor the role of the transducers 2206 is to convert the bio-recognition event into a measurable signal. Most transducers 2206 produce either optical or electrical signals that are usually proportional to the amount of analyte—bioreceptor interactions.

The biosensors 2202 are classified based on the biological analyte used in the analysis or the method of transduction implemented. The most common classification of biosensors 2202 is based on the type of transducers 2206 or transduction used in the sensor i.e., type of physiochemical resulting from the sensing event. The biosensor types are:

1) Optical biosensors 2208 are most common type of biosensor. They can be label-free or label-based. Optical biosensors 2208 biosensors measure the interaction of an optical field with a biorecognition sensing element. They include infrared light sensor, fluorescence, and surface enhanced Raman spectroscopy (SERS). Detection can be colorimetric, which measures changes in light adsorption or photometric, which measures light intensity. The method used can be fiber optics, Raman and Fourier transform infrared spectrometer (FTIR), and surface plasmon resonance (SPR). Optical immunosensors are affinity ligand-based biosensor solid-state devices in which the immunochemical reaction is coupled to a transducer. This sensor is based on an immunochemical reaction comprised of an antigen or antibody as the biorecognition element that is immobilized on a transducer surface. The wearable device 100 uses optical methods of infrared spectroscopy 2510, fluorescence imaging 2520, particle imaging 2530, nucleic acid sequence identification 2540, and light scattering and imaging 2570;

2) Electrochemical biosensors 2210 react with an analyte of interest to produce an electrical signal proportional to the analyte concentration. Electrochemical biosensors 2210 can be Amperometric, which measures current due to the reduction or oxidation of electroactive species, Conductometric, which is based on measurement of electrical conductivity in a sample solution between two electrodes because of the biochemical reaction, Impedimetric, which measures the variation in resistance, or Potentiometric, which measures variations in open circuit potential, converting the chemical information into a measurable electrical signal. Electrochemical immunosensors rely on the measurements of an electrical signal recorded by an electrochemical transducer. They can be classed as amperometric, potentiometric, conductometric, or impedimetric depending on the signal type. Thermometric biosensors biological reactions are associated with the release of heat. Thermometric biosensors measure the temperature change of the solution containing the analyte caused by these enzymatic reactions. The wearable device 100 can use thermometric biosensors which release heat when light of certain wavelengths strikes the microorganisms 610.

3) Mass based biosensors 2212 such as acoustic biosensors or piezoelectric biosensors measure the change in the physical properties of an acoustic wave or in case of magnetic biosensors, measure changes in magnetic properties or magnetically induced effects. They also include quartz crystal microbalance (QCM) and surface acoustic wave (SAW). The wearable device 100 can use electromagnetic waves-based impedance spectroscopy by varying radio wave frequencies, so that changes in microorganism 610 response can be determined.

There are a few other biosensors 2202 like:

4) Ultrasound sensors are for directing sound waves toward a surface and measuring the reflected echoes. Echoes are different depending on the density of the microorganism 610 that the ultrasound waves hit. There have been experiments with acoustic reporter genes to scatter sound waves coupled with cell structure high resolution imaging techniques that can also be used to detect microorganism 610. Listening to the unique sound of one microorganism is possible through the picotube 2454 microphone. There are four types of ultrasonic sensors, classified by frequency and shape: the drip-proof type (for outdoor use), high-frequency type (double feed detection), and open structure type lead type (distance detection/moving object detection), and standardized mean difference—SMD type (distance detection and object detection).

FIG. 23 illustrates an electromagnetic spectrum 2300, and a spectrum of sound 2350, according to some embodiments.

The electromagnetic spectrum 2300 is classified as being either ionizing or non-ionizing. Ionizing radiation is of shorter wavelength/high frequency with high energy. Non-ionizing radiation is longer wavelength/lower frequency with lower energy. The ionizing radiation is usually harmful to humans. The electromagnetic spectrum 2300 consists of Gamma rays, X rays, Ultraviolet, Laser, Visible light, Infrared, Microwave, Radio waves, and corresponding applications such as a scintigraphy, a dental/chest, scopes like microscope, thermal imaging, cancer, electro surgery, and MRI (magnetic resonance imaging). The gamma ray's wavelength is shortest and radio wave the longest. The diagram also describes the sizes of elements like atomic nuclei, atoms, microorganisms 610, pinpoints, bee, humans, and a building. The particle detection methods 2500 use electromagnetic spectrum 2300, which is not harmful to humans or the surface 3050. The regions are ultraviolet, laser, infrared, and part of micro and radio waves.

The spectrum of sound 2350 consists of inaudible sounds (20 Hz), audible sounds (200 Hz to 20 kHz), and inaudible sounds which are greater than 200 MHz. The use of picomaterials 2450 allows for ultrasound echo, images, and listening to sound of microorganisms 610.

FIG. 24 illustrates a noninvasive biosensors for particle detection and sterilization list 2410, picomaterials 2450, and particle detection methods working principle list 2490, according to some embodiments.

The noninvasive biosensors for particle detection and sterilization list 2410 describes in detail the microorganisms 610 detected, biosensor detector used, type of biosensor/transducer, measurement condition, and microorganism detection method.

The microbial biosensor 310 sterilizer 316 allows for sterilization using heat, ultraviolet light, wavelengths of certain type, and acoustic waves to lyse and kill microorganisms 610.

The picomaterials 2450 consists of picoparticle 2452, picotube 2454, picofiber 2456, and picorod 2458. Picomaterials 2450 have diameters below the wavelength of the guided light. The material size can be in pico, nano, and micrometer. These tiny fibers offer engineerable waveguiding properties including optical confinement, fractional evanescent fields, and surface intensity for optical sensing on the pico/nano/micro scale. The material used for manufacturing the microbial sensor 310, particulate matter sensor 320, and enviro sensor 330 contain picomaterials 2450. The microbial biosensor 310, transmitter 312, receiver 314, sterilizer 316, and picocamera 318 are built using picomaterials 2450.

The particle detection methods working principle list 2490 describes the microorganism detection method corresponding to microorganisms' attributes based unique identifiers. The unique identifiers are predetermined and available in the microorganism database 2120. The artificial intelligence methods allow for calculating the unique identifiers for a new microorganism 610 or new variant/strain based on existing microorganism data 2110.

FIG. 25 illustrates particle detection methods 2500, according to some embodiments.

The method of claim 14, wherein the step of detecting the pathogen and beneficial microorganisms inside the nasal cavity 2840, oral cavity 2890, or on the surface 3050 with the microbial biosensor 310 and particulate matter sensor 320 comprises: particle detection methods 2500 of infrared spectroscopy 2510, fluorescence imaging 2520, particle imaging 2530, nucleic acid sequence identification 2540, electromagnetic waves 2550, ultrasound waves 2560, and light scattering and imaging 2570.

The microbial biosensor 310 and particulate matter sensor 320 use particle detection methods 2500 to detect microorganisms 610, pollen grains 630, and dust mite allergens 640.

The microbial biosensor 310 based methods use a transmitter 312, receiver 314, sterilizer 316, and a picocamera 318. The receiver 314 is programmed to function as transmitter 312 and vice-versa for fluorescence imaging 2520, particle imaging 2530, and nucleic acid sequence identification 2540 detection methods.

The object 2502 can be a nasal cavity 2840, an oral cavity 2890, or on a surface 3050.

The particle detection methods 2500 comprises:

1. Infrared spectroscopy 2510 (IR spectroscopy) which is the measurement of the interaction of infrared radiation with matter by absorption, transmission, or reflection. Infrared spectroscopy 2510 is used to identify chemical composition and substances or functional groups in microorganisms 610. The infrared spectroscopy 2510 is spectra of intact microorganisms' 610 cells with highly specific fingerprint-like signatures which are used to differentiate, classify, and identify diverse microorganism 610 species and strains. The infrared portion of the electromagnetic spectrum 2300 is usually divided into three regions; the near-, mid-, and far-infrared, named for their relation to the visible light. The infrared radiation in the wavelength near- and mid-infrared region of 305-3,000 nm is used so that a user 3802 measurement area can be exposed without adverse health effects. The method can use Fourier Transform IR (FT-IR) spectroscopy. IR spectroscopy exploits the fact that molecules absorb specific frequencies that are characteristic of their structure. Microorganisms' 610 IR spectra are also useful to detect intracellular structures, components, and chemical composition. The fingerprint-like patterns generated by the absorption or transmission of IR light by cell structure components and chemical composition are highly specific and are used to classify microorganisms according to their phenotype. Identification of microorganisms 610 at the species level is done by comparison of detected spectra to the reference spectra in the microorganism database 2120. The steps to detect microorganisms 610 using the infrared spectroscopy 2510 method are as follows:

a. Throw a beam of infrared light 2512 on an object 2502. The object 2502 can be a nasal cavity 2840, an oral cavity 2890, or on a surface 3050.

b. Some of the IR light is absorbed, some IR light is transmitted 2516, and the remaining IR light reflected 2514 is received by the receiver 314.

c. The % transmittance (T), % reflectance (R), and % absorbance (A) are recorded in the digital format. These numbers are unique to microorganisms 610 based on their chemical composition. The infrared spectrum of a microorganism 610 can be visualized in a graph 2518 of infrared light as % transmittance (T), % reflectance (R), and % absorbance (A), on the vertical Y-axis. The X-axis of an IR spectrum is labeled as "Wavelength" and provides the absorption number.

2. Fluorescence imaging 2520 is a type of noninvasive imaging technique that allows detection of biological molecular structures in a microorganism 610. Fluorescence measurement can be based on variety of methods such as imaging using picocamera 318, and spectroscopy. Fluorescence imaging 2520 can use particle imaging 2530 detection methods to analyze images. Fluorescence imaging 2520 involves taking pictures of the radiation emitted by the microorganisms 610 using picocamera 318 and analyzing it. Fluorescence is a specific radiation emitted by the microorganisms 610 because of incident radiation of a certain wavelength. Fluorescence is a form of luminescence. The emitted light usually has a longer wavelength, and lower energy, than the absorbed radiation. Fluorescence spectroscopy is like infrared spectroscopy 2510. Fluorescence in several wavelengths such as interval from 10 to 200 nm in the ultraviolet region can be detected by an array detector made of picomaterials 2450. The receiver 314 is configured to act as transmitter 312 in this mode. The steps to detect microorganisms 610 using a fluorescence imaging 2520 method are as follows:

a. Irradiate a beam of excitation light 2522 and 2524 on an object 2502 with a desired and specific band of wavelengths using transmitter 312 and receiver 314.

b. Separate the much weaker emitted fluorescence from the excitation light 2522 and 2524.

c. Take an image and videos of the object 2502 using picocamera 318. The image and videos are analyzed using image analysis working principle 2660, and microorganisms 610 are detected. The microorganisms 610 image taken by picocamera 318 also allows for detection of cells and subcellular structures. The image 2528 is an example rod shaped bacteria 614 identified using fluorescence imaging.

3. Particle imaging 2530 is the process of making a digital representation of microorganisms 610 by taking a picture or photo with a picocamera 318. The receiver 314 is configured to act as transmitter 312 in this mode. Photons are too large to see individual atoms, molecules, proteins, and microorganisms 610, pollen grains 630, and dust mite allergens 640. In the particle imaging 2530 method, photons are passed through and aimed at the end of picotubes 2454 and picofibers 2456, the photon is compressed to much smaller dimension than usual size, and photon quarks strike the nasal cavity 2840, or oral cavity 2890, or surface 3050 and are absorbed and re-emitted. This allows individual atoms to be seen. The light in this case is shrunk or compressed. The picotubes 2454 and picofibers 2456 can also contain silver or gold needle or other material at the tip to compress the photon. The steps to detect microorganisms 610 using microbial biosensor 310 using a particle imaging 2530 method are as follows:

a. Irradiate a beam of excitation light 2532 and 2534 on an object 2502 with a desired and specific band of wavelengths using transmitter 312 and receiver 314.

b. Take multiple high-magnification images of microorganisms 610 using picocamera 318.

c. Analyze images and videos using image analysis working principle 2660, and microorganisms 610, pollen grains 630, and dust mite allergens 640 are detected. During image analysis the nasal cavity 2840 tissues, oral cavity 2890 tissues, and surface 3050 features are masked out for accurate determination of microorganisms 610. To speed up the detection, a user 3802 can set up and record the nasal cavity and oral cavity images to mask out the tissues. The image 2538 is an example colony of cocci shaped bacteria 614 identified by the particle imaging 2530 method.

4. Nucleic acid sequence identification 2540 is noninvasive identification of a succession of bases signified by a series of a set of five different letters that indicate the order of nucleotides forming alleles within a DNA (using GACT) or RNA (GACU) molecule. The process involves taking high-resolution images at multiple magnification using a particle imaging 2530 technique and picocamera 318 as follows:

a. Irradiate a beam of excitation light 2542 and 2544 on an object 2502 with a desired and specific band of wavelengths using transmitter 312 and receiver 314.

b. Take multiple high-magnification images of microorganisms 610 using picocamera 318.

c. Analyze images and videos using image analysis working principle 2660, and microorganisms 610 are detected. Classify microorganisms 610 at a high level based on shape, size, and other structural components attributes.

d. Analyze the next higher magnification images and find the presence of DNA/RNA area, chromatin, and nucleus area within images.

e. Analyze the next higher magnification images of DNA/RNA and tag them as ATGCU based on structural bond.

f. Create a nucleotide sequence, align the sequence in microorganism database 2120, and identify the microorganism at genus and species levels. The sequence 2546 is an example segment of a SARS-CoV-2 virus sequence.

5. Electromagnetic waves 2550 is based on the principle of a Hall effect sensor. As described in FIGS. 8, 11, 14, and 17, chemical composition and elements in some microorganisms 610 are ferromagnetic. The electromagnetic waves 2550 method uses transmitter 312 designed like a solenoid coil made of picofibers 2456 to generate a magnetic field or flux 2552 which strikes the nasal cavity 2840, or oral cavity 2890, or surface 3050. The magnitude of the magnetic field changes if the microorganism 610 contains ferromagnetic material. A Hall sensor array at the receiver 314 detects the presence and magnitude of a magnetic field 2554 using the Hall effect.

The steps to detect microorganisms 610 using the electromagnetic waves 2550 method are as follows:

a. Direct electromagnetic waves 2552 toward a surface of an object 2502. The magnitude of the intensity changes if microorganisms 610 contains ferromagnetic material.

b. The Hall sensor array at the receiver 314 detects the presence and magnitude of a magnetic field 2554 using the Hall effect.

c. Measure the magnitude of a magnetic field 2554 using the Hall effect. The magnitude of the magnetic field 2554 is different depending on microorganisms' 610 ferromagnetic composition.

The electromagnetic waves 2550 method is more suitable for microorganisms 610 containing ferromagnetic materials.

6. Ultrasound waves 2560 involve directing sound waves toward a surface of an object 2502 and measuring the reflected echoes. Echoes are different depending on the density of the microorganisms 610 that the ultrasound waves hit. In certain cases, microorganisms 610 can also contain acoustic reporter genes to scatter sound waves, coupled with imaging the cell structure in a high-resolution imaging technique to detect it. The other technique used is to listen to the unique sound of one microorganism 610 through picotube 2454 microphone.

The steps to detect microorganisms 610 using the ultrasound waves 2560 method are as follows:

a. Direct sound waves 2562 toward a surface of an object 2502. The objects 2502 are usually hard surfaces.

b. Some of the sound waves reflected 2564 are received by the receiver 314.

c. Measure the reflected echoes. Echoes are different depending on the density of the microorganism that the ultrasound waves hit.

The ultrasound waves 2560 method is more suitable for a hard surface than a nasal cavity 2840 or oral cavity 2890.

7. Light scattering and imaging 2570 is analysis of reflection patterns of incident laser light from the outer surface of microorganisms 610, pollen grains 630, and dust mite allergens 640.

The steps to detect microorganisms 610 using light scattering and imaging 2570 are as follows:

a. Laser 2572 beam radiates suspended particles 2576 in the air entering through an air channel.

b. Collect scattering light through detector 2574 in a certain degree 0 and obtain the curve of scattering light change with time. The raw electric signal is amplified. Equivalent particle diameter and the number of particles with different diameters per unit volume are calculated based on the MIE theory of absorption and scattering of plane electromagnetic waves by uniform isotropic particles of the simplest form.

c. Record the particle size number in the digital format. These numbers are unique to microorganisms 610 based on the size. Light scattering of a microorganism 610 can also be visualized in a graph 2580 of scattering of reflectance, on the vertical Y-axis. The X-axis is labeled as "Particle size" and provides the particle size number.

The imaging system uses the microbial biosensor 310 hardware. The steps of imaging using particle imaging 2530 detection method principles are as follows:

a. Irradiate a beam of excitation light 2578 and 2580 on the particle 2576 with a desired and specific band of wavelengths.

b. Take multiple high-magnification images of particles 2576 when they are in front of a special darkfield photographic plate 2582 using picocamera 318.

c. Analyze images and videos using image analysis working principle 2660, and detect microorganisms 610, pollen grains 630, and dust mite allergens 640. During image analysis the nasal cavity 2840 tissues, oral cavity 2890 tissues, and surface 3050 features are masked out for accurate determination of microorganisms 610. To speed up the detection, a user 3802 can set up and record the nasal cavity and oral cavity images to mask out the tissues. The example image 2590 contains an influenza virus, cocci bacteria, and fungi identified using high resolution imaging.

The microbial biosensor 310 and particulate matter sensor 320 particle comprising detection methods 2500 of infrared spectroscopy 2510, fluorescence imaging 2520, particle imaging 2530, nucleic acid sequence identification 2540, electromagnetic waves 2550, ultrasound waves 2560, and light scattering and imaging 2570 also allow to detect particles like small molecules, lipids, proteins and so on.

Figure 26:
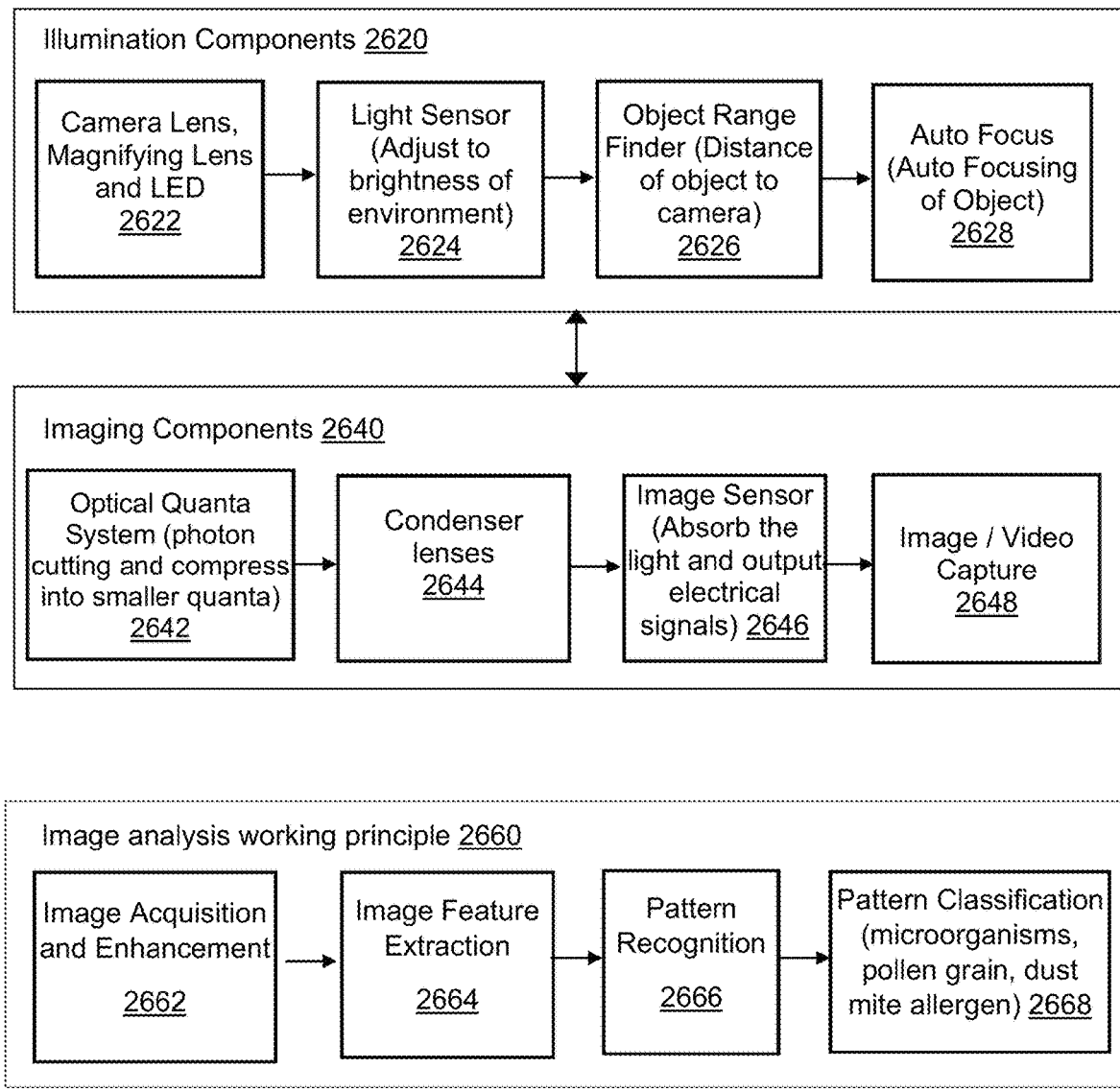
FIG. 26 illustrates an example picocamera hardware comprising illumination components and imaging components, and an image analysis working principle that can be utilized to implement various embodiments.
Figure 37:
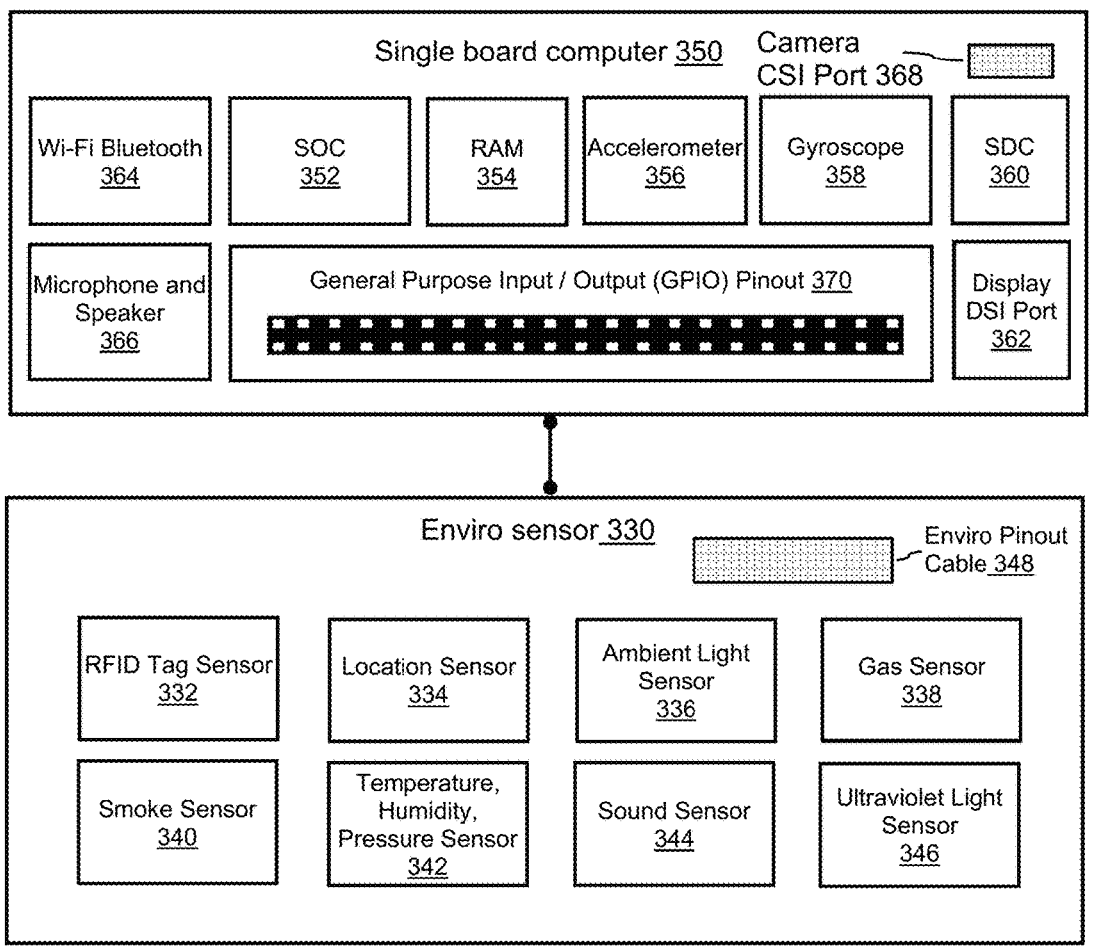
FIG. 37 is an example single board computer and enviro sensor circuit block diagram and enviro sensor wiring table, according to some embodiments.

FIG. 26 illustrates an example picocamera 318 hardware comprising illumination components 2610 and imaging components 2640, and an image analysis working principle 2660 that can be utilized to implement various embodiments.

The intended use of the picocamera 318 is to take photos and videos of the nasal cavity 2840, an oral cavity 2890, or surface 3050 which can be used for nasal ID, open mouth ID, and surface ID recognition. The particle detection methods 2500 use picocamera 318 and take the small particles such as small molecule, protein, microorganism 610, and pollen grain image pictures and videos, and after image analysis identify microorganism 618 type, pollen grain 630, and dust mite allergen 640. Picocamera 318 can be operated in both normal mode and high magnification mode. The picocamera 318 picofibers 2456 scan the nasal cavity 2840, the oral cavity 2890, or the surface 3050 to create a set of super high-resolution images, enhance images, extract features, perform pattern matching, and using applicable fluorescence imaging 2520, particle imaging 2530, nucleic acid sequence identification 2540, and light scattering and imaging 2570 methods, detect the following:

the pathogen count, the pathogen type, the pathogen concentration, and the pathogen biosafety level;

the beneficial microorganism count, the beneficial microorganism type, and the beneficial microorganism concentration;

a pollen type, a pollen count, and a pollen allergy level;

a dust mite allergen count, and dust mite allergy level;

The picocamera 318 illumination components 2620 comprise: camera lens, magnifying lens, and LED 2622, light sensor 2624 to adjust to brightness of environment, object range finder 2626, which allows finding of the distance of the object to picocamera 318 (in this case, the distance of wearable device 100 to the nasal cavity 2840, oral cavity 2890, and surface 3050), and finally auto focus 2628, which allows for auto focusing of objects.

The picocamera 318 imaging components 2640 comprise: optical quanta system 2642 responsible for photon cutting or slicing and compressing it into smaller quanta using picomaterials 2450 such as picotube 2454, picofiber 2456, and picorod 2458; condenser lenses 2644 to gather the quanta or sub photon based on resolution required in pm, nm, or mm in size of the first crossover image and focus them onto a nasal cavity 2840, an oral cavity 2890, or on a surface 3050 to illuminate only the area being examined. A condenser is a lens that concentrates the light on a measurement area and increases the resolution. An image sensor 2646 absorbs the light and output electrical signals; and image/video capture 2648 stores the digital image and video.

The image analysis working principle 2660 comprises: image acquisition and enhancement 2662, image feature extraction 2664, pattern recognition 2666, and particle pattern classification 2668. The image analysis working principle 2660 includes taking microorganism 610, pollen grain 630, dust mite allergen 640, and surface 3050 photos and classification of the microorganisms 610, pollen grains 630, and surfaces 3050 based on machine learning algorithms. In the processing step image acquisition and enhancement 2662, photos are taken, and an algorithm converts the photo into a digital format. In the case of videos, a video image processing system is used to process frames of the video clip. In processing step image feature extraction 2664, an initial set of the raw photo data and video frames is divided and reduced to more manageable groups. The input photo image and video frames are transformed into a reduced set of features. The processing step pattern recognition 2666 is the process of recognizing patterns by using a machine learning algorithm. The image pattern recognition involves classification of feature extracted data in recognizing the microorganisms 610, pollen grains 630, and dust mites allergens 640 types. In the processing step pattern classification 2668, particle detection methods 2500 detect the following:

the pathogen count, the pathogen type, the pathogen concentration, and the pathogen biosafety level;

the beneficial microorganism count, the beneficial microorganism type, and the beneficial microorganism concentration;

a pollen type, a pollen count, and a pollen allergy level;

a dust mite allergen count, and dust mite allergy level;

The videos are used to increase the sensitivity of the results using video processing, using images as the data format to store the video frames. This is very helpful in case the photo images taken are blurry.

FIGS. 27, 28, 29, and 30 illustrate example wearable device 100 microbial biosensor 310 implementation and working.

FIG. 27 illustrates an example microbial biosensor pinout 2710 and a microbial biosensor wiring table 2750 describing the hardware wiring connection steps of a microbial biosensor pinout 2710 connected to the single board computer general purpose input output pinout 370 that can be utilized to implement various embodiments.

1. Log in to the single board 350 computer operating software and access general purpose input output pinout 370 settings. Assign and map the general purpose input output pinout 370 to be connected to a microbial biosensor pinout 2710. Save general purpose input output pinout 370 settings.

2. Connect the microbial biosensor pinout 2710 to a single board computer 350 assigned general purpose input output pinout 370 as listed in the microbial biosensor wiring table 2750. The hardware implementation of the microbial biosensor 310 is complete after the pathogen biosensor pinout 2710 is connected to a single board computer 350 general purpose input output pinout 370.

3. Prepare the single board computer 350 operating software to communicate with the microbial biosensor 310 by loading the general purpose input output pinout 370 software library and installing the microbial biosensor 310 software driver.

4. Program, install, execute, and run the microbial biosensor 310 software on the single board computer 350 operating software.

The microbial biosensor 310 software is part of microbiome application software 250.

The microbial biosensor 310 has seven dedicated channels for detecting microorganisms 610, pollen grains 630, and dust mite allergens 640 as follows:

PRI OUT 2714—Output channel for prions 612
VIR OUT 2716—Output channel for viruses 614
BAC OUT 2718—Output channel for bacteria 616
FUN OUT 2720—Output channel for fungi 618
PRO OUT 2722—Output channel for protists 620
DUS OUT 2724—Output channel for dust mites 622
POL OUT 2726—Output channel for pollen grains 630 and dust mite allergens 640

The individual dedicated channel for each microorganism 610, pollen grain 630 and dust mite allergen 640 allow for fast high throughput multiplexed detection. Each output channel 2714 to 2726 is dedicated to use the best particle detection methods 2500 based on microorganism 610 types, and pollen grain 630. The microorganisms 610 limit of detection (LOD) is based on the measurement resolution. Particle detection methods 2500 with higher resolution images like particle imaging 2530 and light scattering and imaging 2570 allow for detection of microorganisms in the range of 1 to 10. The microbial biosensor 310 methods allow for faster detection of microorganism 610 clusters, pollen grain 630 clusters, and dust mites allergen 640 clusters.

The processing units 2742 are used for dedicated calculations of microorganism 610 count and concentration.

The microbial biosensor 310 uses particle detection methods 2500 to detect microorganisms 610 comprised as follows:

The microbial biosensor 310 detects, measures, and monitors a pathogen count, a pathogen type, a pathogen concentration, and a pathogen biosafety level in a nasal cavity 2840, an oral cavity 2890, or on a surface 3050;

The microbial biosensor 310 also detects, measures, and monitors a beneficial microorganism count, a beneficial microorganism type, and a beneficial microorganism concentration in a nasal cavity 2840, an oral cavity 2890, or on a surface 3050; and The sterilizer 316 kills the pathogenic microorganism 610. The method used to kill or sterilize the microorganisms 610 can be heat, acoustic waves, ultrasound, ultraviolet light, and so on.

FIG. 28 illustrates an example microbial biosensor infrared spectroscopy sensing working principle diagram 2810 and a microbial biosensor particle imaging working principle diagram 2850 that can be utilized to implement various embodiments.

A microbial biosensor 310 is a device that detects microorganisms 610. Microorganisms detected include both beneficial microorganism and pathogenic microorganisms, also known as pathogens. A microbial biosensor 310 is an electronic component that utilizes optical, mass based, and acoustic sensors to detect microorganisms 610 and kill pathogens. The intended use of the microbial biosensor 310 is to detect, measure, and monitor pathogen types, concentrations, and biosafety levels, and kill pathogens in a nasal cavity 2840, an oral cavity 2890, or on a surface 3050 of the object. The microbial biosensor 310 also detects, measures, and monitors a beneficial microorganism count, a beneficial microorganism type, and a beneficial microorganism concentration in a nasal cavity 2840, an oral cavity 2890, or on a surface 3050 of the object. The microorganisms 610 detected can be prions, viruses, bacteria, fungi, protists, dust mites, and so on. The microbial biosensor 310 consists of a transmitter 312, a receiver 314, and a sterilizer 316. The transmitter 312 can transmit light energy as well as ultrasound signals. The receiver 314 can receive the reflected light and reflected ultrasound signals. The sterilizer 316 can transmit antipathogen ultraviolet energy 2818, antipathogen ultrasound energy 2858, and heat.

The microbial biosensor infrared spectroscopy working principle diagram 2810 illustrates the detection of microorganisms 610 using infrared spectroscopy 2510 and sterilization of pathogens using antipathogen ultraviolet energy 2818. The steps to detect microorganisms 610 using the infrared spectroscopy 2510 method are as follows:

a. Throw a beam of transmitted infrared light 2812 on a nasal cavity 2840.

b. Some of the infrared light is absorbed, some infrared light is transmitted in the form of transmission/absorption 2814, and remaining reflected infrared light 2816 is received by the receiver 314.

c. The % transmittance (T), % reflectance (R), and % absorbance (A) are recorded in the digital format. These numbers are unique and allow for detection of microorganisms 610 based on their chemical composition.

The pathogens or pathogenic microorganisms 610 are killed or sterilized by the safe antimicrobial sterilizer 316 of the microbial biosensor 310. The antipathogen ultraviolet energy 2818 is focused toward the area of nasal cavity 2840 where there are pathogenic microorganisms 610. The antipathogen ultraviolet energy 2818 destroys the pathogens' cell covering, protein, or nucleic acids by killing or inactivating the microorganisms 610.

The microbial biosensor particle imaging working principle diagram 2850 illustrates the detection of microorganisms 610 using particle imaging 2530 and sterilization of pathogens using antipathogen ultrasound energy 2858. The receiver 314 is configured to act as transmitter 312 in this mode. The steps to detect microorganisms 610 using the particle imaging 2530 method are as follows:

a. Irradiate a beam of transmitted excitation light 2852 and 2854 on an oral cavity 2890 with a desired and specific band of wavelengths using transmitter 312 and receiver 314.

b. Take multiple high-magnification images of microorganisms 610 using picocamera 318.

c. Analyze image and videos using image analysis working principle 2660, and microorganisms 610, pollen grains 630, and dust mite allergens 640 are detected.

The microorganisms 610 are killed or sterilized by the sterilizer 316 of the microbial biosensor 310. The high frequency antipathogen ultrasound energy 2858 is suitable for sterilization and is used for cell disruption to kill pathogenic microorganisms 610.

The microbial biosensor 310 infrared spectroscopy 2510 and particle imaging 2530 allow easy-to-use, rapid, portable, multiplexed, and cost-effective detection of microorganisms 610.

The wearable device 100 sends a pathogen biosafety alert 4310 to the microbiome mobile application 250 of the user 3802 when the pathogen biosafety level is above a predetermined threshold level in the nasal cavity 2840, oral cavity 2890, surface 3050, or in the air surrounding the user 3802.

The microbial biosensor 310 sterilizer 316 kills pathogens. When the biosafety level is still above a predetermined threshold level in the wearable device 100, the user 3802 can select appropriate sterilization methods.

FIG. 29 and FIG. 30 illustrates a microbial biosensor 310 nasal cavity test method, oral cavity test method, and a surface test method and sterilization diagrams.

FIG. 29 illustrates a microbial biosensor nasal cavity test method diagram 2910 and microbial biosensor oral cavity test method diagram 2950 that can be utilized to implement various embodiments.

A method comprising a wearable device 100 consisting of a smart band 200 and a display unit 102.

The smart band 200 comprises a microbial biosensor 310, a particulate matter sensor 320, an enviro sensor 330, a single board computer 350, a power supply unit 380, a band fastener 202, and a set of watch adapters 204 and 206.

The display unit 102 comprises a touchscreen 104, a display unit power button 106, a crown 108, and a set of attachment slots 110 and 112.

The microbial biosensor 310 comprises a transmitter 312, a receiver 314, a sterilizer 316, a picocamera 318, and a microbial biosensor power button 319.

The particulate matter sensor 320 comprises a sensing cavity 322.

The enviro sensor 330 comprises a set of sensors 332-346.

The power supply unit 380 comprises a wireless charging unit 382, a battery 384, a charging port 386, and a band power button 388.

A microbiome mobile application 250 allows user to access the wearable and sensor data.

A user 3802 wears a wearable device 100.

The method of operating the wearable device 100 microbial biosensor nasal cavity test method diagram 2910 comprises the following steps:

1. Strap the wearable device 100 around the wrist 2912 of the user 3802;

2. Power on the wearable device 100 by pressing the band power button 388;

3. Power on the microbial biosensor 310 by pressing the microbial biosensor power button 319;

4. Face the microbial biosensor 310 to a nasal cavity 2840 of the user 3802;

5. Auto verify the identity of the nasal cavity 2840 of the user 3802;

6. Detect a pathogen inside the nasal cavity 2840 of the user 3802 with the microbial biosensor 310;

7. Display a pathogen count, a pathogen type, a pathogen concentration, and a pathogen biosafety level on the microbiome mobile application 250;

8. Detect a beneficial microorganism inside the nasal cavity 2840 of the user 3802 with the microbial biosensor 310;

9. Display a beneficial microorganism count, a beneficial microorganism type, and a beneficial microorganism concentration on the microbiome mobile application 250;

10. Sterilize the pathogen type found by pressing and holding the microbial biosensor power button 319; and 11. Power off the microbial biosensor 310 by pressing the microbial biosensor power button 319.

The exemplary microbial biosensor nasal cavity test method diagram 2910 shows detection of microorganisms 610 in a nasal cavity 2840 using infrared spectroscopy 2510 and particle imaging 2530 methods.

The method of operating the wearable device 100 microbial biosensor oral cavity test method diagram 2950 comprises the following steps:

1. Strap the wearable device 100 around the wrist 2912 of the user 3802;

2. Power on the wearable device 100 by pressing the band power button 388;

3. Power on the microbial biosensor 310 by pressing the microbial biosensor power button 319;

4. Face the microbial biosensor 310 to an oral cavity 2890 of the user 3802;

5. Auto verify the identity of the oral cavity 2890 of the user 3802;

6. Detect the pathogen inside the oral cavity 2890 of the user 3802 with the microbial biosensor 310;

7. Display the pathogen count, the pathogen type, the pathogen concentration, and the pathogen biosafety level on the microbiome mobile application 250;

8. Detect the beneficial microorganism inside the oral cavity 2890 of the user 3802 with the microbial biosensor 310;

9. Display a beneficial microorganism count, a beneficial microorganism type, and a beneficial microorganism concentration on the microbiome mobile application 250;

10. Sterilize the pathogen type found by pressing and holding the microbial biosensor power button 319; and 11. Power off the microbial biosensor 310 by pressing the microbial biosensor power button 319.

The exemplary microbial biosensor oral cavity test method diagram 2950 shows detection of microorganisms 610 in an oral cavity 2890 using infrared spectroscopy 2510 and particle imaging 2530 methods.

FIG. 30 illustrates a microbial biosensor surface test method diagram 3010, and surface 3050 types that can be utilized to implement various embodiments.

The method of claim 13, further operating the wearable device 100 microbial biosensor surface test method comprises the following steps:

1. Strap the wearable device 100 around the wrist 2912 of the user 3802;

2. Power on the wearable device 100 by pressing the band power button 388;

3. Power on the microbial biosensor 310 by pressing the microbial biosensor power button 319;

4. Face the microbial biosensor 310 to a surface 3050;

5. Auto verify the identity of the surface 3050;

6. Detect the pathogen on the surface 3050 with the microbial biosensor 310;

7. Detect the beneficial microorganism on the surface 3050 with the microbial biosensor;

8. Display the pathogen count, the pathogen type, the pathogen concentration, and the pathogen biosafety level on the microbiome mobile application 250;

9. Display the beneficial microorganism count, the beneficial microorganism type, and the beneficial microorganism concentration on the microbiome mobile application 250;

10. Sterilize the pathogen type found by pressing and holding the microbial biosensor power button 319; and 11. Power off the microbial biosensor 310 by pressing the microbial biosensor power button 319.

The exemplary microbial biosensor surface test method diagram 3010 shows detection of microorganisms 610 on a surface 3050 using infrared spectroscopy 2510 and particle imaging 2530 methods.

The example surface 3050 types illustrate the detection of microorganisms 610 on top of the drinks 3052, food 3054, furniture 3056, clothes 3058, dining table 3060, and skin infection 3062 surfaces.

The skin infection 3062 or wound infection can be cellulitis, erysipelas, impetigo, folliculitis, furuncles, and carbuncles. The most common pathogenic microorganisms 610 found by microbial biosensor 310 in wound infections are *Staphylococcus aureus*, Coagulase-negative staphylococci, Enterococci, and *Escherichia coli*. The microbial biosensor 310 also detects microorganisms 610, and particles such as small molecules, lipids, proteins in a user 3802 sample on top of a glass slide. The user 3802 sample can be blood, urine, tissue, serum, plasma, spinal fluid, cell free DNA, and so on smeared on top of the glass slide. In this case the microbiome mobile application 250 database 3856 contains the dataset and information about particles such as small molecules, lipids, proteins.

FIG. 31 is an example pollen grain diagram 3110, a pollen grain structure and components diagram 3150, a pollen structure components, function, and chemical composition list 3170, and a percent chemical composition of an air-dried pollen list 3190, according to some embodiments.

The pollen grain diagram 3110, and a pollen grain structure and components diagram 3150 show the various components and their shapes of an exemplary common ragweed pollen.

The pollen structure components, function, and chemical composition list 3170 describes the component name, its primary function, and predominant chemical composition.

The percent chemical composition of an air-dried pollen list 3190 describes primary constituents and corresponding percent of dry weight. The size of the same pollen is different with and without moisture. The pollen database 3450 has the information for the same pollen with moisture and air-dried. This allows detection of the pollen correctly.

The above structure, components, chemical composition information for each pollen grain 630 is used by the microbial biosensor 310 and particulate matter sensor 320 to detect it. Pollen grains 630 can be found on the surface of the object. The particle detection methods 2500 of particle imaging 2530, and light scattering and imaging 2570, are more suitable to detect pollen grains 630.

The existing methods of pollen grain collection and counting are cumbersome. The major types of sampling devices used for outdoor monitoring of airborne particles and aeroallergens are passive gravity slides, rotary impact, and slit suction type-volumetric spore traps. Many methods are utilized to count pollen. They fall into three major categories: counting with the human eye, electronic or laser-based particle counters, and image processing algorithms. The disadvantages are collection and counting using specialized collection devices and use of time-consuming instruments.

FIG. 32 illustrates pollen grain shapes diagram 3200, according to some embodiments.

The morphological characteristics of pollen grains are categorized into different groups such as pollen units, polarity, symmetry, shape, size, number of apertures and form, and exine stratification to allow for easy detection.

The pollen grain units can be as follows:

1. Monad 3210: The pollen grains do not remain united at maturity and are dissociated into a single pollen grain called a monad.

2. Dyad 3212: Pollen grains which are united in pairs and shed from the anthers as doubles are called dyads.

3. Tetrad 3214: Four pollen grains are united to form a tetrad. Tetrads are further categorized into different types based on their arrangement. In this case it is a Tetrahedral tetrad, where pollen grains are arranged in two different planes where three grains are in one plane, and one lies centrally over the other three, e.g., Drymis (Winteraceae), Drosera (Droseraceae), and *Rhododendron ericaceae*).

3a. Tetragonal tetrad 3214-1: All four pollen grains are arranged in one plane, e.g., *Typha latifolia* (Typhaceae) and *Hedycaria arborea* (Monimiaceae).

3b. Decussate tetrad 3124-2: Pairwise, the pollen grains are at right angles to each other, e.g., *Magnolia grandiflora* (Magnoliaceae).

3c. Rhombohedral tetrad 3214-3: All pollen grains are arranged in one plane forming a rhomboidal shape, e.g., *Annona muricata* (Annonaceae).

3d. T-shaped tetrad 3214-4: The first division of the pollen mother cell is transverse to form a dyad. The upper or lower cell of the dyad undergoes a vertical or longitudinal division instead of transverse, yielding either a straight or inverted T-shaped configuration, e.g., *Aristolochia* sp. (Aristolochiaceae), and *Polyanthes* sp. (Amaryllidaceae).

3e. Linear tetrad 3214-5: The first division of the pollen mother cell is transverse, and a dyad is formed. Each cell of the dyad again divides transversely to form a linear tetrad, e.g., *Mimosa pudica*.

3f. Crypto tetrad 3214-6: Tetrads are formed without partition walls between the four compartments. One out of the four nuclei develops normally and the other three obliterate, e.g., Cyperaceae.

4. Polyads 3216: Each of the tetrad cells divides once or twice or more, yielding a group of 8 to 64 cells which remain together after maturity. These compound grains are usually held together in small units and are called polyads, e.g., *Acacia auriculiformis, Adenanthera pavonina, Calliandra hematocephalla, Samania saman*, and *Albizzia lebbeck*.

5. Pollinia 3218: The whole contents of an anther or anther locule which shed as one united mass of pollen are called Pollinia, e.g., Calotropis sp., Daemia sp., etc., of the Asclepiadaceae and majority of the family Orchidaceae.

One of the other distinguishing characteristics of pollen grains is number of apertures. It can be single grains without apertures 3230, single grains with furrows 3240, or single grains with apertures 3250. There can be one to many apertures in case of single grains with apertures 3250.

The above pollen unit and number of apertures information is stored in the pollen database 3450 and allows for correct pollen detection.

FIG. 33 is an example pollen type source, name, disease, shape, and size list 3300, and a pollen attributes and biosensor detector list 3390, according to some embodiments.

The pollen type pollen type source, name, disease, shape, and size list 3300, and the pollen attributes and biosensor detector list 3390 are used by the microbial biosensor 310 and particulate matter sensor 320 to detect pollen. The pollen safety data sheet in FIG. 47 information is derived from this data.

FIG. 34 is an example pollen tree taxonomy 3410, pollen data 3430, and a pollen database 3450, according to some embodiments.

The pollen tree taxonomy 3410 allows for classifying new pollen trees or reclassifying existing ones.

Palynology is study of pollen grains and other spores, especially as found in archaeological or geological deposits. It can be used to reconstruct past vegetation (land plants) and marine and freshwater phytoplankton communities.

The pollen data 3430 consists of allergens of pollen, pollen allergy, pollen grain and associated allergies, pollen safety data sheet, attributes, and unique identifiers information.

The pollen database 3450 comprises Pollen Table 3452, Pollen Platform Dataset Table 3454, Pollen Tree Taxonomy, Pollen Allergy, Annotation, Pollen Safety Data Sheet Table 3456, and Pollen Attributes and Unique Identifiers 3458. The wearable device 100 uses the data in the pollen database 3450 to display pollen type and associated information.

FIGS. 35 and 36 illustrate how an example particulate matter sensor 320 operates, detects, measures, and monitors a set of suspended particles in the surrounding air near the user 3802.

FIG. 35 illustrates an example particulate matter sensor pinout 3510 and a particulate matter sensor wiring table 3550 describing the hardware wiring connection steps of a particulate matter sensor pinout 3510 connected to the single board computer 350 general purpose input output pinout 370 that can be utilized to implement various embodiments.

The particulate matter sensor 320 implements, operates, detects, measures, and monitors a set of suspended particles in the surrounding air per the following procedure:

1. Log in to the single board computer 350 operating software and access general purpose input output pinout 370 settings. Assign and map the general purpose input output pinout 370 to be connected to a particulate matter sensor pinout 3510. Save general purpose input output pinout 370 settings.

2. Connect the particulate matter sensor pinout 3510 to a single board computer 350 assigned general purpose input output pinout 370 as listed in the particulate matter sensor wiring table 3550. The hardware implementation of the particulate matter sensor 320 is complete after the particulate matter sensor pinout 3510 is connected to a single board computer 350 general purpose input output pinout 370.

3. Prepare the single board computer 350 operating software to communicate with the particulate matter sensor 320 by loading the general purpose input output pinout 370 software library and installing the particulate matter sensor 320 software driver.

4. Program, install, execute, and run the particulate matter sensor 320 software on the single board computer 350 operating software.

The particulate matter sensor 320 detects, measures, and monitors a set of suspended particles using light scattering and imaging 2570 method in the surrounding air and measurement comprising:

the pathogen count, the pathogen type, the pathogen concentration, and the pathogen biosafety level;

the beneficial microorganism count, the beneficial microorganism type, and the beneficial microorganism concentration;

a pollen type, a pollen count, and a pollen allergy level;

a dust mite allergen count, and dust mite allergy level;

a particulate matter concentration; and an air quality index.

FIG. 36 illustrates an example particulate matter sensor working principle block diagram 3610 and an air quality index level of concern table 3680 that can be utilized to implement various embodiments.

The particulate matter sensor 320 uses a light scattering and imaging 2570 detection method. The working principle functioning is as follows:

The intended use of the particulate matter sensor 320 is to detect, measure, and monitor the air quality index value surrounding the user 3802 and can be used to provide level of health concern information to the user 3802. The particulate matter sensor working principle block diagram 3610 uses a laser scattering principle which is part of sensing cavity 322. The laser scattering principle used for such sensor produces scattering by using a laser source 3612 to produce a laser beam 3614 to radiate suspending particles in the air 3616 entering through an air channel 3618, passing through the light scattering measuring cavity 3620, and then collecting scattering light in a certain degree, and finally obtaining the curve of scattering light change with time. The raw electric signal 3622 is amplified when it passes through a filter amplifier circuit 3624. In the end, the filtered electric signal 3626 is processed by an on-chip microprocessor 3628. Equivalent particle diameter and the number of particles with different diameters per unit volume can be calculated by the on-chip microprocessor 3628 based on the MIE theory of absorption and scattering of plane electromagnetic waves by uniform isotropic particles of the simplest form. MIE theory is an analytical solution of Maxwell's equations for the scattering of electromagnetic radiation by particles of any size. The output digital signal 3630 is the quality and number of each particle with different size per unit volume. The unit volume of the particle number is 0.1 L, and the unit of mass concentration is µg/m³. The sensing cavity 322 can detect picometer, nanometer, and micrometer particle size and ensures the differentiation and identification of the suspended particles in the air in terms of pathogens, beneficial microorganisms, pollen, dust mite allergen, dust, and so on.

The particulate matter sensor 320 sensing cavity 322 can detect and differentiate the microorganisms 610. The imaging system 3660 uses the microbial biosensor 310 hardware. The step of imaging uses particle imaging 2530 detection method principles. The imaging system 3660 consists of light scattering and imaging 2570 system components such as microbial biosensor 310 and picocamera 318. The imaging system 3660 is responsible for taking images and videos of the particles 3650 passing through the imaging cavity 3662 when they are in front of special darkfield photographic plate. The microorganisms 610 are classified based on cell structure, cell wall, or on differences in cell components such as DNA, RNA, fatty acids, pigments, antigens, and quinones, and classifies pollen grains 630 and dust mite allergens 640 using image analysis working principle 2660. This particulate matter sensor 320 detects the pathogen count, the pathogen type, the pathogen concentration, and the pathogen biosafety level. The particulate matter sensor 320 also detects, measures, and monitors the beneficial microorganisms count, beneficial microorganism type, and beneficial microorganism concentration in the surrounding air. The wearable device 100 is programmed and contains microorganism database 2120 which includes microorganisms' 610 unique identifiers associated with particulate matter sensor 320 particle detection methods 2500 of light scattering and imaging 2570.

An air quality index (AQI) is used by government agencies to communicate to the public how polluted the air currently is or how polluted it is forecast to become. Public health risks increase as the AQI rises. The air quality index level of concern table 2450 lists the AQI color, levels of concern, values of the index, and corresponding different level of health concern. The description of the air quality also provides information about what kind of personal protective equipment (PPE) is required while handling waste. The air quality index data obtained through the particulate matter sensor 320 can be further augmented by the Environmental Protection Agency AirNow Application Program Interface (API), which allows for access to real-time data and forecasts.

The neighborhood public biosafety alert can also be a text alert sent to a nearby user's 3802 microbiome mobile application 250 when the biosafety level, for instance, is equal to 3 and above, indicating that there is pathogenic air nearby which can result in disease outbreak. These pathogens may spread through a person, or the air breathed can be loaded with pathogens. The text alert can recommend user 3802 evacuate or stay indoors, and so on. Common pathogenic bacteria found in the air in and around the home are *Staphylococcus, Pseudomonas*, Parasitic *Bacillus*, and *Francisella tularensis*, a naturally occurring bacterium that causes tularemia, also known as rabbit fever, in harmful amounts. Many common viral infections can spread by airborne transmission at least in some cases, including but not limited to COVID-19, Measles Morbillivirus, Chickenpox Virus, *Mycobacterium Tuberculosis*, Influenza Virus, Enterovirus, and Norovirus. Airborne fungi are also responsible for many fungal infections in humans. Some of the infectious fungi are *Aspergillus fumigatus, Blastomyces dermatitidis, Cryptococcus neoformans, Histoplasma capsulatum*, and so on.

It is possible to integrate the neighborhood public biosafety alert and have a neighborhood public biosafety alert sent to mobile devices of all nearby residents in the form of public safety alerts to alert the nearby residents quickly and effectively to critical and serious emergencies.

The particulate matter sensor 320 data is displayed on the microbiome mobile application 250 as shown in the figures FIG. 39, FIG. 40, FIG. 41, and FIG. 42.

FIG. 37 is an example single board computer 350 and enviro sensor circuit block diagram 3710 and enviro sensor wiring table 3750, according to some embodiments.

The enviro sensor 330 implements, operates, detects, measures, and monitors and measures environmental conditions surrounding the user 3802 as per the following procedure:

1. Log in to the single board computer 350 operating software and access general purpose input output pinout 370 settings. Assign and map the general purpose input output pinout 370 to be connected to an enviro pinout cable 348. Save general purpose input output pinout 370 settings.

2. Connect the enviro pinout cable 348 to a single board computer 350 assigned general purpose input output pinout 370 as listed in the enviro sensor wiring table 3750. The hardware implementation of the enviro sensor 330 is complete after the enviro pinout cable 348 is connected to a single board computer 350 general purpose input output pinout 370.

3. Prepare the single board computer 350 operating software to communicate with the enviro sensor 330 by loading the general purpose input output pinout 370 software library and installing the enviro sensor 330 software driver.

4. Program, install, execute, and run the enviro sensor 330 software on the single board computer 350 operating software.

The enviro sensor 330 detects, monitors, and measures environmental conditions surrounding the user 3802, comprising:

The wearable device 100 enviro sensor 330 detects, monitors, and measures environmental conditions surrounding the user 3802, comprising:

an RFID tag sensor 332 to detect, measure, and monitor RFID tag digital data;

a location sensor 334 to detect, measure, and monitor a geospatial position and an altitude;

an ambient light sensor 336 to detect, measure, and monitor an ambient light level;

a gas sensor 338 to detect, measure, and monitor a gas type;

a smoke sensor 340 to detect, measure, and monitor a smoke level;

a temperature, humidity, and pressure sensor 342 to detect, measure, and monitor a temperature;

a temperature, humidity, and pressure sensor 342 to detect, measure, and monitor a humidity;

a temperature, humidity, and pressure sensor 342 to detect, measure, and monitor a pressure;

a sound sensor 344 to detect, measure, and monitor a sound level;

an ultraviolet light sensor 346 to detect, measure, and monitor an ultraviolet index;

The enviro sensor 330 data and particulate matter sensor 320 data are used to predict and forecast pathogen biosafety level risk, a pollen allergy level risk, a dust mite allergy level risk, an air quality index risk, a fire risk, a hearing loss risk, and an unprotected sun exposure risk.

The artificial intelligence algorithms are used to predict and forecast risks. The input data used is hourly, daily, monthly, and yearly microbial sensor 310, particulate matter sensor 320, and enviro sensor 330 data.

The wearable device 100 single board computer 350 comprises:

an accelerometer 356 sensor to detect, measure, and monitor a tilt position;

a gyroscope 358 sensor intended to detect an orientation;

The tilt position and the orientation enable the microbial biosensor 310 to face and align to the nasal cavity 2840, oral cavity 2890, or surface 3050.

The detailed implementation, operation, detection, measurement, and monitoring, and working principle for each of the sensors is as follows:

The RFID tag sensor 332 working principle functioning is as follows:

The intended use of the RFID tag sensor 332 is to detect and send an RFID tag digital data value of the wearable device 100. An RFID or radio frequency identification system consists of two main components, an RFID tag attached to an object to be identified, and a transceiver, also known as reader and writer. A reader and writer consist of a radio frequency module and an antenna which generates a high frequency electromagnetic field. On the other hand, the RFID tag is usually a passive device, meaning it does not contain a battery. Instead, it contains a microchip that stores and processes information, and an antenna to receive and transmit a signal. To read the information encoded on the RFID tag, it is placed near the reader and writer but does not need to be within direct line-of-sight of the reader and writer. A reader generates an electromagnetic field original radio signal which causes electrons to move through the RFID tag's antenna and subsequently power the chip. The powered chip inside the RFID tag then responds by sending its stored RFID tag digital data value information back to the reader and writer in the form of another reflected radio signal. This is called backscatter. The backscatter, or change in the electromagnetic radio frequency wave, is detected, and interpreted by the reader and writer, which then sends the RFID tag digital data value out to the microbiome mobile application 250 and cloud server 3850.

The RFID tag sensor 332 operation involves reading digital data of the wearable device 100 RFID tag. The wearable device 100 also contains Universal Device Identifier (UDI) information. The wearable device's 100 information is read by the reader and writer. The RFID tag digital data value is stored in the secure digital card 360 of the single board computer 350.

The ambient light sensor 336 working principle functioning is as follows:

The intended use of the ambient light sensor 336 is to detect, measure, and monitor ambient light surrounding the user 3802 to reduce power consumption and increase wearable device 100 battery life. Ambient light sensors are silicon monolithic circuits with an integrated light-sensitive semiconductor photodiode—a PN junction which converts light into an electrical signal. Light is necessary for the sense of sight. Light is a form of electromagnetic radiation. It carries energy in the form of small energy packets called photons. The energy in the photon is transferred to the objects when they come into contact with it. This characteristic of light is used in designing sensors that can detect light. These sensors, known as ambient light sensors, absorb the energy from light and change it into electricity with the help of the photoelectric effect. The electricity produced will be proportional to the intensity of light which falls on the sensor and sensor material.

Ambient light sensor ICs have an output current proportional to light (current sourcing) and can have a measurement range of 0 to ~65,535 lux. The ambient light sensor classification range is 0-100 (dark), 101-1,000 (dim), 1,001-10,000 (overcast), 10,001-25,000 (daylight), and 25,001-65,535 (sunlight).

The wearable device 100 is in an inactive energy saving mode if the ambient light level value 620 based on illuminance surrounding the user 3802 is dim or dark.

Ambient light sensor 336 information is used to conserve the battery during the night and/or other period of inactive use of the wearable device 100. For example, wearable device 100 sensor arrangements and the single board computer 350 can be set in a low-energy sleep mode during the night using the ambient light sensor 336.

The location sensor 334 GPS operating principle functioning is as follows:

The intended use of the location sensor 334 is to determine the geospatial location and altitude of the wearable device 100 and can provide internet access to the wearable device 100. The location sensor 334 consists of two components, a GPS receiver and cellular adapter.

The GPS receiver operating principle is based on the global positioning system. The global positioning system is a satellite navigation system that provides location and time information in all climate conditions to the user.

GPS consists of three segments, the GPS satellites space segment, control segment, and user segment.

The GPS space segment consists of at least 24 satellites circling the Earth every 12 hours at about 12,000 miles in altitude. The GPS space segment is formed by a satellite constellation with at least four simultaneous satellites in view from any point on the Earth's surface at any time.

The GPS control segment includes a master control station, an alternate master control station, 12 command and control antennas, and 16 monitor stations outfitted with atomic clocks that are spread around the globe to correct any abnormalities and send back to the GPS satellites through ground antennas.

The GPS user segment comprises the GPS receiver, which receives the signals from the GPS satellites and detects how far away they are from each satellite.

The temperature, humidity, and pressure sensor 342 operating principle functioning is as follows:

The temperature, humidity, and pressure sensor 342 consists of three components: a temperature sensing element, a humidity sensing element, and a pressure sensing element.

The intended use of the temperature sensor is to detect, measure, and monitor temperature value surrounding the user 3802. The temperature sensing element working principle is based on using a diode as a temperature sensor. The functioning consists of a constant current I being applied across the junction of the diode, and output voltage V is proportional to the temperature. The voltage V change across a diode or PN junction can be used with a lookup table or an equation to calculate a temperature for any given diode voltage. The MEMS semiconductor temperature sensors are based on these fundamental temperature and current characteristics of the bipolar transistor or diode. The sensor has high degree of linearity and simple calibration.

Microorganisms 610 can also be classified according to the range of temperature at which they can grow. The growth rates are the highest at the optimum growth temperature for the microorganism 610. The lowest temperature at which the organism can survive and replicate is its minimum growth temperature. The highest temperature at which growth can occur is its maximum growth temperature. High temperature can also result in deactivation of certain microorganisms 610. Temperature of 60 degree Celsius and above kills most of the microorganisms 610. Bacteria 616 thrive in the temperature range of 4 degrees Celsius to 20 degrees Celsius. Dust mites 622 thrive in temperatures of 20 to 25 degrees Celsius. The temperature of 54 degrees Celsius and above kills dust mites 622. Pollen size and shape is different based on the amount of moisture. Higher temperature results in dried pollen. Particulate matter sensor 320 uses this information to compare the pollen size based on temperature and amount of humidity in the air. The surrounding air temperature data is used by the microbial biosensor 310, and particulate matter sensor 320 to rule out sets of microorganisms 610 which might not exist based on their temperature profile, resulting in deactivating detection of certain microorganisms 610. Microbial biosensor 310 and particulate matter sensor 320 use microorganisms' 610 temperature profile attribute information to activate or deactivate certain particle detection methods 2500.

The intended use of the humidity sensor is to detect, measure, and monitor the humidity value surrounding the user 3802. The humidity sensing element working principle is based on using a differential capacitance as a humidity sensor. The MEMS humidity sensor is a differential capacitance type that consists of a humidity sensitive polymer layer sensitive to the water vapor that is sandwiched between two electrodes and that acts as capacitor plates. The upper water vapor permeability electrode consists of a grid that allows water vapor to pass into the humidity sensitive polymer layer below, which is a backplate electrode, thus altering the capacitance between the two electrodes. The capacitance of the humidity sensing element is proportional to humidity. Many microorganisms 610 require relative humidity (RH) of 60 percent or more, though some can survive and multiply in relative humidity of >20 percent. Thus, decreasing temperature and moisture (relative humidity), creates a less hospitable environment for microorganisms to grow. Viruses 614 and bacteria 616 die off faster in higher relative humidity. In the surrounding air when the humidity is high, the viral and bacterial particles decay faster, and less viral and bacterial material remains suspended in the air, leading to reduced risk of infection. Dust mites 622 like humidity levels of 70 to 80 percent. Dust mites 622 cannot live in environments where humidity levels are below 50%. Pollen moisture content is directly proportional to the humidity in the air. Decreasing temperature and moisture (relative humidity), create a less hospitable environment for microorganisms 610 to grow. Microbial biosensor 310 and particulate matter sensor 320 use microorganisms' 610 humidity profile attribute information to activate or deactivate certain particle detection methods 2500.

The pressure sensor use is to detect, measure, and monitor a pressure value surrounding the user 3802. The pressure sensing element working principle is based on using a change in capacitance as a pressure sensor. The MEMS technology allows a small and flexible structure in the form of a capacitive sensor. It contains an original diaphragm that is formed through one capacitive plate that is in contact with the atmosphere with respect to the reference backplate. The atmospheric pressure is detected through how much the original diaphragm is deformed due to resulting pressure. The higher the atmospheric pressure, the more the deformed diaphragm moves, which results in a higher barometer reading. The deformation of the diaphragm changes the spacing between the conductors and hence changes the capacitance. The deflection in the diaphragm due to change in pressure produces a change in capacitance. The capacitance change can be measured by including the sensor in a tuned circuit, which changes its frequency with changing pressure. Microorganisms 610 are killed by high hydrostatic pressure. This pressure-induced inactivation is strongly dependent on the amount of applied pressure, the temperature, and the medium. Microbial biosensor 310 and particulate matter sensor 320 use microorganisms' 610 pressure profile attribute information to activate or deactivate certain particle detection methods 2500.

The gas sensor 338 working principle functioning is as follows:

The intended use of the gas sensor 338 is to detect, measure, and monitor the gas type surrounding the user 3802. The basic principle behind metal oxide gas sensors is that the resistance of the detecting layer in the sensor changes in the presence of the target gases Reducing (RED), Oxidizing (OX), and Ammonia (NH3). The reducing and ammonia gases such as carbon monoxide or volatile organic compounds (VOC) remove some of the "insulative" oxygen species at the grain boundaries, thus causing the overall resistance to go down. Alternatively, oxidizing gases such as nitrogen dioxide add to the insulative oxygen species, causing the resistance to increase. The MEMS silicon metal oxide gas sensor is based on changes to the electrical resistance for different concentrations of varied gases.

The change in resistance is directly proportional to analog voltage. The analog voltage readings that the sensor produces are read by an analog to digital converter (ADC) and then converted into resistances.

The value of Ro is the value of resistance in clean air (or the air being compared), and the value of Rs is the value of resistance of the sensor exposed to gases. The sensor should be calibrated first by finding the value of Ro in fresh air and then using that value to find Rs using the mathematical formula:

$$\text{Resistance of sensor } (Rs) = (Vcc/VRL - 1) \times RL$$

Where Vcc is the positive power supply, VRL is the output voltage of RED OUT, OX OUT, and NH3 OUT corresponding to RL variable resistance R1, R2, and R3, respectively.

Once Rs and Ro are calculated, the ratio is determined, and then using the RED sensor graph, OX sensor graph, and NH3 sensor graph, the equivalent value of parts per million (PPM) for RED, OX, and NH3 gas is calculated.

The detected gases are comprised as follows:

A reducing gas, wherein the reducing gas comprises: a carbon monoxide, an ammonia, an ethanol, a hydrogen, a methane, a propane, and an isobutane.

An oxidizing gas, wherein the oxidizing gas comprises: a nitrogen dioxide, a nitrogen oxide, and a hydrogen.

An ammonia, wherein the ammonia comprises: a hydrogen, an ethanol, an ammonia, a propane, and an isobutane.

Microbial biosensor 310 and particulate matter sensor 320 use microorganisms' 610 gas profile attribute information to activate or deactivate certain particle detection methods 2500.

The smoke sensor 340 working principle functioning is as follows:

The intended use of the smoke sensor 340 is to detect, measure, and monitor smoke surrounding the user 3802. The output voltage changes provided by the sensor changes in proportion to the concentration of smoke. The greater the smoke concentration, the higher is the output voltage, while lesser smoke concentration results in low output voltage. The smoke concentration parts per million (PPM) can be determined using the Rs/Ro V/S PPM smoke sensor graph. The value of Ro is the value of resistance in fresh or clean air (or the air which is being compared), and the value of Rs is the value of resistance of the sensor exposed to gases. The sensor should be calibrated by finding the value of Ro in clean air and then using that value to find Rs using the mathematical formula:

Resistance of sensor $(Rs)=(Vcc/VRL-1) \times RL$

Where Vcc is the positive power supply, VRL is the output voltage, and RL is variable resistance.

Once Rs and Ro are calculated, the ratio Rs/Ro can be determined, and using the smoke sensor graph, the corresponding equivalent value of PPM for the smoke can be calculated.

Smoke contributes to modifications of the nasal, oral, lung, and gut microbiome, leading to various diseases, such as periodontitis, asthma, chronic obstructive pulmonary disease, Crohn's disease, ulcerative colitis, and cancers. Smoke kills off the beneficial bacteria in the mouth, allowing disease-causing bacteria to flourish, resulting in a greater risk for both gum disease and tooth decay. Microbial biosensor 310 and particulate matter sensor 320 use microorganisms' 610 smoke profile attribute information to activate or deactivate certain particle detection methods 2500.

The sound sensor 344 working principle functioning is as follows:

A sound sensor is defined as a module that detects sound waves through its intensity and converts them to electrical signals. A sound sensor can be used to receive acoustic waves and display the vibration image of sound. The microphone is sensitive to sound. The microphone vibrates with the acoustic wave, resulting in the change of capacitance and the subsequent micro voltage. It responds to sound loudness the same way the human ear does. It can measure sound level along a range from 45 to 110 dB. It is ideal for measuring environmental noises and room acoustics near the user. Some audible sound frequencies, and high-power ultrasound, cause cell disruption, and particle size reduction kills microorganisms 610. The microbial biosensor 310 and particulate matter sensor 320 use microorganisms' 610 audible sound profile attribute information to activate or deactivate certain particle detection methods 2500.

The ultraviolet light sensor 346 working principle functioning is as follows:

UV radiation is present in sunlight, and constitutes about 10% of the total electromagnetic radiation output from the sun. The UV region covers the wavelength range 100-400 nm and is divided into three bands: UV-A (315-400 nm), UV-B (280-315 nm), and UV-C (100-280 nm). The ultraviolet light sensor 346 outputs an analog voltage that is directly proportional to UV radiation incident on a planar surface. Not all ultraviolet light spectra kill microorganisms 610. UV-C, also known as germicidal UV, of wavelengths from 200 to 280 nm, is used to disinfect water, air, and surfaces 3050. UV-C is effective at destroying and deactivating all kinds of pathogens like viruses 614, bacteria 614, and fungus 616. Microbial biosensor 310 and particulate matter sensor 320 use microorganisms 610 ultraviolet profile attribute information to activate or deactivate certain particle detection methods 2500.

The accelerometer 356 sensor working principle functioning is as follows:

The intended use of the accelerometer 356 sensor is to measure the movement of the wearable device 100 when the wearable device 100 is moved, and can be used to set the waste fill level status to zero.

The wearable device 100 accelerometer 356 sensor measures the movement of the wearable device 100, and when the wearable device 100 is faced in front of nasal cavity 2840, oral cavity 2890, or surface 3050, the inclination angle can be used to center it and check for nose ID, face ID and surface ID.

An example schematic representation of a single board computer 350 containing hardware, peripheral interfaces, and general purpose input output pinout 370 layouts can be utilized to connect to sensors and power supply unit 380.

The example wearable device 100 single board computer 350 computing system can be configured to perform any one of the processes provided herein. In this context, the wearable device 100 single board computer 350 or SBC 350 may include, for example, a system on chip (SOC) 352 consisting of a central processing unit (CPU)/graphical processing unit (GPU), a random-access memory (RAM) 354, an accelerometer 356 sensor, a gyroscope 358, a secure digital card 360, a display DSI port 362, a Wi-Fi Bluetooth 364, a microphone and speaker 366, and a camera CSI port 368. It can also contain a universal serial bus, an audio port, and a high-definition multimedia interface. It contains a general purpose input output pinout 370 or GPIO pinout 370. The system on chip (SOC) 352, random access memory (RAM) 354, and secure digital card 360 are used to implement various microbial biosensor 310, particulate matter sensor 320, and enviro sensor 330 algorithms and methods and store data locally. General purpose input output pinout 370 or GPIO pinout 370 and other ports are used to connect to the microbial biosensor 310, particulate matter sensor 320, enviro sensor 330, power supply unit 380, and display unit 102. The display DSI port 362 can be used to connect a capacitive touchscreen to the wearable device 100 to display all the sensor data, which is usually in the form of connectors or ribbon cables. The camera CSI port 368 is used to connect to a picocamera 318 and screen for testing of the wearable device 100. The wearable device 100 single board computer 350 may include circuitry or other specialized hardware for carrying out some or all aspects of the processes. In some operational settings, a wearable device 100 single board computer 350 may be configured as a system that includes one or more subcomponents, each of which is configured to carry out some aspects of the processes either in software, hardware, or some combination thereof.

The wearable device 100 single board computer 350 can communicate with other computing devices based on various computer communication protocols such a Wi-Fi, a Bluetooth (and/or other standards for exchanging data over short distances including those using short-wavelength radio transmissions), a USB, an ethernet, a cellular network, an ultrasonic local area communication protocol, and so on.

Figure 38:
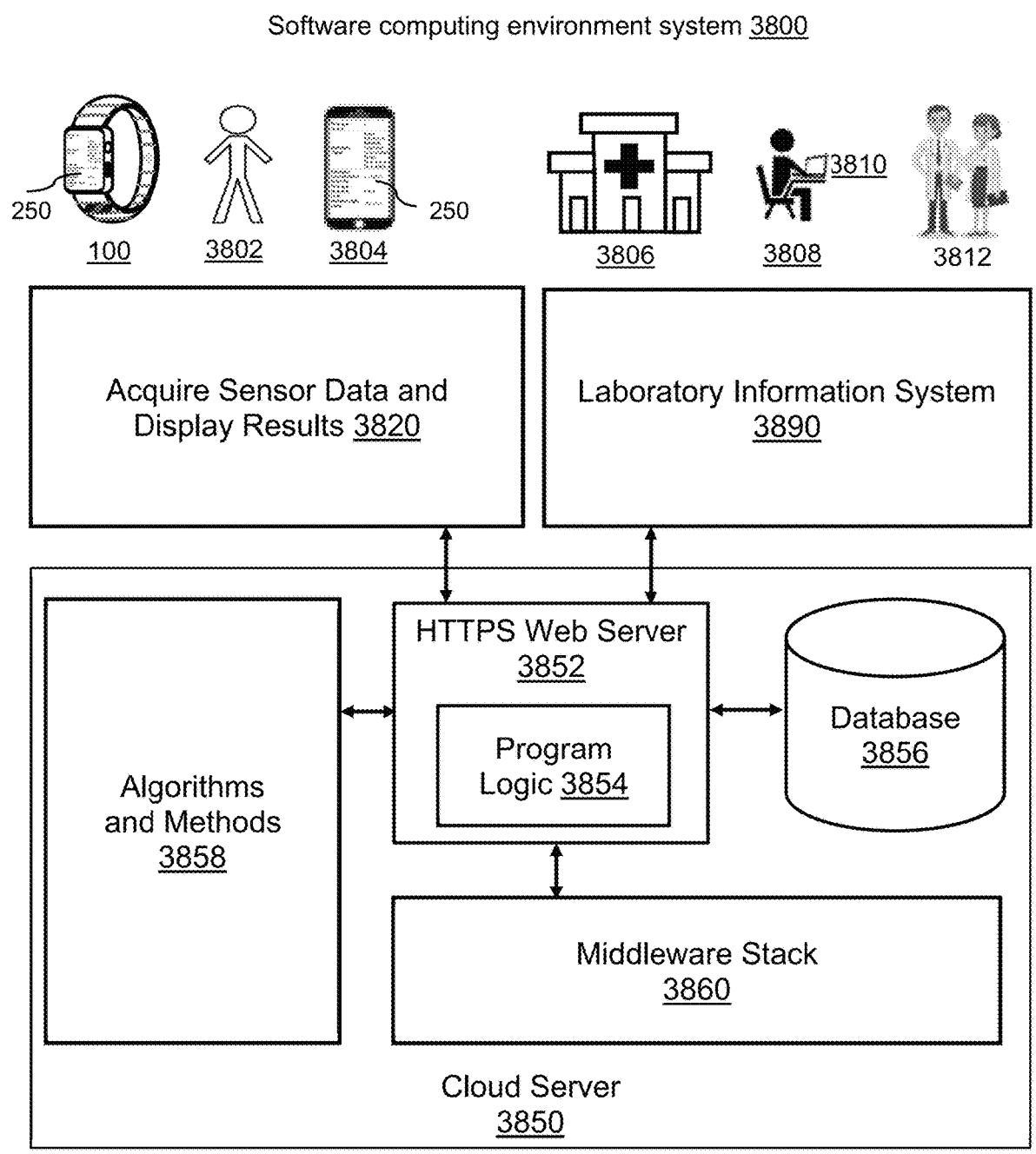
FIG. 38 illustrates an example software computing environment system that can be utilized to implement various embodiments.

FIG. 38 illustrates an example software computing environment system 3800, which can be utilized to implement various embodiments.

The software computing environment system 3800 comprises:

A wearable device 100 consisting of a smart band 200 and a display unit 102;

The smart band 200 comprises a microbial biosensor 310, a particulate matter sensor 320, an enviro sensor 330, a single board computer 350, a power supply unit 380, a band fastener 202, and a set of watch adapters 204 and 206. The watch adapters 204 and 206 allow smart band 200 to be connected to any watch. The set of clip adapters 208 and 210 allow it to be attached to a necklace 4810, waistband 4820, belt 4830, headband 4840, and so on;

The display unit 102 comprises a touchscreen 104, a display unit power button 106, a crown 108, and a set of attachment slots 110 and 112;

The microbial biosensor 310 comprises a transmitter 312, a receiver 314, a sterilizer 316, a picocamera 318, and a microbial biosensor power button 319;

The particulate matter sensor 320 comprises a sensing cavity 322;

The enviro sensor 330 comprises a set of sensors 332-346;

The power supply unit 380 comprises a wireless charging unit 382, a battery 384, a charging port 386, and a band power button 388;

A microbiome mobile application 250 allows a user to access the wearable and sensor data;

A user 3802;
A mobile device 3804;
A cloud server 3850;
A laboratory testing facility 3806;
A laboratory director 3808;
A laboratory computer 3810;
A laboratory information system 3890; and
A physician 3812.

The smart band 200 sends and receives signals through a wireless network to the microbiome mobile application 250 installed on the mobile device 3804, and to the cloud server 3850.

The processing step acquire sensor data and display results 3820 is responsible for collecting and sending the wearable device 100 data to the cloud server 3850. The data is also locally stored in the secure digital card 360 for standalone processing of the data. The data collected is from microbial biosensor 310, particulate matter sensor 320, and enviro sensor 330. The wearable device 100 sensor data values results can be displayed on the microbiome mobile application 250.

The processing step HTTPS web server 3852 is used for secure communication over a computer network between a client and server. The program logic 3854 performs decision making based on sensor data and allows branching to different parts of the microbiome mobile application 250 and laboratory information system 3890. The program logic 3854 is responsible for sending the information about methods to be executed to algorithms and methods 3858 based on the user 3802 request. The middleware stack 3860 acts as a bridge between the operating system, database 3856, and the application software like the microbiome mobile application 250 and laboratory information system 3890 to display the data rapidly. The database 3856 contains microorganism database 2120, pollen database 3450, wearable device 100 data, user 3802 data, and so on.

In processing step algorithms and methods 3858, the sensor data is processed through the system cloud server 3850 and sent to the database 3856 system to be stored. The algorithms and methods 3858 are responsible for following activities:

1. Perform the wearable device 100 microbial biosensor 310 data, particulate matter sensor 320 data, and enviro sensor 330 data analysis and evaluation using particle detection methods 2500, particulate matter sensor 320 methods, and enviro sensor 330 methods.

2. Display the microbial biosensor 310, particulate matter sensor 320, and enviro sensor 330 results on microbiome mobile application 250.

3. Create the wearable device 100 enviro sensor 330 data and particulate matter sensor 320 data clusters to predict a pathogen biosafety level risk, a pollen allergy level risk, a dust mite allergy level risk, an air quality index risk, a fire risk, a hearing loss risk, and an unprotected sun exposure risk.

4. Make real-time updates to the wearable device 100 data.

In processing step laboratory information system 3890 in the laboratory testing facility 3806, a laboratory director 3808 using a laboratory computer 3810 is responsible for the review and routing the user 3802 results to the physician 3812.

The software computing environment system 3800 wearable device 100 sends the microbial biosensor 310 data, the particulate matter sensor 320 data, and the enviro sensor data 330 to the cloud sever. The laboratory director 3808 reviews the data and determines the cause of disorders and reports out a user 3802 test results. The physician 3812 reviews user 3802 test results in conjunction with physiological data and determines the root cause of the disorder to treat the user 3802.

Microorganisms 610, pollen grains 630, and dust mite allergens 640 can all cause sinusitis and lung disorders. The microbial biosensor 310 data, the particulate matter sensor 320 data, and the enviro sensor data 330 user 3802 test results allow for accurate determination of nasal and lung related disorders. The precise root cause allows the physician to provide the right treatment to the user 3802.

The microbiome mobile application 250 comprises a set of functionalities to set up, control, and display data results of the wearable device 100. The setup functionality allows microbiome mobile application 250 to send and receive the data from wearable device 100. The control functionality allows setting sensor settings. The configurable display data results functionality allows the user 3802 to change the look and feel of the results displayed on the microbiome mobile application 250.

A laboratory information system 3890 comprises a set of functionalities to monitor user 3802 test results, microbial biosensor 310 results, particulate matter sensor 320 results, and enviro sensor 330 data results. The wearable device 100 real time data view allows laboratory director 3808 and physician 3812 to take appropriate measures in case of critical value results wherein the variance with normal is life-threatening if therapy is not instituted immediately.

The cloud server 3850 comprises a cloud sever memory, wherein the cloud server memory comprises a wearable device 100 model, wherein the wearable device 100 model comprises a set of wearable device attributes. The set of wearable device attributes comprises a wearable device unique device identifier (UDI), a name, an RFID tag, a geospatial position, an altitude, an ambient light level, a gas type, a smoke level, a temperature, a humidity, a pressure, a sound level, an ultraviolet light index, an air quality index, and so on.

Figure 39:
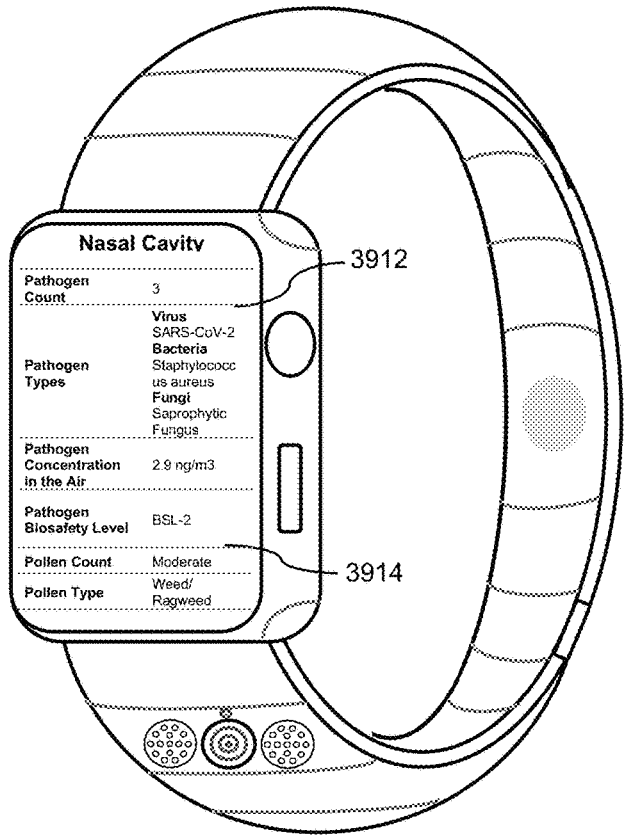
FIG. 39 illustrates a microbiome mobile application displaying nasal cavity pathogenic microorganism results, and a microbiome mobile application displaying oral cavity pathogenic microorganism results, according to some embodiments.

FIG. 39 illustrates a microbiome mobile application displaying nasal cavity pathogenic microorganisms' results 3910, and a microbiome mobile application displaying oral cavity pathogenic microorganisms' results 3950, according to some embodiments.

The example microbiome mobile application displaying nasal cavity pathogenic microorganisms' results 3910 element 3912 displays pathogen types of Virus SARS-CoV-2, Bacteria *Staphylococcus aureus*, and Fungi Saprophytic Fungus, and element 3914 displays a pathogen biosafety level of BSL-2.

The example microbiome mobile application displaying oral cavity pathogenic microorganisms' results 3950 element 3952 displays pathogen types of Virus SARS-Cov-2, Bacteria *Legionella pneumophila*, and Fungi *Candida albicans*, and element 3954 displays a pathogen biosafety level of BSL-2.

The microbiome mobile application 250 displays microbial biosensor 310, particulate matter sensor 320, and enviro sensor 330 data results per the user 3802 configured look and feel.

Figure 40:
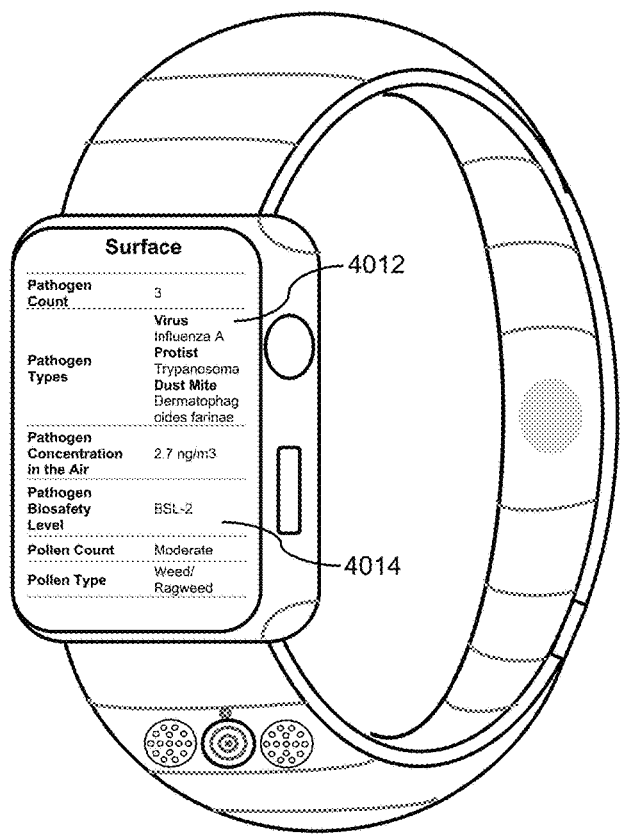
FIG. 40 illustrates a microbiome mobile application displaying surface object pathogenic microorganism results, and a microbiome mobile application displaying surrounding environment pathogenic microorganism results, according to some embodiments.

FIG. 40 illustrates a microbiome mobile application displaying surface object pathogenic microorganisms' results 4010, and a microbiome mobile application displaying surrounding environment pathogenic microorganisms' results 4050, according to some embodiments.

The example microbiome mobile application displaying surface object pathogenic microorganisms' results 4010 element 4012 displays pathogen types of Virus Influenza A, Protist *Trypanosoma*, and Dust Mite *Dermatophagoides farina*, and element 4014 displays a pathogen biosafety level of BSL-2.

The example microbiome mobile application displaying surrounding environment pathogenic microorganisms' results 4050 element 4052 displays pathogen types of Virus Influenza A, Bacteria *Staphylococcus*, Fungi Aspergillosis, and Protist *Trypanosoma*, and element 4054 displays a pathogen biosafety level of BSL-2.

The microbiome mobile application 250 displays microbial biosensor 310, particulate matter sensor 320, and enviro sensor 330 data results per the user 3802 configured look and feel.

FIG. 41 illustrates a microbiome mobile application displaying nasal cavity beneficial microorganisms' results 4110, and a microbiome mobile application displaying oral cavity beneficial microorganisms' results 4150, according to some embodiments.

The example microbiome mobile application displaying nasal cavity beneficial microorganisms' results 4110 element 4112 displays Beneficial Microorganism Types of Virus Bacteriophages, and Bacteria *Lactobacillus*, and element 4114 displays enviro sensor 330 data.

The example microbiome mobile application displaying oral cavity beneficial microorganisms' results 4150 element 4152 displays Beneficial Microorganism Types Bacteria *Streptococcus salivarius*, and element 4154 displays enviro sensor 330 data.

The microbiome mobile application 250 displays microbial biosensor 310, particulate matter sensor 320, and enviro sensor 330 data results per the user 3802 configured look and feel.

Figure 42:
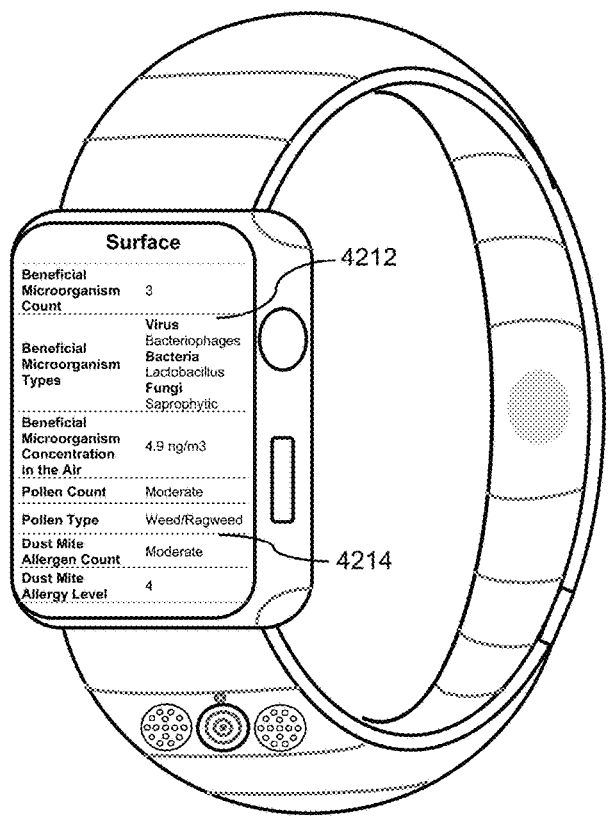
FIG. 42 illustrates a microbiome mobile application displaying surface object beneficial microorganism results, and a microbiome mobile application displaying surrounding environment pathogenic and beneficial microorganism results, according to some embodiments.

FIG. 42 illustrates a microbiome mobile application displaying surface object beneficial microorganisms' results 4210, and a microbiome mobile application displaying surrounding environment pathogenic and beneficial microorganisms' results 4250, according to some embodiments.

The microbiome mobile application displaying surface object beneficial microorganisms' results 4210 element 4212 displays Beneficial Microorganism Types of Virus Bacteriophages, Bacteria *Lactobacillus*, and Fungi Saprophytic, and element 4214 displays enviro sensor 330 data.

The microbiome mobile application displaying surrounding environment pathogenic and beneficial microorganisms' results 4250 element 4252 displays Pathogen Types of Virus Influenza A, Bacteria *Staphylococcus*, and Fungi Aspergillosis, and element 4254 displays Beneficial Microorganism Types of *Micrococcus*.

The microbiome mobile application 250 displays microbial biosensor 310, particulate matter sensor 320, and enviro sensor 330 data results per the user 3802 configured look and feel.

The functionality of the microbiome mobile application 250 installed on the native wearable device 100 or smartwatch or mobile device 3804 is the same.

The wearable device 100 microbiome mobile application 250 installed on the single board computer 350 secure digital card 260 displays the microbial biosensor 310 data, the particulate matter sensor 320 data, and the enviro sensor 330 data on the touchscreen 104.

The display unit 102 is powered to an on-state or to an off-state by pressing the display unit power button 106. The data displayed on the touchscreen 104 is scrolled by rotating the crown or can be scrolled by moving the finger up or down on the touchscreen 104. There is an audio alert when the crown 108 is pressed. The audio alert can be used in case user 3802 needs some help. Selecting the pathogen type virus influenza A 4052 displays a pathogen safety data sheet of FIGS. 44, 45, and 46. Selecting the pollen type ragweed displays a pollen safety data sheet of FIG. 47.

The wearable device 100 microbiome mobile application 250 is enabled to be installed on a smartwatch, or a mobile device 3804.

The smart band 200 in this case sends and receives signals through a wireless network to the microbiome mobile application 250 installed on the smartwatch, or the mobile device 3804.

The wearable device 100 display unit 102 is removed from the smart band 200 by sliding the set of watch adapters 204 and 206 from the set of attachment slots 110 and 112, and the smartwatch is connected to the set of watch adapters 204 and 206.

The smart band 200 sends and receives signals through the wireless network to the microbiome mobile application 250 installed on smartwatch. In this case the smartwatch displays the microbial biosensor 310 data, the particulate matter sensor 320 data, and the enviro sensor 330 data.

FIG. 43 illustrates an example pathogen biosafety alert 4310, a pollen allergy alert 4320, a dust mite allergy alert 4330, and an air quality alert 4340, according to some embodiments.

The wearable device 100 alerts 4300 comprise:

a pathogen biosafety alert 4310 is sent to the microbiome mobile application 250 of the user 3802 when the pathogen biosafety level is above a predetermined threshold level in the nasal cavity 2840, oral cavity 2890, surface 3050, or in the air surrounding the user 3802;

a pollen allergy alert 4320 is sent to the microbiome mobile application 250 of the user 3802 when the pollen allergy level is above a predetermined threshold level in the air surrounding the user 3802;

a dust mite allergy alert 4330 is sent to the microbiome mobile application 250 of the user 3802 when the dust might allergen level is above a predetermined threshold level in the air surrounding the user 3802;

an air quality alert 4340 is sent to the microbiome mobile application 250 of the user 3802 when the air quality level is above a predetermined threshold level in the air surrounding the user 3802; and wherein the smart band 200 sends and receives signals through the wireless network to the microbiome mobile application 250.

The wearable device 100 sends a pathogen biosafety alert 4310 to the microbiome mobile application 250 installed on the mobile device of the user 3802, and the physician 3812, when the pathogen biosafety level is above a predetermined threshold level in a nasal cavity 2840, an oral cavity 2890, on a surface 3050, or in the air surrounding the user 3802.

FIGS. 44, 45, and 46 illustrate an example pathogen safety data sheet.

FIG. 44 is an example page 1 of a pathogen safety data sheet. The microbiome mobile application 250 displays the pathogen type and data. In the example use case, Influenza virus type A was detected in the nasal cavity 2840, oral cavity 2890, on a surface 3050, or in the air, and displayed. Selecting the pathogen type Influenza virus type A hyperlink page 1 in the microbiome mobile application 250 displays the pathogen safety data sheet for Influenza virus type A. It contains information like infectious agent, hazard identification, and dissemination. This information enables the user 3802 to take appropriate actions in case they have the Influenza virus type A flu.

FIG. 45 is an example page 2 of a pathogen safety data sheet. The microbiome mobile application 250 displays the pathogen type and data. In the example use case, Influenza virus type A was detected in the nasal cavity 2840, oral cavity 2890, on a surface 3050, or in the air, and displayed. Selecting the pathogen type Influenza virus type A page 2 hyperlink in the microbiome mobile application 250 displays the pathogen safety data sheet for Influenza virus type A. It contains information like stability and viability, first aid/medical, and laboratory hazards. This information enables the user 3802 to take appropriate actions in case they have the Influenza virus type A flu.

FIG. 46 is an example page 3 of a pathogen safety data sheet. The microbiome mobile application 250 displays the pathogen type and data. In the example use case, Influenza virus type A was detected in the nasal cavity 2840, oral cavity 2890, on a surface 3050, or in the air and displayed. Selecting the pathogen type Influenza virus type A page 3 hyperlink in the microbiome mobile application 250 displays the pathogen safety data sheet for Influenza virus type A. It contains information like exposure controls/personal protection, handling and storage, and regulatory and other information. This information enables the user 3802 to take appropriate actions in case they have the Influenza virus type A flu.

FIG. 47 is an example page 1 of a pollen safety data sheet. The microbiome mobile application 250 displays the pollen type and data. In the example use case, ragweed pollen was detected in the air and displayed. Selecting the pollen type ragweed hyperlink in the microbiome mobile application 250 displays the pollen safety data sheet for ragweed. It contains information like pollen type, allergy identification, diagnosis, first aid/medical, and regulatory. This information enables the user 3802 to take appropriate actions in case they have the ragweed allergy.

The microbiome mobile application 250 can also display an entire pathogen safety data sheet. In this case, the user must scroll down to view the entire information.

FIG. 48 is an example smart band 200 attached to a necklace 4810, waistband 4820, belt 4830, and headband 4840.

The wearable device 100 display unit 102 is removed from the smart band 200 by sliding the set of watch adapters 204 and 206 from the set of attachment slots 110 and 112.

The smart band 200 is attached on a necklace 4810, a waistband 4820, a belt 4830, or a headband 4840 through a set of watch adapters 204 and 206 or clip adapters 208 and 210, or Velcro or any other element that would hold the smart band 200 for discreet sensing. The smart band 200 can also be attached to a cloth worn by the user 3802. The smart band 200 can also be worn on the ankle of the user 3802. The smart band 200 can be configured and attached to a stick, or a wand, or a cap for discreet sensing. The wearable device 100 or a smart band 200 can be configured and attached to a stick, or a wand to be used as a handheld device for real time testing of a nasopharyngeal cavity 2840, or an oral cavity 2890, or a surface 3050 of a person for presence of pathogens before entering the facility.

The attached smart band 200 sends and receives signals through the wireless network to the microbiome mobile application 250 and cloud server 3850.

CONCLUSION

A wearable device consists of a smart band, and a display unit. The smart band comprises a microbial biosensor, a particulate matter sensor, an enviro sensor, a single board computer, a power supply unit, a band fastener, and a set of watch adapters. The microbial biosensor detects, measures, and monitors beneficial microorganisms and pathogens in a nasal cavity, an oral cavity, or on a surface. The microbial biosensor sterilizer kills pathogens. The particulate matter sensor detects, measures, and monitors a set of suspended particles in the surrounding air comprising beneficial microorganisms, pathogens, pollen grains, dust mite allergens, and an air quality index. The pathogen results comprise a pathogen count, a pathogen type, a pathogen concentration, and a pathogen biosafety level. The enviro sensor detects, monitors, and measures environmental conditions surrounding the user. A computing system comprises a wearable device, a microbiome mobile application, a user, a mobile device, a cloud server, a laboratory testing facility, a laboratory information system, a laboratory director, and a physician. The smart band sends and receives signals through a wireless network to the microbiome mobile application installed on the mobile device, and to the cloud server. The wearable device eliminates sample collection, transportation, laboratory testing, reporting of results, and associated biohazardous waste. The analytical and clinical performance of the wearable device is very high because of confirmation of results by multiple particle detection methods.

The COVID-19 pandemic and local, state, and governmental policies to contain the spread of the virus have generated an enormous amount of biohazardous waste or healthcare waste. The healthcare waste composition is greatly influenced by disposable plastic-based personal protective equipment (PPE), COVID-19 test kits, hand sanitizer containers, and single-use plastics. The use of PPE, COVID-19 test kits, hand sanitizer containers, and single-use plastics during the pandemic not only increases the quantity of medical waste but also alters the average density of the medical waste. The current rapid surge in healthcare waste due to the COVID-19 pandemic is further exacerbating the problem, and there is an immediate threat that the impacts of unsafe disposal of healthcare waste will spill over into a crisis of environmental pollution. Unsafe disposal of healthcare waste not only pollutes the environment but also is conducive to the spread of infectious diseases such as COVID-19, hepatitis, HIV/AIDS, cholera, typhoid, and respiratory complications. The present invention reduces the environmental pollution and spread of infectious diseases by sterilizing the waste in the wearable device using a sterilizer to kill pathogens.

Although the present embodiments have been described about specific example embodiments, different modifications can be made to these without changing or taking away from the broader objective of the design. For example, additional sensors, devices, modules, microorganism detection methods, or alterations in the software can be operated to improve the system.

In addition, it can be appreciated that the various operations, processes, and methods disclosed herein can be embodied in a machine readable medium and/or a machine accessible medium compatible with a data processing system and can be performed in any order. Accordingly, the specifications and drawings are to be regarded in an illustrative rather than a restrictive sense. In some embodiments, the machine-readable medium can be a non-transitory form of machine-readable medium.

What is claimed as new and desired to be protected by Letters Patent of the United States is:

1. A wearable device comprising:
    a smart band, wherein the smart band comprises a microbial biosensor, a particulate matter sensor, an enviro sensor, a single board computer, a power supply unit, a band fastener, and a set of watch adapters;
    a display unit, wherein the display unit comprises a touchscreen, a display unit power button, a crown, and a set of attachment slots;
    wherein the microbial biosensor comprises a transmitter, a receiver, a sterilizer, a picocamera, and a microbial biosensor power button;
        wherein the microbial biosensor is configured to detects, measures, and monitors a pathogen count, a pathogen type, a pathogen concentration, and a pathogen biosafety level in a nasal cavity, an oral cavity, or on a surface;
        wherein the microbial biosensor is configured to detects, measures, and monitors a beneficial microorganism count, a beneficial microorganism type, and a beneficial microorganism concentration in the nasal cavity, the oral cavity, or on the surface;
        wherein the sterilizer is configured to kill the pathogen type;
    wherein the particulate matter sensor comprises a sensing cavity;
        wherein the sensing cavity is configured to detects suspended particles of picometer, nanometer, and micrometer sizes and is configured to differentiate and identify the suspended particles in the air;
    wherein the enviro sensor comprises a set of sensors;
    wherein the power supply unit comprises a wireless charging unit, a battery, a charging port, and a band power button; and
    a microbiome mobile application.

2. The wearable device of claim 1, wherein the particulate matter sensor is configured to detects, measures, and monitors a set of suspended particles in the surrounding air, wherein the set of suspended particles in the surrounding air detected and measurement output comprises:
    a pathogen count, a pathogen type, a pathogen concentration, and a pathogen biosafety level;
    a beneficial microorganism count, a beneficial microorganism type, and a beneficial microorganism concentration;
    a pollen type, a pollen count, and a pollen allergy level;
    a dust mite allergen count, and a dust mite allergy level;
    a particulate matter concentration;
    an air quality index;
    wherein a neighborhood public biosafety alert is sent to the wearable device when the pathogen biosafety level is above a predetermined threshold level, indicating that there is a pathogen in the surrounding air which can result in disease outbreak; and
    wherein the neighborhood public biosafety alert is configured to output a corrective and a preventive measure to reduce exposure to the pathogen.

3. The wearable device of claim 2, wherein the enviro sensor is configured to detect, monitor, and measure surrounding environmental conditions comprising:
    an RFID tag sensor configured to detect, measure, and monitor an RFID tag digital data;
    a location sensor configured to detect, measure, and monitor a geospatial position and an altitude;
    an ambient light sensor configured to detect, measure, and monitor an ambient light level;
    a gas sensor configured to detect, measure, and monitor a gas type;
    a smoke sensor configured to detect, measure, and monitor a smoke level;
    a temperature, humidity, and pressure sensor configured to detect, measure, and monitor a temperature, a humidity, and a pressure;
    a sound sensor configured to detect, measure, and monitor a sound level;
    an ultraviolet sensor configured to detect, measure, and monitor an ultraviolet index,
    wherein the enviro sensor data and particulate matter sensor data are configured to predict a pathogen biosafety level risk, a pollen allergy level risk, a dust mite allergy level risk, an air quality index risk, a fire risk, a hearing loss risk, and an unprotected sun exposure risk;
    wherein the pathogen biosafety level risk is configured to output a sterilization and a containment action based on four biosafety levels to reduce exposure to the pathogen; and
    wherein the pathogen biosafety level risk, the pollen allergy level risk, the dust mite allergy level risk, the air quality index risk, the fire risk, the hearing loss risk, and the unprotected sun exposure risk are configured to output a corrective and a protective action to prevent exposure to an unhealthy environmental condition.

4. The wearable device of claim 3, wherein the single board computer comprises:
    an accelerometer sensor configured to detect, measure, and monitor a tilt position;
    a gyroscope sensor configured to detect an orientation,
    wherein the tilt position and the orientation enable the microbial biosensor to face and align to the nasal cavity, oral cavity, or surface;
    wherein the accelerometer sensor is configured for centering the wearable device for a nasal ID, an open mouth ID, and a surface ID recognition;
    wherein the gyroscope sensor is configured for maintaining an orientation and an angular velocity of the wearable device; and wherein the orientation enables centering of the wearable device to the nasal cavity, the oral cavity, or the surface;
    wherein the microbial biosensor is configured to detects the pathogen and the beneficial microorganism in the nasal cavity, the oral cavity, or the surface; and
    wherein the sterilizer is configured to kill the pathogen in the nasal cavity, the oral cavity, or on the surface.

5. The wearable device of claim 4, wherein the microbiome mobile application installed on the single board computer displays the microbial biosensor data, the particulate matter sensor data, and the enviro sensor data on the touchscreen;
- wherein the display unit is powered to an on-state or to an off-state by pressing the display unit power button;
- wherein the data displayed on the touchscreen is scrolled by rotating the crown;
- wherein selecting the pathogen type displays a pathogen safety data sheet;
- wherein selecting the pollen type displays a pollen safety data sheet;
- wherein selecting the pathogen safety data sheet displays pathogen type information which comprises an exposure control to and a personal protection from the pathogen; and
- wherein selecting the pollen safety data sheet displays pollen type information which comprises the exposure control to and the personal protection from the pollen.

6. The wearable device of claim 5, wherein the microbiome mobile application is configured to be installed on a smartwatch, or a mobile device; and
- wherein the smart band sends and receives signals through a wireless network to the microbiome mobile application installed on the smartwatch, or the mobile device.

7. The wearable device of claim 6, wherein a set of wearable device alerts comprises:
- a pathogen biosafety alert sent to the microbiome mobile application when the pathogen biosafety level is above a predetermined threshold level in the nasal cavity, oral cavity, surface, or in the surrounding air;
- a pollen allergy alert sent to the microbiome mobile application when the pollen allergy level is above a predetermined threshold level in the surrounding air;
- a dust mite allergy alert sent to the microbiome mobile application when the dust mite allergen level is above a predetermined threshold level in the surrounding air;
- an air quality alert sent to the microbiome mobile application when the air quality level is above a predetermined threshold level in the surrounding air;
- wherein the pathogen biosafety alert is configured to sterilize the pathogen in the nasal cavity, the oral cavity, on the surface, or the surrounding air; and
- wherein the smart band sends and receives signals through the wireless network to the microbiome mobile application.

8. A system comprising:
a wearable device comprising:
- a smart band, wherein the smart band comprises a microbial biosensor, a particulate matter sensor, an enviro sensor, a single board computer, a power supply unit, a band fastener, and a set of watch adapters;
- a display unit, wherein the display unit comprises a touchscreen, a display unit power button, a crown, and a set of attachment slots;
- wherein the microbial biosensor comprises a transmitter, a receiver, a sterilizer, a picocamera, and a microbial biosensor power button;
  - wherein the microbial biosensor is configured to detects, measures, and monitors a pathogen count, a pathogen type, a pathogen concentration, and a pathogen biosafety level in a nasal cavity, an oral cavity, or on a surface;
  - wherein the microbial biosensor is configured to detects, measures, and monitors a beneficial microorganism count, a beneficial microorganism type, and a beneficial microorganism concentration in the nasal cavity, the oral cavity, or on the surface;
  - wherein the sterilizer is configured to kill the pathogen type;
- wherein the particulate matter sensor comprises a sensing cavity;
  - wherein the sensing cavity is configured to detects suspended particles of picometer, nanometer, and micrometer sizes and is configured to differentiate and identify the suspended particles in the air;
- wherein the enviro sensor comprises a set of sensors;
- wherein the power supply unit comprises a wireless charging unit, a battery, a charging port, and a band power button;
a microbiome mobile application;
a mobile device;
a cloud server;
a laboratory testing facility;
a laboratory computer;
a laboratory information system;
- wherein the smart band sends and receives signals through a wireless network to the microbiome mobile application installed on the mobile device, and to the cloud server;
- wherein the wearable device sends a microbial biosensor data, a particulate matter sensor data, and an enviro sensor data to the cloud server;
- wherein the microbial biosensor data, the particulate matter sensor data, and the enviro sensor data determine a cause of a disorder to report out a user test result;
- wherein the user test result is reviewed in conjunction with the physiological data to determine a root cause of the disorder to treat a disease;
- wherein a neighborhood public biosafety alert is sent to the wearable device when the pathogen biosafety level is above a predetermined threshold level, indicating that there is a pathogen in the surrounding air which can result in disease outbreak; and
- wherein the neighborhood public biosafety alert is configured to output a corrective and a preventive measure to reduce exposure to the pathogen.

9. The system of claim 8, wherein the wearable device sends a pathogen biosafety alert to the microbiome mobile application installed on the mobile device, when the pathogen biosafety level is above a predetermined threshold level in the nasal cavity, the oral cavity, on the surface, or in the surrounding air; and
- wherein the pathogen biosafety alert is configured to sterilize the pathogen in the nasal cavity, the oral cavity, on the surface, or the surrounding air.

* * * * *